United States Patent
Kitazawa et al.

(10) Patent No.: US 9,192,624 B2
(45) Date of Patent: Nov. 24, 2015

(54) MEDICAL MATERIAL AND METHOD FOR MANUFACTURING SAME

(71) Applicant: Ajinomoto Co., Inc., Tokyo (JP)

(72) Inventors: Manabu Kitazawa, Kawasaki (JP); Satoru Ohashi, Kawasaki (JP); Yoko Masuzawa, Kawasaki (JP); Kousaku Ohkawa, Ueda (JP); Yasuhiko Tabata, Kyoto (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 13/911,776

(22) Filed: Jun. 6, 2013

(65) Prior Publication Data

US 2013/0266620 A1 Oct. 10, 2013

Related U.S. Application Data

(63) Continuation of application No. PCT/JP2011/078217, filed on Dec. 6, 2011.

(30) Foreign Application Priority Data

Dec. 6, 2010 (JP) ................................ 2010-272043

(51) Int. Cl.
| | |
|---|---|
| A61K 31/785 | (2006.01) |
| D01F 6/68 | (2006.01) |
| A61L 27/18 | (2006.01) |
| A61L 27/34 | (2006.01) |
| A61L 31/06 | (2006.01) |
| A61L 31/10 | (2006.01) |
| A61L 27/00 | (2006.01) |
| D01D 5/00 | (2006.01) |

(52) U.S. Cl.
CPC ............... *A61K 31/785* (2013.01); *A61L 27/00* (2013.01); *A61L 27/18* (2013.01); *A61L 27/34* (2013.01); *A61L 31/06* (2013.01); *A61L 31/10* (2013.01); *D01D 5/0038* (2013.01); *D01F 6/68* (2013.01)

(58) Field of Classification Search
None
See application file for complete search history.

(56) References Cited

U.S. PATENT DOCUMENTS

2002/0128444 A1* 9/2002 Gingras et al. ................. 530/350
2006/0134166 A1* 6/2006 Luthra et al. ................... 424/422

FOREIGN PATENT DOCUMENTS

| JP | 63-277636 A | 11/1988 | |
|---|---|---|---|
| JP | 2001-136960 A | 5/2001 | |
| JP | 2005-290610 A | 10/2005 | |
| JP | 2005-312338 A | 11/2005 | |
| JP | 2006-087396 A | 4/2006 | |
| JP | 2008-502376 A | 1/2008 | |
| JP | 2008-163520 A | 7/2008 | |
| JP | 2008-308780 A | 12/2008 | |
| WO | WO 2004/089433 A1 | 10/2004 | |
| WO | WO 2010/143646 A1 | 12/2010 | |
| WO | WO 2011/163232 A2 * | 12/2011 | ............... D01D 5/00 |

OTHER PUBLICATIONS

English translation of the International Search Report and Written Opinion issued Jan. 24, 2012 in PCT/JP2011/078217.
G.R. Edson, et al "Electrospinning of Hyperbranched Poly-L-Lysine/Polyaniline Nanofibers for Application in Cardiac Tissue Engineering" Journal of Macromolecular Science, Part A, vol. 47 No. 12, Oct. 12, 2010, pp. 1203-1207.
Ken-Ichi Minato, et al., "Chain Conformations of Poly(γ-benzyl-L-glutamate) Pre and Post an Electrospinning Process" Macromolecular Bioscience, vol. 6, 2006, pp. 487-495.
K. Fujimoto, "Interaction between Amphoteric Polypeptides and Primary Culture Hepatocytes" Polymer Preprints, vol. 40 No. 9, 1991, pp. 3173-3175, with English translation of introduction.
K. Fujimoto, "Interaction between Amphoteric Polypeptides and Adult Rat Hepatocytes in Primary Culture" Jpn J Artif Organs, Jinko Zoki 21, 1992, pp. 212-216, with English Abstract.
Zhijiang Song, "Layer-by-Layer Buildup of Poly(L-glutamic acid)/Chitosan Film for Biologically Active Coating" Macromolecular Bioscience, vol. 9, 2009, pp. 268-278.
Office Action issued Sep. 29, 2015 in Japanese Patent Application No, 2012-547880, national phase entered Apr. 2, 2013 (with English-language translation).

* cited by examiner

*Primary Examiner* — Karlheinz R Skowronek
*Assistant Examiner* — Mindy Newman
(74) *Attorney, Agent, or Firm* — Oblon, McClelland, Maier & Neustadt, L.L.P.

(57) ABSTRACT

The present invention aims to provide a medical material which is safe for the live body, has high biocompatibility and is useful for promotion of cell differentiation. The present invention produces a medical material for promoting cell differentiation, which contains polyamino acid as a main component, wherein the polyamino acid contains at least one kind of amino acid residue selected from the group consisting of an alanine residue, a valine residue, a leucine residue, an isoleucine residue, a phenylalanine residue, a glycine residue, a glutamine residue, an aspartic acid residue optionally containing a protecting group in the side chain, a tyrosine residue optionally containing a protecting group in the side chain, a tryptophan residue optionally containing a protecting group in the side chain, a lysine residue optionally containing a protecting group in the side chain, and a glutamic acid residue optionally containing a protecting group in the side chain.

21 Claims, 1 Drawing Sheet

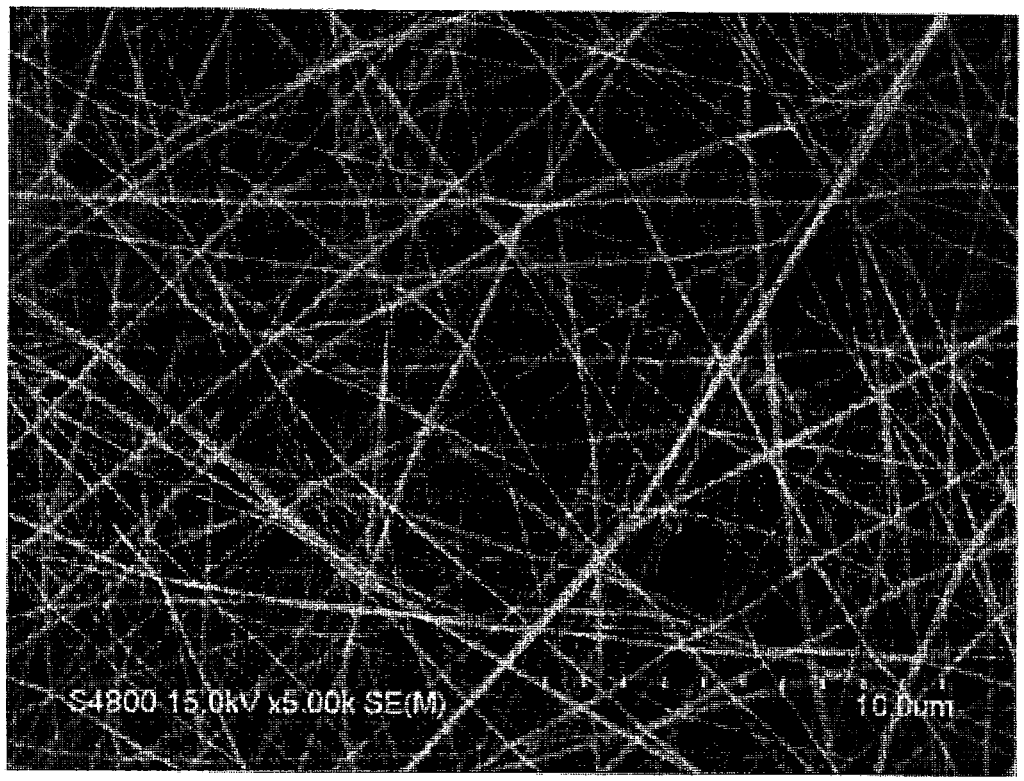

MEDICAL MATERIAL AND METHOD FOR MANUFACTURING SAME

TECHNICAL FIELD

The present invention relates to a medical material useful for promoting cell differentiation and the like and a production method thereof. In more detail, the present invention relates to a medical material containing a polyamino acid having a particular amino acid residue as a main component and a production method thereof.

BACKGROUND ART

In an attempt to regenerate an impaired and defective biological tissue, the research and development of a structure that functions as a scaffold for tissues and cells has been ongoing in recent years as a part of the regenerative medicine. As a structure that functions as a scaffold, sponge, honeycomb, fiber structures wherein fibers are multi-layered such as nonwoven fabric and the like, films and coatings are known.

Medical materials such as scaffold for tissues and cells desirably have biodegradability and biocompatibility in combination. From such aspect, many production examples of medical materials using collagen, gelatin, cellulose, chitin, chitosan, polylactic acid and the like are disclosed. For example, as a fiber structure medical material, those using chitosan, chondroitin sulfate, polysaccharides such as pectin and the like are disclosed (patent document 1). A fiber structure can be generally formed by a method called electrospinning method. A polymer compound is dissolved in a solvent to give a solution, the polymer compound solution is discharged under application of a high voltage to form a fiber, and the fiber is accumulated on a substrate (collector), whereby a fiber structure can be obtained. A fiber structure produced using chitosan under controlled production conditions of such electrospinning method is also disclosed (patent documents 2, 3). However, all the above-mentioned fiber structures do not have a desirable shape as a fiber structure, even though they are medical materials provided with biodegradability. For example, the width of the fiber diameter may be extremely nonuniform, or bonding of fibers may be observed. Even if the width of the fiber diameter could be controlled, the production conditions are impractical since the fiber formation stage requires a markedly long time and the like. In some cases, moreover, since chitosan is not completely dissolved in the solution, a satisfactory fiber structure is unattainable.

As for fiber structures, a method using poly-γ-benzyl-L-glutamic acid as a material is disclosed (non-patent document 1). In this method, the fiber diameter is controlled by dissolving the material at a low concentration in an organic solvent with low polarity, thereby suppressing interactions between molecules. However, formation of the fiber becomes difficult when the concentration of the solution reaches some low levels, and the fiber diameter has not actually been reduced to a satisfactory thinness. When a fiber structure is used as a medical material, it is desirably constituted by a thinner fiber, particularly nanometer-order fiber (nanofiber), in view of the degradability in the live body. However, a fiber structure made of a thin fiber such as nanofiber requests precise control of the production conditions, materials to be used and the like, which makes production by an electrospinning method difficult to achieve.

As other biodegradable materials, a fiber structure medical material using polylactic acid is disclosed (patent document 4). However, in this fiber structure, a nanometer-order fiber diameter has not been actually achieved. It is also suggested that polylactic acid lacks flexibility, is poor in compatibility with soft tissues, and causes inflammatory reaction in the live body, and therefore, is not a biodegradable material sufficiently safe as a medical material.

Besides the fiber structure, films and coatings are utilized, and a single cell culture obtained by forming a film from extracellular matrix components such as collagen, fibronectin and laminin (patent document 5), and a cell culture vessel coated with a similar extracellular matrix component are disclosed (patent document 6). However, extracellular matrix components are highly unstable and the property may be degraded in about several months even by chilled storage. Among the extracellular matrix components, collagen is widely used. However, the problems of BSE (bovine spongiform encephalopathy), foot-and-mouth disease and the like have made the use thereof difficult, and collagen itself is easily denatured in a production step such as film formation and the like. In the current situation, therefore, handling of collagen while maintaining its inherent function is difficult. To confer strength, formaldehyde and glutaraldehyde may be used for crosslinking. However, since these organic substances show extremely high toxicity, they are problematic in safety.

Patent document 7 describes a cell culture film made from a copolymer of polyamino acid and urethane. Non-patent documents 2 and 3 describe that a resin made from a random copolymer of 3 kinds of amino acids (glutamic acid, lysine, leucine) grow hepatocytes with good cell adhesiveness. Furthermore, non-patent document 4 describes that a laminate film of α-polyglutamic acid and chitosan shows good adhesiveness to one of myoblasts, and promotes growth. In recent years, however, a practical material that promotes differentiation of undifferentiated cell is increasingly desired along with the development of the study of iPS cells, and a material satisfying such demand has not been found.

DOCUMENT LIST

Patent Documents patent document 1: JP-A-2005-290610
patent document 2: JP-A-2008-163520
patent document 3: JP-A-2008-308780
patent document 4: WO2004/089433
patent document 5: JP-A-2005-312338
patent document 6: JP-A-2006-87396
patent document 7: JP-A-2001-136960

Non-Patent Documents non-patent document 1: Ken-Ichi Minato et al, Macromolecular Bioscience, 2006, 6, 487-495.
non-patent document 2: POLYMER PREPRINTS, Vol. 40, No 9 (1991), 3173-3175.
non-patent document 3: Jinko Zoki 21(1), 212-216. (1992)
non-patent document 4: Macromol. Biosci. 2009, 9, 268-278.

SUMMARY OF THE INVENTION

Problems to be Solved by the Invention

The problems to be solved by the present invention is provision of a medical material which is safe for living organisms, has high biocompatibility, and is useful as a scaffold for biological tissues or cells and for the promotion of cell differentiation.

Means of Solving the Problems

The present inventors have conducted intensive studies and found that the above-mentioned problem can be solved by adding a polyamino acid having a particular amino acid residue as a main component to a medical material, which resulted in the completion of the present invention.

Accordingly, the present invention provides the following.

(1) A medical material for promoting cell differentiation, which comprises polyamino acid as a main component, wherein the polyamino acid comprises at least one kind of amino acid residue selected from the group consisting of an alanine residue, a valine residue, a leucine residue, an isoleucine residue, a phenylalanine residue, a glycine residue, a glutamine residue, an aspartic acid residue optionally containing a protecting group in the side chain, a tyrosine residue optionally containing a protecting group in the side chain, a tryptophan residue optionally containing a protecting group in the side chain, a lysine residue optionally containing a protecting group in the side chain, and a glutamic acid residue optionally containing a protecting group in the side chain.

(2) The medical material of (1), wherein the polyamino acid is a copolymer containing two kinds of amino acid residues selected from the group consisting of an alanine residue, a valine residue, a leucine residue, an isoleucine residue, a phenylalanine residue, a lysine residue optionally containing a protecting group in the side chain, and a glutamic acid residue optionally containing a protecting group in the side chain.

(3) The medical material of (2), wherein one of the two kinds of amino acid residues is a glutamic acid residue optionally containing a protecting group in the side chain.

(4) The medical material of (3), wherein the other of the two kinds of amino acid residues is an alanine residue, a valine residue, a leucine residue, an isoleucine residue, or a phenylalanine residue.

(5) The medical material of (3), wherein one of the two kinds of amino acid residues is a lysine residue optionally containing a protecting group in the side chain.

(6) The medical material of (5), wherein the other of the two kinds of amino acid residues is an alanine residue, a valine residue, a leucine residue, an isoleucine residue, or a phenylalanine residue.

(7) The medical material of (2), wherein said one of the two kinds of amino acid residues is a phenylalanine residue.

(8) The medical material of (7), wherein the other of the two kinds of amino acid residues is a valine residue, or a leucine residue.

(9) The medical material of (1) or (2), which is a fiber structure.

(10) The medical material of (9), wherein the fiber has an average fiber diameter of not less than 50 nm and less than 500 nm.

(11) The medical material of (9) or (10), wherein the polyamino acid contains a glutamic acid residue optionally containing a protecting group in the side chain.

(12) The medical material of (11), wherein the polyamino acid further contains an alanine residue, a valine residue, a leucine residue, an isoleucine residue, or a phenylalanine residue.

(13) The medical material of (9) or (10), wherein the polyamino acid contains a lysine acid residue optionally containing a protecting group in the side chain.

(14) The medical material of (13), wherein the polyamino acid further contains an alanine residue, a valine residue, a leucine residue, an isoleucine residue, or a phenylalanine residue.

(15) The medical material of (9) or (10), wherein the polyamino acid contains a phenylalanine residue.

(16) The medical material of (15), wherein the polyamino acid further contains a valine residue, or a leucine residue.

(17) The medical material of (1) or (2), which is a film.

(18) The medical material of (17), wherein the polyamino acid contains a glutamic acid residue optionally containing a protecting group in the side chain.

(19) The medical material of (18), wherein the polyamino acid further contains a valine residue, or an isoleucine residue.

(20) The medical material of (17), wherein the polyamino acid contains a lysine residue optionally containing a protecting group in the side chain.

(21) The medical material of (20), wherein the polyamino acid further contains an alanine residue, a valine residue, or an isoleucine residue.

(22) The medical material of (1) or (2), which is a coating.

(23) The medical material of (22), wherein the polyamino acid contains a lysine residue optionally containing a protecting group in the side chain.

(24) The medical material of (23), wherein the polyamino acid further contains an alanine residue, or a phenylalanine residue.

(25) A method of producing the medical material of any of (9)-(16), comprising the following steps:

step 1) a step of dissolving polyamino acid in a solvent to give a solution, step 2) a step of continuously discharging the aforementioned solution charged in a syringe from a nozzle set at the tip of a syringe, step 3) a step of applying a high voltage between a nozzle and a collector by a high voltage generator during the aforementioned discharge, step 4) a step of changing the aforementioned discharged solution into the shape of a fiber between the nozzle and the collector, step 5) a step of collecting the fiber on a collector.

(26) The production method of (25), wherein the polyamino acid solution in step 1 has a concentration of 1-20 wt %, the discharge rate of the polyamino acid solution in step 2 is 1-20 ml/hour, the voltage to be applied between the nozzle and the collector in step 3 is 11-45 kV, and an distance between the nozzle and the collector in step 4 is 10-40 cm.

(27) The production method of (25) or (26), wherein the solvent in step 1 is one or more kinds selected from the group consisting of trifluoroacetic acid, acetic acid, dichloromethane, chloroform, 1,2-dichloroethane, 1,1,1,3,3,3-hexafluoro-2-propanol, 2,2,2-trifluoroethanol, N,N-dimethylformamide and water.

(28) A method for promoting cell differentiation, which comprises (a) contacting a cell with a surface of a medical material comprising a polyamino acid and cultivating the cell, or (b) transplanting a medical material comprising a polyamino acid to a subject in need thereof, wherein the polyamino acid comprises at least one kind of amino acid residue selected from the group consisting of an alanine residue, a valine residue, a leucine residue, an isoleucine residue, a phenylalanine residue, a glycine residue, a glutamine residue, an aspartic acid residue optionally containing a protecting group in the side chain, a tyrosine residue optionally containing a protecting group in the side chain, a tryptophan residue optionally containing a protecting group in the side chain, a lysine residue optionally containing a protecting group in the side chain, and a glutamic acid residue optionally containing a protecting group in the side chain.

(29) The method of (28), wherein the polyamino acid is a copolymer containing two kinds of amino acid residues selected from the group consisting of an alanine residue, a valine residue, a leucine residue, an isoleucine residue, a phenylalanine residue, a lysine residue optionally containing a protecting group in the side chain, and a glutamic acid residue optionally containing a protecting group in the side chain.
(30) The method of (29), wherein one of the two kinds of amino acid residues is a glutamic acid residue optionally containing a protecting group in the side chain.
(31) The method of (30), wherein the other of the two kinds of amino acid residues is an alanine residue, a valine residue, a leucine residue, an isoleucine residue, or a phenylalanine residue.
(32) The method of (30), wherein one of the two kinds of amino acid residues is a lysine residue optionally containing a protecting group in the side chain.
(33) The method of (32), wherein the other of the two kinds of amino acid residues is an alanine residue, a valine residue, a leucine residue, an isoleucine residue, or a phenylalanine residue.
(34) The method of (29), wherein said one of the two kinds of amino acid residues is a phenylalanine residue.
(35) The method of claim 7 (34), wherein the other of the two kinds of amino acid residues is a valine residue, or a leucine residue.
(36) The method of (28), wherein the medical material is a fiber structure.
(37) The method of (36), wherein the fiber has an average fiber diameter of not less than 50 nm and less than 500 nm.
(38) The method of (36), wherein the polyamino acid comprises a glutamic acid residue optionally containing a protecting group in the side chain.
(39) The method of (38), wherein the polyamino acid further comprises an alanine residue, a valine residue, a leucine residue, an isoleucine residue, or a phenylalanine residue.
(40) The method of (36), wherein the polyamino acid comprises a lysine acid residue optionally containing a protecting group in the side chain.
(41) The method of (40), wherein the polyamino acid further comprises an alanine residue, a valine residue, a leucine residue, an isoleucine residue, or a phenylalanine residue.
(42) The method of (36), wherein the polyamino acid comprises a phenylalanine residue.
(43) The method of (41), wherein the polyamino acid further comprises a valine residue, or a leucine residue.
(44) The method of (28), wherein the medical material is a film.
(45) The method of (44), wherein the polyamino acid comprises a glutamic acid residue optionally containing a protecting group in the side chain.
(46) The method of (45), wherein the polyamino acid further comprises a valine residue, or an isoleucine residue.
(47) The method of (44), wherein the polyamino acid comprises a lysine residue optionally containing a protecting group in the side chain.
(48) The method of (47), wherein the polyamino acid further comprises an alanine residue, a valine residue, or an isoleucine residue.
(49) The method of (28), wherein the medical material is a coating.
(50) The method of (49), wherein the polyamino acid comprises a lysine residue optionally containing a protecting group in the side chain.
(51) The method of (50), wherein the polyamino acid further comprises an alanine residue, or a phenylalanine residue.
(52) The method of (28), wherein said method comprises contacting a cell with a surface of a medical material comprising a polyamino acid and cultivating the cell.
(53) The method of (28), wherein said method comprises transplanting a medical material comprising a polyamino acid to a subject in need thereof,
(54) A method of producing the medical material comprising a polyamino acid,
which comprises:
1) dissolving a polyamino acid in a solvent to give a solution,
2) continuously discharging the solution charged in a syringe from a nozzle set at the tip of a syringe,
3) applying a high voltage between a nozzle and a collector by a high voltage generator during the discharge,
4) changing the discharged solution into the shape of a fiber between the nozzle and the collector,
5) collecting the fiber on a collector
wherein the polyamino acid comprises at least one kind of amino acid residue selected from the group consisting of an alanine residue, a valine residue, a leucine residue, an isoleucine residue, a phenylalanine residue, a glycine residue, a glutamine residue, an aspartic acid residue optionally containing a protecting group in the side chain, a tyrosine residue optionally containing a protecting group in the side chain, a tryptophan residue optionally containing a protecting group in the side chain, a lysine residue optionally containing a protecting group in the side chain, and a glutamic acid residue optionally containing a protecting group in the side chain, and
wherein the medical material is a fiber structure.
(55) The production method of (54), wherein the polyamino acid solution in 1) has a concentration of 1-20 wt %, the discharge rate of the polyamino acid solution in 2) is 1-20 ml/hour, the voltage to be applied between the nozzle and the collector in 3) is 11-45 kV, and an distance between the nozzle and the collector in 4) is 10-40 cm.
(56) The production method of (54), wherein the solvent in 1) is one or more kinds selected from the group consisting of trifluoroacetic acid, acetic acid, dichloromethane, chloroform, 1,2-dichloroethane, 1,1,1,3,3,3-hexafluoro-2-propanol, 2,2,2-trifluoroethanol, N,N-dimethylformamide and water.

Effect of the Invention

The medical material of the present invention is useful for promoting cell differentiation. The medical material of the present invention is safe for living organisms since the material used as a main component is constituted by amino acids widely present in the live body, and shows high biocompatibility. It is also possible to form a medical material superior in the cell or tissue adhesion suppressive effect or cell adhesion effect, depending on the kind of the amino acid to be used and the state of the protecting group. As a result, the medical material of the present invention can be utilized for a scaffold for a wide range of application. When the medical material of the present invention is a fiber structure, the fiber structure is superior in the degradability in the live body since it has a uniformly controlled nanometer-order fiber diameter. Moreover, it is also superior in the flexibility since the fibers thereof are not bonded to each other.

BRIEF DESCRIPTION OF THE DRAWINGS

FIG. 1 is a photograph, by a scanning electron microscope (SEM), of the surface of a fiber structure made of poly-L-alanine, which was obtained by the operation in Production Example 1.

DESCRIPTION OF EMBODIMENTS

The embodiments of the present invention are explained below.

The medical material of the present invention is characterized by the use of polyamino acid as a main component. Polyamino acid is a polymer constituted by plural amino acid residues, and can be prepared using various amino acids or a derivative thereof. The amino acid to be used generally includes neutral amino acid, acidic amino acid, basic amino acid, aromatic amino acid and the like and, as the neutral amino acid, non-polar neutral amino acid and polar neutral amino acid are used. As polyamino acid, one constituted by one or more kinds of amino acid residues can be used. In the present invention, a polyamino acid constituted by 1-3 kinds (more preferably one kind or two kinds) of amino acid residues is preferable. In the present specification, the amino acid residue refers to an amino acid unit (original amino acid unit when amino acids are bonded to form a polyamino acid), which is a constituent component of polyamino acid. When the kind of the amino acid is specifically shown, the "residue" attached to the end of the name indicates that it is an amino acid residue. For example, when alanine is used in the constitution of polyamino acid, the part corresponding to alanine in the polyamino acid is referred to as an alanine residue.

The above-mentioned polyamino acid is characterized in that it contains at least one kind of amino acid residue selected from the group consisting of an alanine residue, a valine residue, a leucine residue, an isoleucine residue, a phenylalanine residue, a glycine residue, a glutamine residue, an aspartic acid residue optionally containing a protecting group in the side chain, a tyrosine residue optionally containing a protecting group in the side chain, a tryptophan residue optionally containing a protecting group in the side chain, a lysine residue optionally containing a protecting group in the side chain, and a glutamic acid residue optionally containing a protecting group in the side chain.

Other amino acid residues can also be contained as long as they do not influence the effect of the present invention. Examples of other amino acid residue include sarcosine residue; N-methylalanine residue; β-alanine residue; γ-aminobutyric acid residue; norvaline residue; norleucine residue; phenylglycine residue; methionine residue; cysteine residue; cysteine derivative residues such as S-benzyl-cysteine residue and the like; cysteine residue; asparagine residue; ornithine residue; ornithine derivative residues such as Nδ-benzyloxycarbonyl-ornithine residue, Nα-benzyloxycarbonyl-ornithine residue and the like; arginine residue; arginine derivative residues such as Nω-methyl-arginine residue, Nω-nitro-arginine residue and the like; histidine residue; histidine derivative residues such as N(Im)-methyl-histidine residue and the like; proline residue; proline derivative residues such as hydroxyproline residue, O-benzylhydroxyproline residue and the like; serine residue; serine derivative residues such as O-benzyl-serine residue, O-acetyl-serine residue and the like; threonine residue; threonine derivative residues such as O-benzyl-threonine residue, O-acetyl-threonine residue and the like; DOPA residue and the like. When an amino acid residue contains an asymmetric carbon atom, the amino acid residue may be any of an L form, a D form and a DL form, with preference given to an L form.

The aspartic acid residue, tyrosine residue, tryptophan residue, a lysine residue and glutamic acid residue constituting the polyamino acid may have a protecting group bonded to the side chain thereof. In the present specification, the protecting group refers to an atom group used to protect a characteristic group with high reactivity in the side chain of an amino acid residue from a reaction with other compound. The protecting group may be bonded during preparation of polyamino acid, or bonded after preparation thereof. The protecting group may be bonded to the side chain of all amino acid residues constituting a polyamino acid, or only to the side chain of a part of amino acid residues. Only one kind of the protecting group may be used, or two or more kinds of protecting groups may be used.

The protecting group is not particularly limited as long as it can convert a characteristic group with high reactivity in the side chain of an amino acid residue to an inactive functional group. For example, when the amino acid residue constituting a polyamino acid is a lysine residue, an amino-protecting group can be used. As the amino-protecting group, the groups described in Greene's Protective Groups in Organic Synthesis (Wiley-Interscience 2006) can be mentioned. Specific examples thereof include acyl group, alkyl group, aralkyl group, silyl group, methoxymethyl group, methylthiomethyl group, benzyloxymethyl group, methoxyethoxymethyl group, tetrahydropyranyl group, methoxycarbonyl group (Moc group), 9-fluorenylmethyloxycarbonyl group (Fmoc group), 2,2,2-trichloroethoxycarbonyl group, benzyloxycarbonyl group (Cbz group), p-methoxybenzyloxycarbonyl group, tert-butoxycarbonyl group (Boc group), p-biphenyl-isopropyloxycarbonyl group, phthaloyl group, trifluoroacetyl group, p-toluenesulfonyl group, o-nitrophenylsulfenyl group, trityl group, benzyl group, 2-benzoyl-1-methylvinyl group, 2-hydroxyallylidene group and the like. Examples of the acyl group include formyl group, C1-6 alkyl-carbonyl group (e.g., acetyl group), C6-8 aryl-carbonyl group, C7-11 aralkyl-carbonyl group (e.g., phenylacetyl group) and the like. These amino-protecting groups are optionally substituted by one or more from a halogen atom (e.g., chlorine atom, bromine atom, fluorine atom), hydroxyl group, C1-6 alkoxy group (e.g., methoxy group), C1-6 haloalkyl group (e.g., trifluoromethyl group), C1-6 haloalkoxy group (e.g., trifluoromethoxy group) and the like. A preferable amino-protecting group in the present invention includes benzyloxycarbonyl group, 9-fluorenylmethyloxycarbonyl group and trifluoroacetyl group.

For example, when the amino acid residue constituting a polyamino acid is an aspartic acid residue or a glutamic acid residue, a carboxyl-protecting group can be used. The carboxyl-protecting group is not particularly limited and, for example, C1-6 alkyl group, C6-10 aryl group, C7-11 aralkyl group and the like can be mentioned. Specific examples thereof can include methyl group, ethyl group, n-propyl group, isopropyl group, n-butyl group, isobutyl group, sec-butyl group, tert-butyl group, phenyl group, benzyl group and the like. Alternatively, p-nitrobenzyl group, phenacyl group, trichloroethyl group, cyclohexyl group and the like can be mentioned, and it can also be protected mainly in the form of an ester. A preferable carboxyl-protecting group in the present invention includes C1-4 alkyl group, which is specifically exemplified by methyl group, ethyl group, n-propyl group, isopropyl group, n-butyl group, isobutyl group, sec-butyl group and tert-butyl group. These carboxyl-protecting groups are optionally substituted by one or more from a halogen atom (e.g., chlorine atom, bromine atom, fluorine atom), hydroxyl group, C1-6 alkoxy group (e.g., methoxy group), C1-6 haloalkyl group (e.g., trifluoromethyl group), C1-6 haloalkoxy group (e.g., trifluoromethoxy group) and the like.

For example, when the amino acid residue constituting a polyamino acid is a serine residue or a threonine residue, a hydroxy-protecting group can be used. Examples of the hydroxy-protecting group include acyl group, alkoxycarbonyl group, alkyl group, aralkyl group, silyl group and the like. Examples of the acyl group include C1-8 acyl groups such as formyl group, acetyl group, trifluoroacetyl group, isobutyloyl group, pivaloyl group, benzoyl group, 4-toluoyl group, 4-chlorobenzoyl group and the like. Examples of the alkoxycarbonyl group include methoxycarbonyl group, ethoxycarbonyl group, propoxycarbonyl group, butoxycarbonyl group, sec-butoxycarbonyl group, 2-trimethylsilylethoxycarbonyl group and the like. Examples of the alkyl group include C1-4 alkyl groups such as methyl group, ethyl group, n-propyl group, isopropyl group, n-butyl group, tert-butyl group and the like. Examples of the aralkyl group include C7-21 aralkyl groups such as benzyl group, 4-monomethoxybenzyl group, trityl group, 4-monomethoxytrityl group, 4,4'-dimethoxytrityl group and the like. Examples of the silyl group include trisubstituted silyl groups such as trimethylsilyl group, triethylsilyl group, tert-butyldimethylsilyl group and the like. Besides these, hydroxy-protecting groups such as methoxymethyl group, methylthiomethyl group, benzyloxymethyl group, methoxyethoxymethyl group, tetrahydropyranyl group, methoxycarbonyl group, 9-fluorenylmethoxycarbonyl group, 2,2,2-trichloroethoxycarbonyl group, benzyloxycarbonyl group, tert-butoxycarbonyl group and the like can be used.

For example, when the amino acid residue constituting a polyamino acid is a tryptophan residue, an indolyl-protecting group can be used. Examples of the indolyl-protecting group include formyl group and the like. When polyamino acid contains an amino acid residue other than aspartic acid residue, tyrosine residue, tryptophan residue, a lysine residue and glutamic acid residue, such amino acid residue may also be bonded with a protecting group. Besides the above-mentioned protecting groups, as a guanidino-protecting group used for arginine residue, nitro group, p-toluenesulfonyl group, benzyloxycarbonyl group and the like can be mentioned. As an imidazolyl-protecting group used for histidine residue, benzyl group, benzyloxycarbonyl group, p-toluenesulfonyl group, trityl group, diphenylmethyl group, dinitrofluorobenzene group, tert-butoxycarbonyl group and the like can be mentioned. As a mercapto-protecting group used for methionine residue, benzyl group, substituted benzyl groups such as p-methoxybenzyl group and the like; trityl group; benzhydryl group; acetamidemethyl group; carbomethoxysulfenyl group and the like can be mentioned.

Polyamino acid having a protecting group can be subjected to deprotection to remove a part of or all of the protecting groups. In the present invention, the percentage of protecting group (protecting group content) in polyamino acid can be adjusted by deprotection, and the use of a medical material as a scaffold can be selected according to the protecting group content. By appropriately setting the protecting group content, the cell differentiation promoting effect and cell adhesion effect can be controlled according to the kind of the amino acid residue to be used. In the present invention, the protecting group content is preferably not less than 65% and less than 100%, more preferably not less than 70% and less than 100%, more preferably not less than 80% and less than 100%, still more preferably not less than 90% and less than 100%, especially preferably not less than 95% and less than 100%, particularly preferably not less than 98% and less than 100%.

The protecting group content can be derived by measuring the spectrum to be the index of the protecting group bonded to an amino acid residue contained in polyamino acid, and calculating the ratio of the amino acid residue bonded with a protecting group relative to the total amino acid residues to which a protecting group can be bonded. The spectrum to be the index of the protecting group can be measured in the state of a solid or liquid and, for example, Fourier-transform infrared spectroscopy (FT-IR), nuclear magneticresonance (NMR), Thermal spectrum, Raman Spectrum, Electron Spin Resonance, X-ray absorption fine structure (XAFS), X-ray analysis, fluorescence X-ray, mass spectrometry (MS), TOF-SIMS, XPS, ultraviolet visible•photoluminescence and the like can be used, and FT-IR Attenuated Total Reflection in FT-IR can be preferably utilized. The FT-IR Attenuated Total Reflection can serve for the measurement of forms such as fiber structure, film, coating, powder, pellet and the like. The protecting group content can be calculated by examining an index that can be determined between polyamino acid having a protecting group in the side chain and polyamino acid without having a protecting group in a part of or all side chains. In addition, conversion or correction can also be performed using, where necessary, the second index. The detail of the method for determining the protecting group content is shown in the below-mentioned Examples.

The polyamino acid used in the present invention characteristically has a cell differentiation promoting activity. Here, the "cell differentiation promoting activity" means an activity to change an undifferentiated cell to a cell having a particular function or structure, and capable of increasing the level of change. The undifferentiated cell is not particularly limited but preferred is a mesenchymal stem cell. The cell differentiation promoting activity can be measured using, for example, a mesenchymal stem cell. Specifically, mesenchymal stem cells are cultured in a medium for mesenchymal stem cell (e.g., mesenchymal stem cell culture medium described in "revised edition cultured cell experiment handbook" (YODOSHA, 2009) pages 314-318) under the conditions of 5% $CO_2$/37° C. for 3 days, the medium is additionally exchanged with an adipocyte differentiation induction medium (e.g., adipocyte differentiation induction medium described in "revised edition cultured cell experiment handbook" (YODOSHA, 2009) pages 314-318), the cells are cultured under the conditions of 5% $CO_2$/37° C. for 4 days, the medium is exchanged with an adipocyte differentiation maintenance medium (e.g., adipocyte differentiation maintenance medium described in "revised edition cultured cell experiment handbook" (YODOSHA, 2009) pages 314-318) and the cells are cultured for 3 days. After 2-3 weeks of culture in the adipocyte differentiation induction medium and the adipocyte differentiation maintenance medium, the amount of cellular DNA and the level of glycerol-3-phosphate dehydrogenase (GPDH) activity are quantified. The amount of cellular DNA can be measured by lysing the cultured cells in sodium lauryl sulfate-containing buffer, and adding Bisbenzimide H33258 Fluorochrome Trihydrochloride. The GPDH activity level can be measured using a commercially available kit (e.g., primary Cell Co., Ltd., GPDH activity measurement kit). The cell differentiation promotion activity can be measured by dividing the GPDH activity level by the amount of cellular DNA, and can be evaluated by comparing with the control. The detail of the measurement method is shown in the below-mentioned Examples.

The polyamino acid contained in the medical material of the present invention can contain the above-mentioned various amino acid residues. When polyamino acid is constituted by one kind of amino acid residue, the amino acid residue is not particularly limited but a glycine residue, an alanine residue, a valine residue, a leucine residue, a lysine residue optionally containing a protecting group in the side chain, or a glutamic acid residue optionally containing a protecting group in the side chain is preferable. Various amino acid residues of lysine residue and glutamic acid residue can contain a protecting group in the side chain. When the protecting group content is adjusted as mentioned above, an amino acid residue containing a protecting group and an amino acid residue without a protecting group are mixed. Despite such case, in the present invention, an amino acid residue containing a protecting group in the side chain encompasses partial presence of an amino acid residue free of a protecting group.

When polyamino acid is constituted by two kinds of amino acid residues, said two kinds of amino acid residues are selected from the group consisting of an alanine residue, a valine residue, a leucine residue, an isoleucine residue, a phenylalanine residue, a glutamine residue, a lysine residue optionally containing a protecting group in the side chain, and a glutamic acid residue optionally containing a protecting group in the side chain. While the combination of the two kinds of amino acid residues is not particularly limited, one kind thereof is preferably a lysine residue optionally containing a protecting group in the side chain, a glutamic acid residue optionally containing a protecting group in the side chain, or a phenylalanine residue.

When one of the two kinds of amino acid residues is the aforementioned lysine residue, the other kind is not particularly limited, but an alanine residue, a leucine residue, an isoleucine residue, a phenylalanine residue, or a valine residue is preferable. That is, the combination of two kinds of amino acid residues is a lysine residue optionally containing a protecting group in the side chain and alanine residue, a lysine residue optionally containing a protecting group in the side chain and leucine residue, a lysine residue optionally containing a protecting group in the side chain and isoleucine residue, or a lysine residue optionally containing a protecting group in the side chain and phenylalanine residue.

When one of the two kinds of amino acid residues is the aforementioned glutamic acid residue, the other kind is not particularly limited, but an alanine residue, a leucine residue, an isoleucine residue, a valine residue, a phenylalanine residue, or glutamine residue is preferable. That is, the combination of two kinds of amino acid residues is a glutamic acid residue optionally containing a protecting group in the side chain and alanine residue, a glutamic acid residue optionally containing a protecting group in the side chain and leucine residue, a glutamic acid residue optionally containing a protecting group in the side chain and isoleucine residue, a glutamic acid residue optionally containing a protecting group in the side chain and valine residue, a glutamic acid residue optionally containing a protecting group in the side chain and phenylalanine residue, or a glutamic acid residue optionally containing a protecting group in the side chain and glutamine residue.

When one of the two kinds of amino acid residues is the aforementioned phenylalanine residue, the other kind is not particularly limited, but a valine residue or a leucine residue preferable. That is, the combination of two kinds of amino acid residues is a phenylalanine residue and valine residue, or a phenylalanine residue and leucine residue.

When polyamino acid is constituted by three kinds of amino acid residues, said three kinds of amino acid residues are preferably selected from the group consisting of a leucine residue, a phenylalanine residue, an aspartic acid residue optionally containing a protecting group in the side chain, a glutamic acid residue optionally containing a protecting group in the side chain, a lysine residue optionally containing a protecting group in the side chain. While the combination of the 3 kinds of amino acid residues is not particularly limited, it can be phenylalanine residue/aspartic acid residue optionally containing a protecting group in the side chain/glutamic acid residue optionally containing a protecting group in the side chain, phenylalanine residue/aspartic acid residue optionally containing a protecting group in the side chain/lysine residue optionally containing a protecting group in the side chain, and leucine residue/glutamic acid residue optionally containing a protecting group in the side chain/lysine residue optionally containing a protecting group in the side chain.

When polyamino acid is constituted by two or more kinds of amino acid residues, the polyamino acid can be a copolymer formed by various amino acid residues. When polyamino acid is a copolymer, various amino acid residues may be configured alternately or regularly by a given unit, or configured irregularly in a random order, and the embodiment of the configuration of amino acid residues may be any. When polyamino acid is constituted by two kinds of amino acid residues, the ratio thereof in a molar ratio can be appropriately selected from 99:1-1:99, preferably 95:5-5:95, more preferably 90:10-10:90. When polyamino acid is constituted by 3 kinds of amino acid residues, each amino acid residue is contained within the range of 1-99 mol %, preferably 10-90 mol %, of the total amino acid residues contained in the polyamino acid.

The polyamino acid used for the medical material of the present invention is not particularly limited as long as it contains the above-mentioned amino acid residue and has cell differentiation promoting activity. Specifically, it is more preferably poly-L-alanine, poly-L-valine, poly-γ-methyl-L-glutamic acid, poly-γ-methyl-L-glutamic acid deprotected by KOH treatment and the like, poly-$N^\epsilon$-benzyloxycarbonyl-L-lysine, poly-L-alanine/γ-methyl-L-glutamic acid deprotected by KOH treatment and the like (6/4 (means copolymer mixed at 60:40 molar ratio, hereinafter the same)), poly-L-leucine/γ-methyl-L-glutamic acid (9/1-6/4) deprotected by KOH treatment and the like, poly-L-alanine/$N^\epsilon$-benzyloxycarbonyl-L-lysine (9/1-3/7) deprotected by HBr treatment and the like, poly-L-phenylalanine/$N^\epsilon$-benzyloxycarbonyl-L-lysine (9/1-3/7) deprotected by HBr treatment and the like, poly-L-valine, poly-γ-methyl-L-glutamic acid, poly-L-alanine/$N^\epsilon$-benzyloxycarbonyl L-lysine (9/1-3/7), poly-L-isoleucine/$N^\epsilon$-benzyloxycarbonyl-L-lysine (6/4), poly-$N^\epsilon$-benzyloxycarbonyl-L-lysine, poly-L-phenylalanine/$N^\epsilon$-benzyloxycarbonyl-L-lysine (6/4), poly-$N^\epsilon$-benzyloxycarbonyl-L-lysine, poly-$N^\epsilon$-benzyloxycarbonyl-L-lysine, poly-L-alanine/γ-methyl-L-glutamic acid (9/1), poly-L-alanine/γ-methyl-L-glutamic acid (6/4), poly-L-leucine/γ-methyl-L-glutamic acid (9/1), poly-L-leucine/γ-methyl-L-glutamic acid (6/4), poly-L-phenylalanine/$N^\epsilon$-benzyloxycarbonyl-L-lysine (9/1-3/7), poly-L-valine/$N^\epsilon$-benzyloxycarbonyl-L-lysine (6/4), poly-L-valine/$N^\epsilon$-benzyloxycarbonyl-L-lysine (6/4) deprotected by HBr treatment and the like, poly-L-leucine, poly-L-valine/γ-methyl-L-glutamic acid (6/4), poly-L-isoleucine/γ-methyl-L-glutamic acid (6/4), poly-L-phenylalanine/γ-methyl-L-glutamic acid (9/1-6/4), poly-L-leucine/L-phenylalanine (1/1), poly-L-valine/L-phenylalanine (1/1), poly-L-leucine/L-glutamic acid (8/2), poly-L-leucine/$N^\epsilon$-benzyloxycarbonyl-L-lysine (9/1-6/4), poly-L-leucine/L-lysine (8/2), poly-L-valine/γ-methyl-L-glutamic acid (6/4) deprotected by KOH treatment and the like, poly-L-phenylalanine/γ-methyl-L-glutamic acid (9/1-6/4) deprotected by KOH treatment and the like, poly-L-isoleucine/$N^\epsilon$-benzyloxycarbonyl-L-lysine (6/4) deprotected by HBr treatment and the like, poly-L-leucine/$N^\epsilon$-benzyloxycarbonyl-L-lysine (9/1-6/4) deprotected by HBr treatment and the like, poly-γ-methyl-L-glutamic acid/L-glutamic acid (8/2), poly-L-isoleucine/γ-methyl-L-glutamic acid (6/4) deprotected by KOH treatment and the like, poly-L-glycine, poly-L-$N^\epsilon$-benzyloxycarbonyl- L-lysine/L-lysine (6/4), or poly-N$^\epsilon$-benzyloxycarbonyl-L-lysine/N$^\epsilon$-t-butoxycarbonylguanidino-L-lysine (6/4).

When polyamino acid is constituted by 3 kinds of amino acid residues, specifically, though not particularly limited, poly-L-phenylalanine/benzyl-L-aspartic acid/γ-methyl-L-glutamic acid (3/2/5), poly-L-phenylalanine/benzyl-L-aspartic acid/N$^\epsilon$-benzyloxycarbonyl-L-lysine (3/2/5), poly-L-leucine/L-glutamic acid/L-lysine (8/1/1), poly-L-phenylalanine/benzyl-L-aspartic acid/γ-methyl-L-glutamic acid (3/2/5) deprotected by KOH treatment and the like, poly-L-phenylalanine/benzyl-L-aspartic acid/N$^\epsilon$-benzyloxycarbonyl-L-lysine (3/2/5) deprotected by HBr treatment and the like, and poly-L-leucine/L-glutamic acid/L-lysine (6/1/3) are preferable.

While the weight average molecular weight of polyamino acid used in the present invention is not particularly limited, it is not less than 1,000. It is preferably not less than 5,000, more preferably not less than 10,000, in the present invention in consideration of the compatibility in the live body. While the weight average molecular weight of polyamino acid is not particularly limited, it can be measured using a measurement device. Generally, it is measured using a gel filtration chromatography apparatus, and the obtained value is calibrated using a standard substance to give a weight average molecular weight.

While the viscosity average molecular weight of the polyamino acid used in the present invention is not particularly limited, it is not less than 1,000. It is preferably not less than 5,000, more preferably not less than 10,000, in the present invention. While the viscosity average molecular weight of the polyamino acid is not particularly limited, it can be measured using a measurement device. Generally, it is measured using a viscometer, and the obtained value is converted using a known calculating formula to give a viscosity average molecular weight.

While the polymerization degree of the polyamino acid used in the present invention is not particularly limited, it is not less than 10. It is preferably not less than 50, more preferably not less than 100, in the present invention in consideration of the compatibility in the live body.

The polyamino acid used in the present invention may be a structure wherein a salt is coordinated with a part of or all groups having polarity in the structure. The ratio of the salt to the groups having polarity is appropriately determined based on the solubility of polyamino acid in a solvent and/or the property of the obtained medical material. Examples of the salt include alkali metal salts such as sodium, potassium and the like; alkaline earth metal salts such as magnesium, calcium and the like; inorganic bases such as ammonia and the like; organic amine salts such as monoethanolamine, diethanolamine, triethanolamine, 2-amino-2-methyl-1-propanol, 2-amino-2-methyl-1,3-propanediol, lysine, ornithine, arginine and the like; inorganic acid salts such as hydrochloride, sulfate, carbonate, phosphate and the like; and organic acid salts such as acetate, tartrate, citrate, p-toluenesulfonate, glycolic acid salt, malate, lactate, fatty acid salt, acidic amino acid salt, pyroglutamate and the like. It may be one kind alone or a combination of two or more kinds thereof.

Besides the above-mentioned amino acid residues, the polyamino acid used in the present invention may further be a structure wherein a compound other than the above-mentioned amino acid residues is polymerized and, for example, a copolymer obtained by polymerization of N-carboxy-α-amino acid anhydride and a urethane prepolymer, and the like can be mentioned.

While the preparation method of polyamino acid used in the present invention is not particularly limited as long as it is a method that prepares a structure wherein amino acid or a derivative thereof is polymerized, for example, a method comprising dissolving or suspending N-carboxy-α-amino acid anhydride or N-carboxy-α-amino acid derivative anhydride in an organic solvent or water and adding a polymerization initiator thereto as necessary can be mentioned. Depending on the kind of the amino acid, polymerization is preferably performed after bonding a protecting group as mentioned above in advance. While the amino acid bonded with a protecting group is not particularly limited, aspartic acid, tyrosine, tryptophan, lysine and glutamic acid are preferable.

Examples of the aforementioned organic solvent include acetone, methylethyl ketone, methylisobutylketone, cyclohexanone, tetrahydrofuran, diethyl ether, diisopropyl ether, petroleum ether, 1,4-dioxane, benzene, toluene, xylene, hexane, cyclohexane, ethyl acetate, butyl acetate, trifluoroacetic acid, acetic acid, formic acid, dichloromethane, chloroform, carbon tetrachloride, 1,2-dichloroethane, trichloroethane, trichloroethylene, trifluoroethane, 1,1,1,3,3,3-hexafluoro-2-propanol, 2,2,2-trifluoroethanol, hexafluoroacetone, methanol, ethanol, 1-propanol, 2-propanol, formamide, N,N-dimethylformamide, N,N-dimethylacetamide, N-methylpyrrolidone, dimethyl sulfoxide, pyridine, acetonitrile, trimethylamine, triethylamine, tributylamine and the like. Only one kind of these may be used or a combination of two or more kinds thereof may be used.

Examples of the aforementioned polymerization initiator include primary diamines such as ethylenediamine, propylenediamine, hexamethylenediamine, 1,4-cyclohexanediamine, 1,2-cyclohexanediamine, o-phenylenediamine, m-phenylenediamine, p-phenylenediamine, toluene-2,4-diamine, 4,4'-diphenylmethanediamine, isophoronediamine and the like, primary monoamines such as methylamine, ethylamine, 1-propylamine and the like, alcoholamines such as methanolamine, ethanolamine, diethanolamine and the like, secondary amines such as dimethylamine, diethylamine, dipropylamine and the like, primary tertiary diamines such as N,N-dimethylethylenediamine, N,N-dimethyl-1,3-propanediamine and the like, tertiary amines such as trimethylamine, triethylamine, tributylamine and the like, amino group-containing polymers such as polyetherdiamine, polyester diamine and the like, primary alcohols such as methanol, ethanol and the like, secondary alcohols such as isopropanol and the like, glycols such as ethylene glycol, propylene glycol, 1,4-butanediol, hexamethylene glycol and the like, hydroxyl group-containing polymers such as polyetherdiol, polyester diol and the like, thiols and the like. Only one kind of these may be used or a combination of two or more kinds thereof may be used.

A method of bonding a protecting group to amino acid can be performed as follows. For example, when amino acid corresponding to N-carboxy-α-amino acid anhydride has a carboxyl group in the side chain thereof, as in glutamic acid, aspartic acid and the like, a salt can be formed by reacting same with an inorganic base or organic base. In addition, a part or all thereof can be converted to an ester group by reacting same with methyl alcohol, ethyl alcohol, benzyl alcohol or the like. When the amino acid has an amino group, such as lysine, ornithine and the like, a salt can be formed by reacting same with inorganic acid or organic acid. It is possible to convert a part or all thereof to a carbamate group by reacting same with benzyloxy chloride, tert-butylcarbonyl chloride, 9-fluorenylmethyloxycarbonyl chloride and the like.

When the amino acid has an indolyl group as in tryptophan and the like, a protecting group can be introduced by reacting same with formic acid and the like. When the amino acid has a guanidino group, as in arginine and the like, a protecting group can be introduced by reacting same with benzyloxycarbonyl chloride, paratoluenesulfonyl chloride and the like. When the amino acid has an imidazole group, as in histidine and the like, a protecting group can be introduced by reacting same with benzyloxycarbonylchloride, trityl chloride and the like. When the amino acid has an amide group, as in glutamine, asparagine and the like, a protecting group can be introduced by reacting same with tritylalcohol, 4,4'-dimethoxybenzhydrylalcohol and the like. When the amino acid has a hydroxy group, as in serine, threonine and the like, a protecting group can be introduced by reacting same with benzyl bromide, benzyl alcohol, 4-nitrobenzyl bromide, 2-methylpropene, and the like. When the amino acid has a phenolic substituent, as in tyrosine and the like, a protecting group can be introduced by reacting same with 2-methylpropene, p-nitrophenylo-bromobenzylcarbonate and the like. When the amino acid has a thioether group, as in cysteine and the like, it can be converted to a sulfoxide group and the like by reacting same with hydrogen peroxide water. When the amino acid has a mercapto group, as in methionine and the like, a protecting group can be introduced by reacting same with tritylalcohol, 4-methylbenzyl bromide and the like.

When polyamino acid is prepared using two or more kinds of amino acids, N-carboxy-α-amino acid (including derivative) anhydrides corresponding to various amino acids are appropriately mixed, dissolved or suspended in an organic solvent, and a polymerization initiator is added as necessary to form a copolymer. The mixing ratio of amino acid when, for example, two kinds of amino acids are used, can be appropriately selected from 99:1-1:99, preferably 95:5-5:95, more preferably 90:10-10:90, in a molar ratio. When, for example, 3 kinds of amino acids are used, the mixing amount of respective amino acids can be controlled such that they are within the range of 1-99 mol %, preferably 10-90 mol %, relative to total amino acid residue contained in polyamino acid. The mixing ratio can be calculated based on the molar ratio of N-carboxy-α-amino acid anhydride used. The obtained copolymer generally has an amino acid residue constitution according to the molar ratios of the mixed various amino acids.

It is possible to increase the solubility in an organic solvent by forming a copolymer by mixing and/or polymerizing N-carboxy-α-amino acid anhydride different from N-carboxy-α-aliphatic amino acid anhydride and N-carboxy-α-aromatic amino acid anhydride with N-carboxy-α-aliphatic amino acid anhydride or N-carboxy-α-aromatic amino acid anhydride. As such N-carboxy-α-amino acid anhydride, preferred is aspartic acid-β-methyl ester, aspartic acid-β-benzyl ester, glutamic acid-γ-methyl ester, $N^\epsilon$-benzyloxycarbonyl-lysine, $N^\delta$-benzyloxycarbonyl-ornithine, or N-carboxy-α-amino acid (including derivative) anhydride corresponding to O-benzyl-serine or O-benzyl-threonine, and more preferred is N-carboxy-α-amino acid anhydride corresponding to glutamic acid-γ-methyl ester or $N^\epsilon$-benzyloxycarbonyl-lysine. Only one kind of these may be used or a combination of two or more kinds thereof may be used.

Examples of the preparation method of polyamino acid used in the present invention include a method using microorganism to prepare ε-polylysine and the like, besides a method using the aforementioned N-carboxy-α-amino acid anhydride or N-carboxy-α-amino acid derivative anhydride.

After preparation as mentioned above, polyamino acid can also be further subjected to deprotection. That is, a protecting group bonded to the side chain of an amino acid residue constituting a polyamino acid can be removed. Deprotection can be performed for a part of or all protecting groups contained in polyamino acid. Deprotection is performed as follows.

For example, an amino acid residue containing an ester group as a protecting group can be subjected to a saponification treatment, a hydrogenation reaction and the like to remove the ester group. An amino acid residue containing a carbamate group as a protecting group can be added with acid, base, hydrogen and the like to easily remove the carbamate group. Since the medical material of the present invention can be deprotected by treating the surface thereof with acid, base and the like as shown in the below-mentioned Examples, the deprotection in the present specification may sometimes be expressed as a "surface treatment" or a "treatment" with the compound used.

While the reaction reagent or solvent used for the removal of the protecting group is not particularly limited, examples of the reagent to be used for a saponification treatment of an ester group include basic inorganic compounds such as potassium hydroxide, sodium hydroxide, lithium hydroxide, cesium hydroxide, sodium hydride, sodium borohydride and the like; basic organic compounds such as diethylamine, triethylamine, triethylenediamine, N,N-diisopropylethylamine, pyridine, 1,8-bis(dimethylamino)naphthalene, histidine, diazabicycloundecene, diazabicyclononene and the like; enzyme and the like. As the solvent, organic solvents such as methanol, ethanol, 2-propanol, acetone, methylethyl ketone, tetrahydrofuran, diethyl ether, diisopropyl ether, petroleum ether, 1,4-dioxane, formamide, N,N-dimethylformamide, N,N-dimethylacetamide, N-methylpyrrolidone, dimethyl sulfoxide, acetonitrile, benzene, toluene, xylene, hexane, cyclohexane, ethyl acetate, butyl acetate, dichloromethane, chloroform, 1,2-dichloroethane and trichloroethane, or water can be used. For example, as the reagent used for the removal of side chain carbamate group, palladium black, 5-10% palladium carbon, hydrogen bromide/acetic acid, hydrogen bromide/trifluoromethanesulfonic acid, hydrogen fluoride, trifluoroacetic acid, hydrogen chloride, sodium/ammonia, triethylsilane, trichloroborane, trifluoroborane and the like can be mentioned, and UV irradiation can also remove the group. As the reaction solvent, organic acids such as formic acid, acetic acid, citric acid, oxalic acid and trifluoroacetic acid; organic solvents such as methanol, ethanol, 2-propanol, acetone, methylethyl ketone, tetrahydrofuran, diethyl ether, diisopropyl ether, petroleum ether, 1,4-dioxane, formamide, N,N-dimethylformamide, N,N-dimethylacetamide, N-methylpyrrolidone, dimethyl sulfoxide, acetonitrile, benzene, toluene, xylene, hexane, cyclohexane, ethyl acetate, butyl acetate, dichloromethane, chloroform, 1,2-dichloroethane and trichloroethane; or water can be used. In these reactions, the solvent may be one kind or two or more kinds.

In the present invention, polyamino acid after deprotection or polyamino acid before deprotection can also be further bonded with a protecting group. A protecting group can be bonded by changing the kind of the protecting group according to various amino acid residues in the same manner as above. A protecting group of a different kind from the protecting group before deprotection can also be bonded.

As a method for observing the bonding state of a protecting group to a polyamino acid, scanning electron microscope (SEM), transmission electron microscope (TEM), atom force microscope (AFM), X-ray photoelectron spectroscopy (XPS), Auger electron spectroscopy (AES), time-of-flight secondary ion mass spectrometry (TOF-SIMS) and the like can be generally used.

The medical material of the present invention characteristically contains the above-mentioned polyamino acid as a main component. In the present specification, the main component refers to a main component contained as a starting material of a medical material and the content thereof is generally not less than 60 wt %, preferably not less than 80 wt %, more preferably not less than 90 wt %, still more preferably not less than 95 wt %, most preferably 100 wt %, relative to the total weight of the medical material.

The medical material of the present invention can also contain two or more kinds of polyamino acids. While the combination of two kinds of polyamino acids is not particularly limited, a combination of a polyamino acid containing an alanine residue and a polyamino acid containing a lysine residue optionally containing a protecting group in the side chain is preferable. The mixing ratio of polyamino acid when, for example, two kinds of polyamino acids are used can be appropriately selected from 99:1-1:99, preferably 95:5-5:95, more preferably 90:10-10:90, in a molar ratio. Examples of the two kinds of polyamino acids include a combination of a polyamino acid constituted by an alanine residue and a polyamino acid constituted by a lysine residue optionally containing a protecting group in the side chain. Specifically, a mixture (9:1-6:4 in molar ratio) of poly-L-alanine and poly-$N^\varepsilon$-benzyloxycarbonyl-L-lysine, which is deprotected by HBr treatment and the like, is preferable.

The medical material of the present invention can contain, besides polyamino acid, a polymer compound other than polyamino acid. Examples of such polymer compound include polyvinyl chloride, polyacrylonitrile, polylactic acid, polyglycolic acid, polylactic acid-glycolic acid copolymer, polycaprolactone, polybutylenesuccinate, polyethylene succinate, polystyrene, polycarbonate, polyhexamethylenecarbonate, polyarylate, polyvinyl isocyanate, polybutyl isocyanate, polymethylmethacrylate, polyethylmethacrylate, polypropylmethacrylate, polybutylmethacrylate, polymethylacrylate, polyethylacrylate, polybutylacrylate, poly(ethylene terephthalate), poly(trimethylene terephthalate), poly(ethylene naphthalate), poly(paraphenylene terephthalamide), poly(paraphenylene terephthalamide-3,4'-oxydiphenylene terephthalamide) copolymer, poly(metaphenylene isophthalamide), cellulosediacetate, cellulosetriacetate, methylcellulose, propylcellulose, benzylcellulose, carboxycellulose, carboxymethylcellulose, oxidized regenerated cellulose, hyaluronic acid, sodium hyaluronate, fibroin, natural rubber, synthetic polymer compounds such as polyvinyl alcohol, polyvinyl acetate, polyvinyl methylether, polyvinyl ethylether, polyvinyl propylether, polyvinyl butylether, polyvinylidenechloride, poly-N-vinylpyrrolidone, poly-N-vinylcarbazole, poly-N-vinylpyridine, polyvinyl methylketone, polyvinyl isopropenylketone, polyethylene oxide, polypropyleneoxide, polycyclopenteneoxide, polystyrenesulfone, nylon 6, nylon 66, nylon 11, nylon 12, nylon 610, nylon 612 and the like and copolymers thereof, proteins such as collagen, atelocollagen, gelatin, laminin, fibronectin, sericin and the like, polysaccharides such as chitin, chitosan, cellulose and the like, and the like. Only one kind of these may be used or a combination of two or more kinds thereof may be used.

Of the polymer compounds exemplified in the above, polylactic acid, polyglycolic acid, poly(lactic acid-glycolic acid) copolymer, polycaprolactone, carboxymethylcellulose, oxidized regenerated cellulose, hyaluronic acid, sodium hyaluronate, polyvinyl alcohol, collagen, atelocollagen, gelatin, laminin, fibronectin, sericin, chitin, chitosan, cellulose can be preferably used since they maintain or improve the strength and/or shape of the medical material of the present invention. More preferably, polylactic acid, polyglycolic acid, poly(lactic acid-glycolic acid) copolymer, carboxymethylcellulose, oxidized regenerated cellulose, sodium hyaluronate, polyvinyl alcohol, collagen and gelatin can be used. Only one kind of these may be used or a combination of two or more kinds thereof may be used.

While the aforementioned polymer compound is appropriately determined according to the use and the like of the medical material of the present invention, it is generally 1-40 wt %, preferably 0.1-20 wt %, more preferably 1-10 wt %, still more preferably 1-5 wt %, relative to the total weight of the medical material. When the ratio of the polymer compound is higher than the upper limit of the above-mentioned range, the cell differentiation promotion function or property of the medical material based on the polyamino acid tends to be impaired, and when the ratio is lower than the lower limit of the above-mentioned range, the effect of addition of a polymer compound is difficult to find.

While the medical material of the present invention is not particularly limited as long as the effect of the invention can be afforded, it can be formed as, for example, a fiber structure. The fiber structure is constituted by nanofiber having an average fiber diameter of not less than 50 nm, preferably not less than 100 nm, more preferably not less than 150 nm, still more preferably not less than 200 nm and less than 1,500 nm, preferably less than 1,000 nm, more preferably less than 500 nm. The average fiber diameter of the fiber structure can be measured by a method known to those of ordinary skill in the art. To be specific, any 10 points are selected on the photographs of the surface of fiber structures randomly taken by a scanning electron microscope, the diameter of the fibers was measured and the average value thereof is taken as an average fiber diameter. Photographs of the fiber structures taken with 500-200,000× magnification can be used. In the present invention, more specifically, the average fiber diameter of the fiber structure can be measured according to the below-mentioned Examples.

In the present specification, the fiber structure refers to a structure formed with singular or plural fibers, and examples of the form thereof include filament, staple, filament yarn, spun yarn, fabric, knitted fabric, non-woven fabric, paper, sheet-like object, tube, mesh, thread-like object and the like. In the present invention, the form of a preferable fiber structure is non-woven fabric.

The polyamino acid to be contained in a fiber structure is as mentioned above, and is preferably constituted by 1-3 kinds of amino acid residues. When polyamino acid is constituted by one kind of amino acid residue, said amino acid residue is not particularly limited as long as it is an amino acid residue shown above, and is preferably an alanine residue, a leucine residue, a valine residue, an aspartic acid residue optionally containing a protecting group in the side chain, a lysine residue optionally containing a protecting group in the side chain, or a glutamic acid residue optionally containing a protecting group in the side chain. When polyamino acid is constituted by two kinds of amino acid residues, one of the two kinds of amino acid residues is not particularly limited as long as it is an amino acid residue shown above, and is preferably a lysine residue optionally containing a protecting group in the side chain, a glutamic acid residue optionally containing a protecting group in the side chain, or a phenylalanine residue.

When one of the two kinds of amino acid residues is the aforementioned lysine residue, the other kind is not particularly limited, and is preferably an alanine residue, a valine residue, a leucine residue, an isoleucine residue or a phenylalanine residue. That is, the combination of the two kinds of amino acid residues is a lysine residue optionally containing a protecting group in the side chain and an alanine residue, a lysine residue optionally containing a protecting group in the side chain and a valine residue, a lysine residue optionally containing a protecting group in the side chain and a leucine residue, a lysine residue optionally containing a protecting group in the side chain and an isoleucine residue, or a lysine residue optionally containing a protecting group in the side chain and a phenylalanine residue.

When one of the two kinds of amino acid residues is the aforementioned glutamic acid residue, the other kind is not particularly limited, and is preferably an alanine residue, a leucine residue, a valine residue, an isoleucine residue, or a phenylalanine residue. That is, the combination of the two kinds of amino acid residues is a glutamic acid residue optionally containing a protecting group in the side chain and an alanine residue, a glutamic acid residue optionally containing a protecting group in the side chain and a leucine residue, a glutamic acid residue optionally containing a protecting group in the side chain and a valine residue, a glutamic acid residue optionally containing a protecting group in the side chain and an isoleucine residue, or a glutamic acid residue optionally containing a protecting group in the side chain and a phenylalanine residue.

When one of the two kinds of amino acid residues is a phenylalanine residue, the other kind is not particularly limited, and is preferably a leucine residue or a valine residue. That is, the combination of the two kinds of amino acid residues is a phenylalanine residue and a leucine residue, or a phenylalanine residue and a valine residue.

When polyamino acid is constituted by 3 kinds of amino acid residues, it is not particularly limited, but a phenylalanine residue/aspartic acid residue optionally containing a protecting group in the side chain/glutamic acid residue optionally containing a protecting group in the side chain, a phenylalanine residue/aspartic acid residue optionally containing a protecting group in the side chain/lysine residue optionally containing a protecting group in the side chain, or a leucine residue/glutamic acid residue optionally containing a protecting group in the side chain/lysine residue optionally containing a protecting group in the side chain is preferable.

When the protecting group content of polyamino acid is adjusted, indication of an aspartic acid residue, lysine residue or glutamic acid residue having a protecting group in the side chain encompasses the existence of an aspartic acid residue, lysine residue or glutamic acid residue free of a protecting group in parts thereof, as in the above.

A fiber structure is produced by electrospinning using an electrospinning apparatus. Examples of the electrospinning apparatus include a nanofiber electrospinning unit (NEU) of KATO TECH CO., LTD., which is provided with a syringe, a nozzle (needle), a syringe pump, a high voltage generator and a collector.

When the medical material of the present invention is a fiber structure, the production method of the fiber structure characteristically includes the following steps:
step 1) a step of dissolving polyamino acid in a solvent to give a solution,
step 2) a step of continuously discharging the aforementioned solution charged in a syringe from a nozzle set at the tip of a syringe,
step 3) a step of applying a high voltage between a nozzle and a collector by a high voltage generator during the aforementioned discharge,
step 4) a step of changing the aforementioned discharged solution into the shape of a fiber between the nozzle and the collector,
step 5) a step of collecting the fiber on a collector.

While the concentration of the polyamino acid in the solution in step 1 is appropriately determined depending on the kind of the polyamino acid to be used, the kind of the solvent to dissolve the polyamino acid and the like, it can be set to generally 0.1-60 wt %, preferably 1-45 wt %, more preferably 1-20 wt %. When the concentration of the polyamino acid is higher than the above-mentioned range, the viscosity of the solution tends to become high and spinning tends to be defective. When the concentration is lower than the above-mentioned range, the production of the fiber structure requires a significant time. When two or more kinds of polyamino acids are used, a solution only needs to be prepared by dissolving an appropriate mixture of various polyamino acids. The mixing ratio of polyamino acid when, for example, two kinds of polyamino acids are used can be set to 95:5-5:95, preferably 90:10-10:90, in a weight ratio.

The solvent used to dissolve polyamino acid to be used in step 1 in the present invention is not particularly limited as long as it dissolves polyamino acid and is easily removed by evaporation and the like in the fiber forming step. Examples thereof include acetone, methylethyl ketone, methylisobutylketone, cyclohexanone, methanol, ethanol, 2-propanol, tetrahydrofuran, diethyl ether, petroleum ether, 1,4-dioxane, benzene, toluene, xylene, hexane, cyclohexane, ethyl acetate, butyl acetate, trifluoroacetic acid, acetic acid, formic acid, dichloromethane, chloroform, carbon tetrachloride, dichloroethane, trichloroethane, trichloroethylene, trifluoroethane, 1,1,1,3,3,3-hexafluoro-2-propanol, 2,2,2-trifluoroethanol, hexafluoroacetone, formamide, N,N-dimethylformamide, N,N-dimethylacetamide, N-methylpyrrolidone, pyridine, acetonitrile, water and the like.

Since the average fiber diameter of the obtained fiber structure can be controlled, trifluoroacetic acid, acetic acid, dichloromethane, chloroform, carbon tetrachloride, 1,2-dichloroethane, trichloroethane, trichloroethylene, trifluoroethane, 1,1,1,3,3,3-hexafluoro-2-propanol, 2,2,2-trifluoroethanol, N,N-dimethylformamide and water are preferable, and trifluoroacetic acid, acetic acid, dichloromethane, chloroform, 1,2-dichloroethane, 1,1,1,3,3,3-hexafluoro-2-propanol, 2,2,2-trifluoroethanol, N,N-dimethylformamide and water are more preferable. Only one kind of these may be used or a combination of two or more kinds thereof may be used.

For dissolution of polyamino acid in step 1, as necessary, a method such as heating, use of an ultrasonication apparatus, addition of solubilizer and the like can be employed. Specific examples of the solubilizer can include alkali metal salts such as sodium salt, potassium salt and the like, alkaline earth metal salts such as magnesium salt, calcium salt and the like, inorganic bases such as ammonia and the like, organic amines such as monoethanolamine, diethanolamine, triethanolamine, 2-amino-2-methyl-1-propanol, 2-amino-2-methyl-1,3-propanediol, lysine, ornithine, arginine and the like, inorganic acids such as hydrochloric acid, sulfuric acid, phosphoric acid and the like, and organic acids such as tartaric acid, citric acid, p-toluenesulfonic acid, glycolic acid, malic acid, lactic acid, fatty acid, acidic amino acid, pyroglutamic acid and the like. Only one kind of these may be used or a combination of two or more kinds thereof may be used.

The discharge rate of the polyamino acid solution in step 2 can be appropriately set according to the viscosity of the solution to be discharged, the scale of the electrospinning apparatus and the like. It can be generally 0.1-60 ml/hour, preferably 1-20 ml/hour. When the discharge rate is faster than the above-mentioned range, the discharged solution in a droplet state tends to reach the collector, and cause fusion of fibers and the like. When the discharge rate is slower than the above-mentioned range, the production of a fiber structure requires a significant time.

In step 2, the solution may be discharged from one or more nozzles, and therefore, the solution may be discharge from one site or two or more sites. When the discharge of the solution is prevented in step 2 since the discharge opening of the nozzle is blocked by the attachment of the fiber formed in step 4, precipitation of a solid from the discharge solution in step 2 and the like, prevention of discharge of the solution can be avoided by discharge while removing such attachments, precipitates and the like by a suitable method.

The voltage to be applied in between the nozzle and collector in step 3 is appropriately determined according to the viscosity of the solution to be discharged, scale of the electrospinning apparatus and the like, and can be generally 5-50 kV, preferably 11-45 kV. In the present invention, the voltage can be set to not less than 11 kV, preferably not less than 13 kV, more preferably not less than 15 kV, further preferably not less than 17 kV, particularly preferably not less than 19 kV. In addition, the voltage can be set to not more than 45 kV, preferably not more than 40 kV, more preferably not more than 35 kV, further preferably not more than 30 kV, particularly preferably not more than 25 kV. When the voltage to be applied is higher than the above-mentioned range, a risk of electrical discharge between the nozzle and collector occurs. When the voltage to be applied is lower than the above-mentioned range, the fiber diameter does not become small and spinnability tends to be defective.

The distance between the nozzle and collector in step 4 is appropriately determined according to the scale of the electrospinning apparatus and the like, and can be generally 5-50 cm, preferably 10-40 cm. In the present invention, the distance can be set to not less than 10 cm, preferably not less than 12 cm, more preferably not less than 14 cm, further preferably not less than 16 cm, particularly preferably not less than 18 cm, and can be set to not more than 40 cm, preferably not more than 35 cm, more preferably not more than 30 cm, further preferably not more than 25 cm, particularly preferably not more than 20 cm. When the distance is longer than the above-mentioned range, the formed fiber does not reach the collector and attaches to the site between the nozzle and collector. When the distance is shorter than the above-mentioned range, the discharged solution in a droplet state directly reaches the collector, and tends to cause fusion of the fibers and the like.

The fiber structure formed on the collector in step 5 can be subjected to an operation such as neutralization, drying and the like as necessary. For example, when an organic acid is used as a solvent or solubilizer to dissolve polyamino acid used in the present invention, the organic acid remaining in the fiber structure can be neutralized by a method such as immersing in an aqueous alkali solution such as sodium hydroxide, potassium hydroxide, sodium bicarbonate and the like, spraying an aqueous alkali solution, leaving in saturated ammonia vapor and the like. When the polyamino acid used in the present invention is dissolved in a solvent with low volatility, the solvent remaining in the fiber structure can be removed by a method such as heating, blowing dry air, leaving in vacuum or under reduced pressure and the like.

The thickness of the fiber structure formed on a collector in step 5 may be any depending on the use thereof. For example, it is about 1-100 μm when the fiber structure is used as a scaffold for tissues and cells, and about 50-100 μm when the fiber structure is used as an artificial skin.

The temperature and humidity for electrospinning in steps 1-5 are appropriately determined according to the kind of the solvent that dissolves polyamino acid to be used in the present invention and the like, and are generally adjusted to 5-30° C. and relative humidity 10-80%.

The nozzles used in steps 1-5 may have any shape and size as long as they can discharge the solution in step 2 and can be an electrode upon application of a high voltage in step 3. For example, an injection needle can be mentioned. The diameter of an injection needle used for electrospinning including steps 1-5 can generally be 0.01-2.0 mm, preferably 0.1-1.5 mm. When the diameter of an injection needle is larger than the above-mentioned range, the discharged solution in a droplet state highly tends to reach the collector. When the diameter is smaller than the above-mentioned range, the production of a fiber structure requires a significant time due to the small discharge rate per hour.

The collectors to be used in steps 1-5 may have any shape and size as long as they have a metal with good conductivity such as copper, aluminum, stainless steel and the like, and can be an electrode when a high voltage is applied in step 3. For example, by forming the collector as a cylindrical rotating body, a membranous, tubular or hollow fiber structure can be obtained. Furthermore, for easy detachment of the fiber structure from the collector, for example, aluminum foil, spun bond non-woven fabric, gauze, micronanofiber sheet and the like, which does not impair the function as an electrode of the collector, may be placed on the collector and a fiber structure may be formed thereon.

The medical material of the present invention can also be formed as a film. The film has a thickness of not less than 0.1 μm, preferably not less than 1 μm, more preferably not less than 10 μm, and not more than 250 μm, preferably not more than 200 μm, more preferably not more than 100 μm. In the present specification, the film refers to a thin membranous formed member, which can exist as a solid by itself. The film may also be used alone, or may be used in combination with a solid-phase support made of plastic and the like by being in contact with the surface of the support. The thickness of the film can be measured by a method known to those of ordinary skill in the art. To be specific, a conventional film thickness meter, transmission infrared film thickness meter or specular reflection infrared film thickness meter can be used, and the measurement device can be purchased from Mitsutoyo Corporation, SEIKO EM, KURABO INDUSTRIES LTD., Yokogawa Electric Corporation and the like.

The polyamino acid to be contained in the film is as mentioned above, and is preferably constituted by 1-3 kinds of amino acid residues. When polyamino acid is constituted by one kind of amino acid residue, the amino acid residue is not particularly limited as long as it is amino acid residue shown above, and is preferably constituted by a valine residue, or a glutamic acid residue optionally containing a protecting group in the side chain. When polyamino acid is constituted by two kinds of amino acid residues, one of the two kinds of amino acid residues is not particularly limited as long as it is an amino acid residue shown above, and is preferably a glutamic acid residue optionally containing a protecting group in the side chain, a lysine residue, or a phenylalanine residue.

When one of the two kinds of amino acid residues is the aforementioned glutamic acid residue, the other kind is not particularly limited, and is preferably a valine residue, an isoleucine residue, or a glutamic acid residue optionally containing a protecting group in the side chain. That is, the combination of the two kinds of amino acid residues is a glutamic acid residue optionally containing a protecting group in the side chain and a valine residue, or a glutamic acid residue optionally containing a protecting group in the side chain and an isoleucine residue.

When one of the two kinds of amino acid residues is the aforementioned lysine residue, the other kind is not particularly limited, and is preferably an alanine residue, a valine residue, or an isoleucine residue. That is, the combination of the two kinds of amino acid residues is a lysine residue optionally containing a protecting group in the side chain and an alanine residue, a lysine residue optionally containing a protecting group in the side chain and a valine residue, a lysine residue optionally containing a protecting group in the side chain and an isoleucine residue.

When one of the two kinds of amino acid residues is a phenylalanine residue, the other kind is not particularly limited, and is preferably a valine residue. That is, the combination of the two kinds of amino acid residues is a phenylalanine residue and a valine residue.

When polyamino acid is constituted by 3 kinds of amino acid residues, it is not particularly limited, and is preferably a phenylalanine residue/aspartic acid residue optionally containing a protecting group in the side chain/glutamic acid residue optionally containing a protecting group in the side chain, or a phenylalanine residue/aspartic acid residue optionally containing a protecting group in the side chain/lysine residue optionally containing a protecting group in the side chain.

When the protecting group content of polyamino acid is adjusted, indication of an aspartic acid residue, glutamic acid residue or lysine residue having a protecting group in the side chain encompasses the existence of an aspartic acid residue, glutamic acid residue or lysine residue free of a protecting group in parts thereof, as in the above.

While the production method of the film of polyamino acid used in the present invention is not particularly limited, for example, a solution-cast film-forming method is used. Specifically, a dope containing polyamino acid and a solvent is cast on a support to form a cast film as described in JP-A-2008-1074. The cast film is dried on the support to confer self-supporting property, detached from the support and subjected to a drying step as necessary. While the concentration of the polyamino acid in this case is appropriately set according to the kind of the polyamino acid to be used, the kind of the solvent used to dissolve the polyamino acid, and the like, it is generally 0.1-60 wt %. When two or more kinds of polyamino acids are used, a solution is prepared by dissolving an appropriate mixture of various polyamino acids. As the production method of the film besides those mentioned above, a melt extrusion molding method, a calendar method and the like can also be utilized. Examples of the melt extrusion molding method include inflation method, T-die method and the like. The film can be processed into a shape having plural layers superimposed on top of each other by a method such as co-extrusion method, lamination method, heat sealing and the like.

The solvent used to dissolve polyamino acid is not particularly limited as long as it dissolves polyamino acid and is easily removed by evaporation and the like in the film forming step. Examples thereof include acetone, methylethyl ketone, methylisobutylketone, cyclohexanone, methanol, ethanol, 2-propanol, tetrahydrofuran, diethyl ether, petroleum ether, 1,4-dioxane, benzene, toluene, xylene, hexane, cyclohexane, ethyl acetate, butyl acetate, trifluoroacetic acid, acetic acid, formic acid, dichloromethane, chloroform, carbon tetrachloride, dichloroethane, trichloroethane, trichloroethylene, trifluoroethane, 1,1,1,3,3,3-hexafluoro-2-propanol, 2,2,2-trifluoroethanol, hexafluoroacetone, formamide, N,N-dimethylformamide, N,N-dimethylacetamide, N-methylpyrrolidone, pyridine, acetonitrile, phosphate buffer, water and the like.

The medical material of the present invention can also be formed as a coating. In the present specification, coating refers to a film coating the surface of a material used for general products, which cannot be present solely as a solid since the film itself does not have a supporting force. Examples of the material used for general products include glass, cloth (fiber), metal, plastic and the like. The coating has a thickness of not less than 0.1 µm, preferably not less than 1 µm, more preferably not less than 10 µm, and not more than 250 µm, preferably not more than 200 µm, more preferably not more than 100 µm. The thickness thereof can be measured by a method known to those of ordinary skill in the art. To be specific, it can be measured using a general film thickness meter, infrared film thickness meter, ultrasonic thickness meter, electromagnetic guidance film thickness meter, eddy-current film thickness meter and the like, and the measurement device can be purchased from Mitsutoyo Corporation, MK Scientific, Inc., ROINOS, KURABO INDUSTRIES LTD., GE Inspection Technologies and the like.

The coating can be obtained by dissolving polyamino acid in a solvent, applying the solution to the surface of a solid-phase support such as glass, plastic and the like, and drying same. The solvent used to dissolve the polyamino acid is not particularly limited as long as it dissolves the polyamino acid and permits smooth application. Examples thereof include acetone, methylethyl ketone, methylisobutylketone, cyclohexanone, methanol, ethanol, 2-propanol, tetrahydrofuran, diethyl ether, petroleum ether, 1,4-dioxane, benzene, toluene, xylene, hexane, cyclohexane, ethyl acetate, butyl acetate, trifluoroacetic acid, acetic acid, formic acid, dichloromethane, chloroform, carbon tetrachloride, dichloroethane, trichloroethane, trichloroethylene, trifluoroethane, 1,1,1,3,3,3-hexafluoro-2-propanol, 2,2,2-trifluoroethanol, hexafluoroacetone, formamide, N,N-dimethylformamide, N,N-dimethylacetamide, N-methylpyrrolidone, pyridine, acetonitrile, phosphate buffer, water and the like.

The solution dissolving the polyamino acid can be applied to the surface of a solid-phase support by any method such as spin coating method, dip coating method, drop casting method, spray coating method, ink jet method, screen printing method, contact printing method such as stamp, inline coating method, offline coating method, roll coating method, gravure coating method, microgravure coating method, reverse coating method, reverse gravure coating method, bar coating method, roll brush method, air-knife coating method, curtain coating method, die coating method and the like. These application methods can be used alone or in combination. For example, when the bar coating method is used, a thin film can be produced by dropping the prepared solution on a solid-phase support, extending same with a bar coater and finally drying.

After application of a solution dissolving a polyamino acid, a particular operation for promoting drying can also be performed where necessary. While the drying operation is appropriately determined according to the kind of the polyamino acid to be used, the kind of the solvent dissolving the polyamino acid and the like, it is generally performed by air drying, blowing dry air, leaving under vacuum or reduced pressure, and the like. The temperature in this case is generally about at room temperature –-100° C.

The polyamino acid to be contained in a coating is as mentioned above, and is preferably constituted by 1-3 kinds of amino acid residues. When polyamino acid is constituted by one kind of amino acid residue, the amino acid residue is not particularly limited as long as it is an amino acid residue shown above, and a glycine residue, or a lysine residue optionally containing a protecting group in the side chain is preferable. When polyamino acid is constituted by two kinds of amino acid residues, one of the two kinds of amino acid residues is not particularly limited as long as it is an amino acid residue shown above, and is preferably a lysine residue optionally containing a protecting group in the side chain.

When one of the two kinds of amino acid residues is the aforementioned lysine residue, the other kind is not particularly limited, and is preferably an alanine residue, a phenylalanine residue, or a lysine residue optionally containing a protecting group in the side chain. That is, the combination of the two kinds of amino acid residues is a lysine residue optionally containing a protecting group in the side chain and an alanine residue, or a lysine residue optionally containing a protecting group in the side chain and a phenylalanine residue.

When the polyamino acid is constituted by 3 kinds of amino acid residues, it is not particularly limited, and a leucine residue/glutamic acid residue optionally containing a protecting group in the side chain/lysine residue optionally containing a protecting group in the side chain is preferable.

When the protecting group content of polyamino acid is adjusted, indication of an aspartic acid residue, glutamic acid residue or lysine residue having a protecting group in the side chain encompasses the existence of an aspartic acid residue, glutamic acid residue or lysine residue free of a protecting group in parts thereof, as in the above.

The medical material of the present invention may be subjected to a surface modification. Particularly, when the medical material is used in the field of regenerative medicine, it is preferably subjected to a surface modification in view of frequent contact with various materials and influence from the surface during cell culture, incorporation into a cell scaffold, culture in a bioreactor and the like. The surface modification can be classified into physical surface modification, physicochemical surface modification, and chemical surface modification. The physical surface modification includes coating with biomolecule or polymer, shape modification such as honeycomb processing, porosification and the like, and the like. The physicochemical surface treatment includes UV treatment, high-pressure discharge treatment, gamma-ray irradiation treatment, ion beam treatment, plasma treatment and the like. The chemical surface modification includes immobilization of biomolecules such as peptide, protein and the like, modification of polymer surface functional group, polymer grafting, blending, crystallization, amorphization, phase separation such as patterning and the like, and the like.

While the medical material of the present invention is not particularly limited, it is preferably used as a substrate for the regeneration of biological tissues or cells regeneration in the field of regenerative medicine. For example, it can be utilized for scaffold for tissue regeneration, suture thread for surgery, suture stiffener, stent, fixation material for fractured bone, artificial ligament, wound coating material, artificial dura mater, artificial blood vessel, artificial basal lamina, artificial extracellular matrix, medical adhesive, medical jointing material, drug supporting substrate, drug delivery (DDS) substrate, totipotent or pluripotent stem cells such as iPS cell and ES cell, supporting substrate for differentiation induction of other various stem cells and the like. The medical material of the present invention may be used alone or in combination with other medical materials, pharmaceutical products, cell for treatment, stem cell and the like. When the medical material of the present invention is transferred to the body of a mammal (e.g., human), the differentiation of the cells (e.g., mesenchymal stem cell) is promoted in the site of transfer of the medical material, and therefore, the effects of early repair of invaded area and the like can be expected.

Since the medical material of the present invention contains polyamino acid as a main component, it can be easily degraded in the live body. Particularly, when the medical material is a fiber structure, the fiber structure can be more easily degraded in the live body, since its fiber diameter is of the same level as that of extracellular matrix in vivo. Therefore, the medical material of the present invention is preferable for a scaffold desired to rapidly disappear after repair or regeneration of biological tissues and cells in the live body. In the present specification, the scaffold refers to a substrate for regeneration of biological tissues or cells in the field of regenerative medicine, which is a formed member capable of functioning as a biological material aiming to repair, regenerate or treat a defective biological tissue.

The medical material of the present invention can be formed into a shape or structure corresponding to the defective biological tissue or cell parts, and directly or indirectly used to repair, regenerate or treat the skin, blood vessel, nerve, bone, joint, esophagus, valve, other organ and the like. It is also possible to add various medicaments such as cell growth factor, cell adhesion factor, cell differentiation factor, anti-inflammatory agent, antiallergic agent, antitumor agent, vitamins and the like to the material of cell scaffold or the scaffold.

In addition, cell differentiation can be promoted by cell culture using the medical material of the present invention in vitro to contact the cells (e.g., undifferentiated cell) with a surface of the medical material of the present invention.

The cell to be the target of differentiation promotion is not particularly limited as long as it can be differentiated by culture. Examples thereof include embryonic stem cells (ES cell), embryonic carcinoma cell (EC cell), embryonic germ stem cell (EG cell), nuclear transfer ES cell (ntES cell), induced pluripotent stem cell (iPS cell), neural stem cell, hematopoietic stem cell, mesenchymal stem cell, liver stem cell, pancreatic stem cell, skin stem cell, muscle stem cell, reproductive stem cell and the like. Mesenchymal stem cell is preferably used.

While the method is not particularly limited, ex vivo use is preferable, and the method can contain a step of contacting a cell with a surface of the above-mentioned medical material and a step of cultivating the cell. The cell to be the target of contact is not particularly limited, and the cells similar to those exemplified above can be used.

While the method of contacting the cell is not particularly limited as long as the cell can be cultured thereafter and in the condition for differentiation, for example, it can be performed by preparing a suspension of the cells in a liquid medium and the like and adding the obtained solution to a vessel and the like containing the above-mentioned medical material.

The medium for cultivating the cell is appropriately selected according to the kind of the cell to be used and can be prepared using a medium used for culture of animal cells as a basal medium. The basal medium is not particularly limited as long as it can be used for culturing animal cells, for example, DMEM medium, MEM medium, BME medium, DME medium, α-MEM medium, IMEM medium, ES medium, DM-160 medium, Fisher medium, F12 medium, WE medium, RPMI medium, StemSpan medium, StemPro medium, a mixed medium thereof and the like. The medium can also be a serum-containing medium or serum-free medium. The serum-free medium means a medium without containing an unadjusted or unpurified serum, and a medium contaminated with a purified blood-derived component and an animal tissue-derived component (e.g., growth factor) is considered to fall under the serum-free medium. Furthermore, the medium can contain a cytokine and a cell growth factor as additive as necessary. The presence of cytokine and cell growth factor can further increase the cell proliferation rate and cell activity. Specific examples thereof include erythropoietin, granulocyte colony stimulating factor (G-CSF), stem cell factor, Flk2/Flk3 ligand, thrombopoietin, soluble interleukin-6 receptor, interleukin-3 and the like.

The cell culture conditions can be appropriately determined according to the medium to be used. For example, while the culture temperature is not particularly limited, it is about 30-40° C., preferably about 37° C. The $CO_2$ concentration is, for example, about 1-10%, preferably about 2-7%. The culture period can be about 1 week or more, including subculturing several times, preferably resulting in about 3-5 weeks.

According to this method, the cells after culture and growth of the colony to a certain size can also be subcultured on feeder cells. Examples of the feeder cell include fibroblasts after termination of cell division by a treatment with radiation or antibiotic (e.g., mouse embrionic fibroblast (MEF)) and the like. As the MEF, for example, STO cell, SNL cell (McMahon, A. P. & Bradley, A. Cell 62: 1073-1085 (1990)) and the like can be used.

In this method, the above-mentioned medical material may be directly used, or processed into a suitable form before use, or immobilized on the surface of a substrate other than the medical material by coating, applying, and the like before use. Particularly, when the medical material of the present invention is a coating, it can be easily applied to the surface of the aforementioned substrate. As the material to be used as the substrate, a material used for medical purposes is preferable, and examples thereof include polyvinyl chloride; cellulose polymer, polystyrene, polymethylmethacrylate, polycarbonate, polysulfone, polyurethane, polyester, polyamide, polyethylene, polypropylene, polyester, hydroxyapatite, calcium carbonate, titanium oxide, titanium, tantalum, zirconia, alumina, silica and the like.

Whether or not the cell differentiation is promoted can be examined by, though subject changes depending on the kind of the cell to be used and the cell after differentiation, adding a medium on the surface of the above-mentioned medical material or a substrate coated with the medical material, performing cell culture for a given period (e.g., 10-40 days), and measuring a marker generally used for differentiated cells. To be specific, it can be examined as shown in the below-mentioned Examples.

In the present invention, the property relating to the cell adhesion can be varied within the range associated with a cell differentiation promoting effect, by controlling the kind, composition or protecting group content of the amino acid residue of the above-mentioned polyamino acid. To be specific, a medical material having a cell adhesion suppressive effect or cell adhesion effect, as well as a cell differentiation promoting effect, can be provided.

For obtaining a medical material superior to adhesion suppressive effect to cell and biological tissue, the polyamino acid contained in the medical material of the present invention can be constituted by one or two kinds of amino acid residue. When polyamino acid is constituted by one kind of amino acid residue, said amino acid residue is not particularly limited as long as it is an amino acid residue shown above, and can be an alanine residue, a leucine residue, a valine residue, an aspartic acid residue optionally containing a protecting group in the side chain, or a lysine residue optionally containing a protecting group in the side chain. In addition, when polyamino acid is constituted by two kinds of amino acid residues, one of the two kinds of amino acid residues is not particularly limited as long as it is an amino acid residue shown above, and can be a lysine residue optionally containing a protecting group in the side chain, a glutamic acid residue optionally containing a protecting group in the side chain, or a phenylalanine residue. In this case, the medical material of the present invention can be a fiber structure.

When one of the two kinds of amino acid residues is the aforementioned lysine residue, the other kind is not particularly limited, and can be an alanine residue, a valine residue, or an isoleucine residue. That is, the combination of the two kinds of amino acid residues is a lysine residue optionally containing a protecting group in the side chain and an alanine residue, a lysine residue optionally containing a protecting group in the side chain and a valine residue, or a lysine residue optionally containing a protecting group in the side chain and an isoleucine residue. In this case, the medical material of the present invention can be a fiber structure.

When one of the two kinds of amino acid residues is the aforementioned glutamic acid residue, the other kind is not particularly limited, and can be an alanine residue, a leucine residue, a valine residue, an isoleucine residue, a phenylalanine residue or a glutamine residue. That is, the combination of the two kinds of amino acid residues is a glutamic acid residue optionally containing a protecting group in the side chain and an alanine residue, a glutamic acid residue optionally containing a protecting group in the side chain and a valine residue, or an isoleucine residue optionally containing a protecting group in the side chain. In this case, the medical material of the present invention can be a fiber structure.

When one of the two kinds of amino acid residues is a phenylalanine residue, the other kind is not particularly limited and can be a valine residue. That is, the combination of the two kinds of amino acid residues is a phenylalanine residue and a valine residue. In this case, the medical material for the present invention can be a fiber structure.

When the protecting group content of polyamino acid is adjusted, indication of an aspartic acid residue, lysine residue or glutamic acid residue having a protecting group in the side chain encompasses the existence of an aspartic acid residue, lysine residue or glutamic acid residue free of a protecting group in parts thereof, as in the above.

While the above-mentioned polyamino acid is not particularly limited, specific examples thereof include poly-L-alanine, poly-L-leucine, poly-L-valine, poly-β-benzyl-L-aspartic acid, poly-N$^\epsilon$-benzyloxycarbonyl-L-lysine, poly-L-alanine/γ-methyl-L-glutamic acid (9/1-6/4), poly-L-leucine/γ-methyl-L-glutamic acid (9/1-6/4), poly-L-valine/γ-methyl-L-glutamic acid (6/4), poly-L-isoleucine/γ-methyl-L-glutamic acid (6/4), poly-L-phenylalanine/γ-methyl-L-glutamic acid (9/1-6/4), poly-L-alanine/N$^\epsilon$-benzyloxycarbonyl-L-lysine (9/1-3/7), poly-L-valine/N$^\epsilon$-benzyloxycarbonyl-L-lysine (6/4), poly-L-isoleucine/N$^\epsilon$-benzyloxycarbonyl-L-lysine (6/4), poly-L-valine/L-phenylalanine (1/1), poly-L-glutamine/γ-methyl-L-glutamic acid, poly-γ-(methyl/polyethylene glycol)-L-glutamic acid, or poly-L-alanine/L-lysine is preferable, poly-L-alanine, poly-L-leucine, poly-L-valine, poly-β-benzyl-L-aspartic acid, poly-N$^\epsilon$-benzyloxycarbonyl-L-lysine, poly-L-alanine/γ-methyl-L-glutamic acid (9/1-6/4), poly-L-valine/γ-methyl-L-glutamic acid (6/4), poly-L-isoleucine/γ-methyl-L-glutamic acid (6/4), poly-L-alanine/N$^\epsilon$-benzyloxycarbonyl-L-lysine (9/1), poly-L-valine/N$^\epsilon$-benzyloxycarbonyl-L-lysine (6/4), poly-L-isoleucine/N$^\epsilon$-benzyloxycarbonyl-L-lysine (6/4), poly-L-valine/L-phenylalanine (1/1), poly-γ-(methyl/polyethylene glycol)-L-glutamic acid, or poly-L-alanine/L-lysine is more preferable, and poly-L-alanine, poly-L-leucine, poly-L-valine, poly-L-alanine/γ-methyl-L-glutamic acid (9/1-6/4), poly-L-isoleucine/γ-methyl-L- glutamic acid (6/4), poly-L-alanine/N$^\epsilon$-benzyloxycarbonyl-L-lysine (9/1), poly-L-valine/N$^\epsilon$-benzyloxycarbonyl-L-lysine (6/4), and poly-L-alanine/L-lysine.

A medical material having the above-mentioned cell adhesion suppressive effect is useful as, for example, a cell coagulation (spheroid) forming substrate.

With the effect shown above, the present invention can also provide a method of suppressing adhesion between cells, adhesion between a cell and a biological tissue, adhesion between biological tissues, adhesion between a cell or biological tissue and a solid substance, which uses the above-mentioned medical material containing, as a main component, polyamino acid having an amino acid residue. Use of such medical material enables promotion of cell differentiation while suppressing cell adhesion.

The method can contain a step of transplanting the above-mentioned medical material to a subject in need thereof. For the transplantation, the medical material is preferably inserted between the substances to be the target of adhesion suppression. Specifically, it can be placed at a position that prevents adhesion of a biological tissue being regenerated in an affected part to other tissues, or used to cover the surface of the solid substance so that the adhesion of a solid substance such as artificial organ and the like to a biological tissue can be prevented. While the target to be applied with the above-mentioned medical material is not particularly limited, mammals (e.g., human, mouse, rat, monkey, dog, bovine, horse, swine, sheep, goat, rabbit, hamster etc.) are preferable.

While the cell or biological tissue to be the target of adhesion suppression is not particularly limited, it can be, for example, any cell of mammals (e.g., human, mouse, rat, monkey, dog, bovine, horse, swine, sheep, goat, rabbit, hamster etc.) [for example, hepatocyte, splenocyte, nerve cell, glial cell, pancreatic β cell, bone marrow cell, mesangial cell, Langerhans cell, epidermal cell, epithelial cell, goblet cell, endothelial cell, smooth muscle cell, fibroblast, fibre cell, muscle cell, adipocyte, synovial cell, chondrocyte, osteocyte, osteoblast, osteoclast, mammary cell, hepatocyte or interstitial cell, or progenitor cell, stem cell, cancer cell etc. of these cells] or any tissue wherein these cells are present [for example, brain, each part of brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid gland, gall bladder, bone marrow, adrenal gland, skin, lung, gastrointestinal tract (e.g., large intestine, small intestine), blood vessel, heart, thymus, spleen, submandibular gland, peripheral blood, prostate, orchis, ovary, placenta, uterus, bone, articular, adipose tissue (e.g., brown adipose tissue, white adipose tissue), skeletal muscle etc.].

In this method, the above-mentioned medical material may be directly used, or processed into a suitable form before use, or immobilized on the surface of a substrate other than the medical material by coating, application, and the like before use. Particularly, when the above-mentioned medical material is a coating, it can be easily applied to the surface of the aforementioned substrate. As the material to be used as the substrate, a material used for medical purposes is preferable and examples thereof include polyvinyl chloride, cellulose polymer, polystyrene, polymethylmethacrylate, polycarbonate, polysulfone, polyurethane, polyester, polyamide, polyethylene, polypropylene, polyester, hydroxyapatite, calcium carbonate, titanium oxide, titanium, tantalum, zirconia, alumina, silica and the like.

The adhesion suppressive effect on cell or biological tissue can be examined by, though not particularly limited, adding a medium on the surface of the above-mentioned medical material or a substrate coated with the medical material, performing cell culture for a given period (e.g., 10-40 days), removing the medium, and measuring the residual amount of cells. To be specific, it can be examined as shown in the below-mentioned Examples.

On the other hand, when a medical material superior to the cell adhesion effect is obtained, the polyamino acid contained in the medical material of the present invention can be constituted by one or two kinds of amino acid residue. When polyamino acid is constituted by one kind of amino acid residue, said amino acid residue is not particularly limited as long as it is an amino acid residue shown above, and can be a valine residue, a glutamic acid residue optionally containing a protecting group in the side chain, or a lysine residue optionally containing a protecting group in the side chain. In addition, when polyamino acid is constituted by two kinds of amino acid residues, one of the two kinds of amino acid residues is not particularly limited as long as it is an amino acid residue shown above, and can be a lysine residue optionally containing a protecting group in the side chain, a glutamic acid residue optionally containing a protecting group in the side chain, or a phenylalanine residue.

When one of the two kinds of amino acid residues is the aforementioned lysine residue, the other kind is not particularly limited, and can be an alanine residue, a valine residue, a phenylalanine residue, or an isoleucine residue. That is, the combination of the two kinds of amino acid residues is a lysine residue optionally containing a protecting group in the side chain and an alanine residue, a lysine residue optionally containing a protecting group in the side chain and a valine residue, a lysine residue optionally containing a protecting group in the side chain and a phenylalanine residue, or a lysine residue optionally containing a protecting group in the side chain and an isoleucine residue.

When one of the two kinds of amino acid residues is the aforementioned glutamic acid residue, the other kind is not particularly limited, and can be an alanine residue or a phenylalanine residue. That is, the combination of the two kinds of amino acid residues is a glutamic acid residue optionally containing a protecting group in the side chain and an alanine residue, or a glutamic acid residue optionally containing a protecting group in the side chain and a phenylalanine residue.

When one of the two kinds of amino acid residues is a phenylalanine residue, the other kind is not particularly limited, and can be a valine residue or a leucine residue. That is, the combination of the two kinds of amino acid residues is a phenylalanine residue and a valine residue, or a phenylalanine residue and a leucine residue.

When the protecting group content of polyamino acid is adjusted, indication of a lysine residue or glutamic acid residue having a protecting group in the side chain encompasses the existence of a lysine residue or glutamic acid residue free of a protecting group in parts thereof, as in the above.

While the above-mentioned polyamino acid is not particularly limited, poly-γ-methyl-L-glutamic acid, poly-L-phenylalanine/N$^\epsilon$-benzyloxycarbonyl-L-lysine (9/1-3/7), poly-γ-methyl-L-glutamic acid deprotected by KOH treatment and the like, poly-N$^\epsilon$-benzyloxycarbonyl-L-lysine deprotected by HBr treatment and the like, poly-L-alanine/N$^\epsilon$-benzyloxycarbonyl-L-lysine (6/4-3/7) deprotected by HBr treatment and the like, poly-L-phenylalanine/N$^\epsilon$-benzyloxycarbonyl-L-lysine (9/1-3/7) deprotected by HBr treatment and the like are specifically preferable, and poly-γ-methyl-L-glutamic acid deprotected by KOH treatment and the like, poly-L-alanine/NE-benzyloxycarbonyl-L-lysine (3/7) deprotected by HBr treatment and the like can be mentioned. When these polyamino acids are used, the medical material of the present invention can be a fiber structure.

While the above-mentioned polyamino acid is not particularly limited, poly-L-valine, poly-γ-methyl-L-glutamic acid, poly-L-alanine/γ-methyl-L-glutamic acid (3/7), poly-L-valine/$N^{\epsilon}$-benzyloxycarbonyl-L-lysine (6/4), poly-L-isoleucine/$N^{\epsilon}$-benzyloxycarbonyl-L-lysine (6/4), poly-L-valine/L-phenylalanine (5/5), poly-L-leucine/L-phenylalanine (5/5), poly-γ-methyl-L-glutamic acid deprotected by KOH treatment and the like, poly-L-alanine/γ-methyl-L-glutamic acid (3/7) deprotected by KOH treatment and the like, poly-L-phenylalanine/γ-methyl-L-glutamic acid (6/4) deprotected by KOH treatment and the like, poly-L-valine/$N^{\epsilon}$-benzyloxycarbonyl-L-lysine (6/4) deprotected by HBr treatment and the like, poly-L-isoleucine/$N^{\epsilon}$-benzyloxycarbonyl-L-lysine (6/4) deprotected by HBr treatment and the like are preferable, poly-γ-methyl-L-glutamic acid, poly-L-isoleucine/Nε-benzyloxycarbonyl-L-lysine (6/4), poly-L-valine/L-phenylalanine (5/5), poly-γ-methyl-L-glutamic acid deprotected by KOH treatment and the like, poly-L-alanine/γ-methyl-L-glutamic acid (3/7) deprotected by KOH treatment and the like, poly-L-phenylalanine/γ-methyl-L-glutamic acid (6/4) deprotected by KOH treatment and the like, poly-L-isoleucine/Nε-benzyloxycarbonyl-L-lysine (6/4) deprotected by HBr treatment and the like are more preferable, and poly-γ-methyl-L-glutamic acid, poly-L-valine/L-phenylalanine (5/5), poly-γ-methyl-L-glutamic acid deprotected by KOH treatment and the like can be mentioned. When these polyamino acids are used, the medical material of the present invention can be a film.

In addition, while the above-mentioned polyamino acid is not particularly limited, poly-$N^{\epsilon}$-benzyloxycarbonyl-L-lysine, poly-L-alanine/$N^{\epsilon}$-benzyloxycarbonyl-L-lysine (6/4-3/7), poly-$N^{\epsilon}$-benzyloxycarbonyl-L-lysine deprotected by HBr treatment and the like, poly-L-alanine/$N^{\epsilon}$-benzyloxycarbonyl-L-lysine (6/4-3/7) deprotected by HBr treatment and the like, and poly-L-lysine are preferable, poly-$N^{\epsilon}$-benzyloxycarbonyl-L-lysine, poly-L-alanine/$N^{\epsilon}$-benzyloxycarbonyl-L-lysine (6/4), poly-L-alanine/$N^{\epsilon}$-benzyloxycarbonyl-L-lysine (6/4) deprotected by HBr treatment and the like, and poly-L-lysine are more preferable, and poly-$N^{\epsilon}$-benzyloxycarbonyl-L-lysine, poly-L-alanine/$N^{\epsilon}$-benzyloxycarbonyl-L-lysine (6/4), poly-L-alanine/$N^{\epsilon}$-benzyloxycarbonyl-L-lysine (6/4) deprotected by HBr treatment and the like can be mentioned. When these polyamino acids are used, the medical material of the present invention can be a coating.

The above-mentioned medical material having the cell adhesion effect is useful as, for example, a cell supporting substrate in a cell culture apparatus, a supporting substrate for an organism and the like in a bioreactor, and the like.

With the effect shown above, the present invention can also provide a method of adhering cells, which uses the above-mentioned medical material containing, as a main component, a polyamino acid having an amino acid residue. Use of such medical material enables promotion of cell differentiation while adhering cells.

The method can contain a step of transplanting the above-mentioned medical material to a subject in need thereof. For the transplantation, the medical material is preferably pressed against the affected part in need thereof. While the target to be applied with the above-mentioned medical material is not particularly limited, mammals (e.g., human, mouse, rat, monkey, dog, bovine, horse, swine, sheep, goat, rabbit, hamster etc.) are preferable.

While the cell to be adhered is not particularly limited, it can be, for example, any cell of mammals (e.g., human, mouse, rat, monkey, dog, bovine, horse, swine, sheep, goat, rabbit, hamster etc.) [for example, hepatocyte, splenocyte, nerve cell, glial cell, pancreatic β cell, bone marrow cell, mesangial cell, Langerhans cell, epidermal cell, epithelial cell, goblet cell, endothelial cell, smooth muscle cell, fibroblast, fiber cell, muscle cell, adipocyte, immunocyte (e.g., macrophage, T cell, B cell, natural killer cell, mast cell, neutrophil, basophil, eosinophils, monocyte), megakaryocyte, synovial cell, chondrocyte, osteocyte, osteoblast, osteoclast, mammary cell, hepatocyte or interstitial cell, or progenitor cell, stem cell, cancer cell etc. of these cells].

This method can also serve for ex vivo use, and can contain a step of contacting a cell with a surface of the above-mentioned medical material, and a step of cultivating the cell. The cell to be the target of contact is not particularly limited, and the cells similar to those exemplified above can be used. Among those, progenitor cells and stem cells are preferable, since they can be utilized in the field of regenerative medicine.

While the method of contacting the cell is not particularly limited as long as the cell can be cultured thereafter, for example, it can be performed by preparing a suspension of the cells in a liquid medium and the like and adding the obtained solution to a vessel and the like containing the above-mentioned medical material.

The medium for cultivating the cell is appropriately selected according to the kind of the cell to be used and examples thereof include, but are not limited to, DMEM medium, MEM medium, BME medium, DME medium, α-MEM medium, IMEM medium, ES medium, DM-160 medium, Fisher medium, F12 medium, WE medium, RPMI medium, StemSpan medium, StemPro medium, a mixed medium thereof and the like. The medium can contain a cytokine and a cell growth factor as additive as necessary. The presence of cytokine and cell growth factor can further increase the cell proliferation rate and cell activity. Specific examples thereof include, but are not limited to, erythropoietin, granulocyte colony stimulating factor (G-CSF), stem cell factor, Flk2/Flk3 ligand, thrombopoietin, soluble interleukin-6 receptor, interleukin-3 and the like.

The cell culture conditions can be appropriately determined according to the medium to be used. For example, while the culture temperature is not particularly limited, it is about 30-40° C., preferably about 37° C. The $CO_2$ concentration is, for example, about 1-10%, preferably about 2-7%. The culture period can be about 1 week or more, including subculturing several times, preferably resulting in about 3-5 weeks. The cells are preferably cultured in an incubator, and the culture medium is at rest, or can be agitated using, for example, a bioreactor and the like.

In this method, the above-mentioned medical material may be directly used, or processed into a suitable form before use, or immobilized on the surface of a substrate other than the medical material by coating, applying, and the like before use. Particularly, when the medical material of the present invention is a coating, it can be easily applied to the surface of the aforementioned substrate. As the material to be used as the substrate, a material used for medical purposes is preferable, and examples thereof include polyvinyl chloride, cellulose polymer, polystyrene, polymethylmethacrylate, polycarbonate, polysulfone, polyurethane, polyester, polyamide, polyethylene, polypropylene, polyester, hydroxyapatite, calcium carbonate, titanium oxide, titanium, tantalum, zirconia, alumina, silica and the like.

While the cell adhesion effect is not particularly limited, it can be examined by adding a medium on the surface of the above-mentioned medical material or a substrate coated with the medical material, performing cell culture for a given period (e.g., 10-40 days), removing the medium and measuring the amount of the cells showing adhesion growth. To be specific, it can be examined as shown in the below-mentioned Examples.

EXAMPLES

The present invention is explained in more detail in the following by referring to Examples, which are not to be construed as limitative in any manner.

As medical materials, the fiber structures of Production Examples 1-32 were produced as follows.

Production Example 1

Poly-L-Alanine Fiber Structure

N-carboxy-L-alanine anhydride (1.4 wt %) was added to benzene and the mixture was stirred for 2-3 days to give poly-L-alanine. This was dissolved in a dichloromethane-trifluoroacetic acid mixed solvent (50:50 (v/v)) to give a 4 wt % poly-L-alanine solution. This solution was placed in a syringe (TERUMO CORPORATION) equipped with a nozzle (needle, diameter 940 μm) where the distance between the nozzle and the collector was set to 10-15 cm, and the solution was discharged while applying a 20-38 kV voltage to form a fiber structure made of poly-L-alanine on a collector. A scanning electron microscope (SEM) photograph of the surface of the obtained fiber structure made of poly-L-alanine is shown in FIG. 1.

Production Example 2

Poly-L-Leucine Fiber Structure

N-carboxy-L-leucine anhydride (11.1 wt %) was added to 1,2-dichloroethane, and N,N-dimethyl-1,3-propanediamine was added as an initiator. The mixture was stirred for 2-3 days to give poly-L-leucine. This was dissolved in a dichloromethane-trifluoroacetic acid mixed solvent (30:70 (v/v)) to give a 4 wt % poly-L-leucine solution. A fiber structure made of poly-L-leucine was obtained from this solution in the same manner as in Production Example 1.

Production Examples 3-7

Various Polyamino Acid Fiber Structures

In the same manner as in Production Example 1 or 2, various N-carboxy-L-amino acid anhydrides were added to a polymerization solvent, a polymerization initiator was added as necessary, and the mixture was stirred for 2-3 days to give various polyamino acids. The polymerization solvents and polymerization initiators used are as shown in Table 1. Solutions of various polyamino acids were prepared using the solvents shown in Table 1, and fiber structures made of various polyamino acids were obtained from these solutions in the same manner as in Production Example 1.

Production Example 8

Fiber Structure of Poly-L-Alanine/γ-Methyl-L-Glutamic Acid Copolymer (9/1)

N-carboxy-L-alanine anhydride and N-carboxy-γ-methyl-L-glutamic acid anhydride were added to benzene at a molar ratio of 9:1, total 1.4 wt %, and the mixture was stirred for 2-3 days to give a poly-L-alanine/γ-methyl-L-glutamic acid copolymer (9/1). This was dissolved in a dichloromethane-trifluoroacetic acid mixed solvent (50:50 (v/v)) to give a 8 wt % poly-L-alanine/γ-methyl-L-glutamic acid copolymer (9/1) solution. A fiber structure made of poly-L-alanine/γ-methyl-L-glutamic acid copolymer (9/1) was obtained from this solution in the same manner as in Production Example 1.

Production Examples 9-22

Fiber Structures of Various Polyamino Acid Copolymers Structure

In the same manner as in Production Example 8, two kinds of N-carboxy-L-amino acid anhydrides were added to a polymerization solvent, a polymerization initiator was added as necessary, and the mixture was stirred for 2-3 days to give various polyamino acid copolymers. The materials and conditions shown in Table 1 were used. Solutions of various polyamino acid copolymers were prepared using the solvents shown in Table 1, and fiber structures made of various polyamino acid copolymers were obtained from these solutions in the same manner as in Production Example 1.

Production Example 23

Fiber Structure of poly-L-glutamine/γ-methyl-L-glutamic Acid Copolymer

N-carboxy-γ-methyl-L-glutamic acid anhydride (16.6 wt %) was added to 1,2-dichloroethane, N,N-dimethyl-1,3-propanediamine was added as an initiator, and the mixture was stirred for 2-3 days to give poly-γ-methyl-L-glutamic acid. Thereto were added 4 equivalents and 0.8 equivalents of 2,2,2-Trichloro-1-ethanol (manufactured by TOKYO CHEMICAL INDUSTRY CO., LTD.) and p-toluenesulfonic acid 1 hydrate (manufactured by TOKYO CHEMICAL INDUSTRY CO., LTD.), respectively, relative to the number of moles of N-carboxy-γ-methyl-L-glutamic acid anhydride, and the mixture was reacted at 80° C. to give a poly-γ-methyl/(2,2,2-trichloroethyl)-L-glutamic acid copolymer. This was reacted in tetrahydrofuran with ammonia in a large excess relative to mole of N-carboxy-γ-methyl-L-glutamic acid anhydride to give poly-L-glutamine/γ-methyl-L-glutamic acid. This was dissolved in a dichloromethane-trifluoroacetic acid mixed solvent (1:3 (v/v)) to give a 14-15 wt % poly-L-glutamine/γ-methyl-L-glutamic acid copolymer solution. A fiber structure made of a poly-L-glutamine/γ-methyl-L-glutamic acid copolymer was obtained from this solution in the same manner as in Production Example 1.

Production Example 24

Fiber Structure of poly-γ-methyl/(polyethylene glycol)-L-glutamic Acid Copolymer To poly-γ-methyl-L-glutamic acid obtained in Production Example 23 were added 2 equivalents and 0.2 equivalents of polyethylene glycol methylether (manufactured by Sigma-Aldrich Corporation, average molecular weight 350) and p-toluenesulfonic acid 1 hydrate, respectively, relative to the number of moles of N-carboxy-γ-methyl-L-glutamic acid anhydride, and the mixture was reacted at 75° C. to give a poly-γ-methyl/(polyethylene glycol)-L-glutamic acid copolymer. The weight average molecular weight measured by the method described in measurement 1 was $1.4×10^6$. This was dissolved in 2,2,2-trifluoroethanol to give a 10 wt % poly-γ-methyl/(polyethylene glycol)-L-glutamic acid copolymer solution. A fiber structure made of a poly-γ-methyl/(polyethylene glycol)-L-glutamic acid copolymer was obtained from this solution in the same manner as in Production Example 1.

Production Example 25

Fiber Structure of Poly-L-Alanine/L-Lysine Copolymer

To the poly-L-alanine/$N^ε$-benzyloxycarbonyl-L-lysine copolymer (9/1) obtained in Production Example 16 were added 270 equivalents and 5 equivalents of trifluoroacetic acid (manufactured by TOKYO CHEMICAL INDUSTRY CO., LTD.) and thioanisole (manufactured by TOKYO CHEMICAL INDUSTRY CO., LTD.), respectively, relative to the number of moles of N-carboxy-N'-benzyloxycarbonyl-L-lysine anhydride, and the mixture was reacted at room temperature to give a poly-L-alanine/L-lysine copolymer. This was dissolved in a dichloromethane-trifluoroacetic acid mixed solvent (50:70 (v/v)) to give a 4.4 wt % poly-L-alanine/L-lysine copolymer solution. A fiber structure made of a poly-L-alanine/L-lysine copolymer was obtained from this solution in the same manner as in Production Example 1.

Production Example 26

Fiber Structure of poly-L-alanine-poly-L-lysine Mixture

Poly-L-alanine obtained in Production Example 1 and poly-L-lysine hydrobromide (manufactured by Sigma-Aldrich Corporation, weight average molecular weight>300,000) were dissolved in a dichloromethane-trifluoroacetic acid-N,N-dimethylformamide mixed solvent (50:50:12.5 (v/v)) at a weight ratio of 9:1 to give a 4 wt % poly-L-alanine-poly-L-lysine mixture solution. A fiber structure made of poly-L-alanine-poly-L-lysine mixture was obtained from this solution in the same manner as in Production Example 1.

Production Example 27

Fiber Structure of poly-L-alanine-poly-$N^ε$-benzyloxycarbonyl-L-lysine Mixture (9/1)

poly-L-alanine obtained in Production Example 1 and poly-$N^ε$-benzyloxycarbonyl-L-lysine obtained in Production Example 5 were dissolved in a dichloromethane-trifluoroacetic acid mixed solvent (50:50 (v/v)) at a molar ratio of 9:1 based on monomer to give a 5.3 wt % poly-L-alanine-poly-$N^ε$-benzyloxycarbonyl-L-lysine mixture (9/1) solution. A fiber structure made of poly-L-alanine-poly-$N^ε$-benzyloxycarbonyl-L-lysine mixture (9/1) was obtained from this solution in the same manner as in Production Example 1.

Production Example 28

Fiber Structure of poly-L-alanine-poly-$N^ε$-benzyloxycarbonyl-L-lysine Mixture (6/4)

Poly-L-alanine obtained in Production Example 1 and poly-$N^ε$-benzyloxycarbonyl-L-lysine obtained in Production Example 5 were dissolved in a dichloromethane-trifluoroacetic acid mixed solvent (50:50 (v/v)) at a molar ratio of 6:4 based on monomer to give a 5.3 wt % poly-L-alanine-poly-$N^ε$-benzyloxycarbonyl-L-lysine mixture (6/4) solution. A fiber structure made of a poly-L-alanine-poly-$N^ε$-benzyloxycarbonyl-L-lysine mixture (6/4) was obtained from this solution in the same manner as in Production Example 1.

Production Example 29

Poly-γ-benzyl-L-glutamic Acid Fiber Structure

N-carboxy-γ-benzyl-L-glutamic acid anhydride was polymerized to give Poly-γ-Benzyl-L-Glutamic acid, which was dissolved in a dichloromethane-trifluoroacetic acid mixed solvent to give a 4 wt % Poly-γ-Benzyl-L-Glutamic acid solution. A fiber structure made of Poly-γ-Benzyl-L-Glutamic acid was obtained from this solution in the same manner as in Production Example 1.

Production Example 30

Chitosan Fiber Structure

A chitosan powder (Wako Pure Chemical Industries, Ltd.) was dissolved in an acetic acid-trifluoroacetic acid mixed solvent (10:90 (v/v)) to give a 4 wt % chitosan solution. A fiber structure made of chitosan was obtained from this solution in the same manner as in Production Example 1.

Production Example 31

Cellulose Fiber Structure

A cellulose powder (Wako Pure Chemical Industries, Ltd.) was dissolved in an acetic acid-trifluoroacetic acid mixed solvent (10:90 (v/v)) to give a 4 wt % cellulose solution. A fiber structure made of cellulose was obtained from this solution in the same manner as in Production Example 1.

Production Example 32

Gelatin Fiber Structure

A gelatin powder was dissolved in trifluoroacetic acid to give a 9 wt % gelatin solution. A fiber structure made of gelatin was obtained from this solution in the same manner as in Production Example 1.

[Measurement of Weight Average Molecular Weight]

The weight average molecular weight was measured by a gel penetration chromatography apparatus (GPC, Hitachi Corporation, LaChrom Elite) provided with an analytical column (Showa Denko K.K., Shodex K-802 and K-806M). A measurement solution was prepared by dissolving polyamino acid in chloroform to a concentration of 0.25-1.0% (w/v), and subjected to filter filtration. The measurement solution (10-80 μl) was injected, and the mixture was measured under the conditions of eluent flow rate: 1 ml/min, column maintenance temperature: 40° C. Polystyrene for calibration was used for the calculation of the weight average molecular weight.

TABLE 1

| | N-carboxy-L-amino acid anhydride | polymerization solvent | Polymerizetion concentration (wt %) | polymerization initiator | weight average molecular weight | solvent for solutionization | solution concentration (wt %) |
|---|---|---|---|---|---|---|---|
| Prod. Ex. 3 | N-carboxy-L-valine anhydride | benzene | 5.7 | triethylamine | — | dichloromethane-trifluoroacetic acid 1:4(v/v) | 8.0 |
| Prod. Ex. 4 | N-carboxy-β-benzyl-L-aspartic acid anhydride | chloroform | 4.8 | N,N-dimethyl-1,3-propanediamine | $2.4 \times 10^6$ | chloroform-trifluoroacetic acid 99:1(v/v) | 9.4 |
| Prod. Ex. 5 | N-carboxy-N$^\epsilon$-benzyloxycarbonyl-L-lysine anhydride | chloroform | 4.8 | triethylamine | $3.7 \times 10^5$ | 1,1,1,3,3,3-hexafluoro-2-propanol | 10.0 |
| Prod. Ex. 6 | N-carboxy-O-acetyl-L-tyrosine anhydride | N,N-dimethylformamide | 40 | cyclohexylamine | — | dichloromethane-trifluoroacetic acid 1:3(v/v) | 20.0 |
| Prod. Ex. 7 | N-carboxy-L-tryptophananhydride | N,N dimethylformamide | 50 | cyclohexylamine | — | N,N-dimethylformamide | 42.0 |
| Prod. Ex. 9 | N-carboxy-L-alanine anhydride and N-carboxy-γ-methyl-L-glutamic acid anhydride, molar ratio 6:4 | benzene | 1.6 | — | — | dichloromethane-trifluoroacetic acid 1:1(v/v) | 9.9 |
| Prod. Ex. 10 | N-carboxy-L-leucine anhydride and N-carboxy-γ-methyl-L-glutamic acid anhydride, molar ratio 9:1 | 1,2-dichloro-ethane | 8.3 | N,N-dimethyl-1,3-propanediamine | — | dichloromethane-trifluoroacetic acid 1:4(v/v) | 6.7 |
| Prod. Ex. 11 | N-carboxy-L-leucine anhydride and N-carboxy-γ-methyl-L-glutamic acid anhydride, molar ratio 6:4 | 1,2-dichloro-ethane | 8.7 | N,N-dimethyl-1,3-propanediamine | — | dichloromethane-trifluoroacetic acid 1:4(v/v) | 7.7 |
| Prod. Ex. 12 | N-carboxy-L-valine anhydride and N-carboxy-γ-methyl-L-glutamic acid anhydride, molar ratio 6:4 | chloroform | 1.6 | triethylamine | — | dichloromethane-trifluoroacetic acid 1:4(v/v) | 5.6 |
| Prod. Ex. 13 | N-carboxy-L-isoleucine anhydride and N-carboxy-γ-methyl-L-glutamic acid anhydride, molar ratio 6:4 | dichloro-methane | 5.5 | N,N-dimethyl-1,3-propanediamine | — | dichloromethane-trifluoroacetic acid 1:4(v/v) | 7.4 |
| Prod. Ex. 14 | N-carboxy-L-phenylalanine anhydride and N-carboxy-γ-methyl-L-glutamic acid anhydride, molar ratio 9:1 | dichloro-methane | 8.6 | N,N-dimethyl-1,3-propanediamine | $6.1 \times 10^5$ | dichloromethane-trifluoroacetic acid 3:2(v/v) | 3.5 |
| Prod. Ex. 15 | N-carboxy-L-phenylalanine anhydride and N-carboxy-γ-methyl-L-glutamic acid anhydride, molar ratio 6:4 | dichloro-methane | 8.2 | N,N-dimethyl-1,3-propanediamine | $8.5 \times 10^5$ | dichloromethane-trifluoroacetic acid 3:2(v/v) | 12.5 |
| Prod. Ex. 16 | N-carboxy-L-alanine anhydride and N-carboxy-N$^\epsilon$-benzyloxycarbonyl-L-lysine, molar ratio 9:1 | benzene | 1.5 | — | — | dichloromethane-trifluoroacetic acid 1:1(v/v) | 5.3 |
| Prod. Ex. 17 | N-carboxy-L-alanine anhydride and N-carboxy-N$^\epsilon$-benzyloxycarbonyl-L-lysine, molar ratio 6:4 | benzene | 2.2 | — | — | 1,1,1,3,3,3-hexafluoro-2-propanol | 8.0 |
| Prod. Ex. 18 | N-carboxy-L-alanine anhydride and N-carboxy-N$^\epsilon$-benzyloxycarbonyl-L-lysine, molar ratio 3:7 | benzene | 2.7 | — | — | 1,1,1,3,3,3-hexafluoro-2-propanol | 10.0 |
| Prod. Ex. 19 | N-carboxy-L-valine anhydride and N-carboxy-N$^\epsilon$-benzyloxycarbonyl-L-lysine, molar ratio 6:4 | chloroform | 1.9 | triethylamine | — | dichloromethane-trifluoroacetic acid 1:4(v/v) | 8.3 |
| Prod. Ex. 20 | N-carboxy-L-isoleucine anhydride and N-carboxy-N$^\epsilon$-benzyloxycarbonyl-L-lysine, molar ratio 6:4 | dichloro-methane | 7.0 | N,N-dimethyl-1,3-propanediamine | — | dichloromethane-trifluoroacetic acid 1:1(v/v) | 7.6 |
| Prod. Ex. 21 | N-carboxy-L-leucine anhydride and N-carboxy-L-phenylalanine, molar ratio 1:1 | dichloro-methane | 6.4 | N,N-dimethyl-1,3-propanediamine | — | dichloromethane-trifluoroacetic acid 1:4(v/v) | 3.0 |
| Prod. Ex. 22 | N-carboxy-L-valine anhydride and N-carboxy-L-phenylalanine, molar ratio 1:1 | chloroform | 2.1 | triethylamine | — | dichloromethane-trifluoroacetic acid 1:4(v/v) | 4.2 |

[Evaluation 1] Evaluation Method of Discharge Rate in Electrospinning

In the production of a fiber structure by electrospinning method containing steps 1-5, the total amount of the solution discharged from the start to the end of the discharge of the solution from the nozzle in step 2 was divided by the time from the start to the end, and the resulting value was taken as the discharge rate. The evaluation criteria are as described below.

◯: discharge rate not less than 10 ml/hour
x: discharge rate less than 10 ml/hour

[Evaluation 2] Evaluation Method of Average Fiber Diameter

After confirmation of the uniformity of the surface of the obtained fiber structure by visual observation, a part of the surface was collected, and mounted on a circular cover glass or cover slip (Thermo Scientific Inc., Nunc Thermanox Plastic Coverslips) with diameter 12-13 mm. The surface of the collected fiber structure was observed with a stereoscopic microscope (Nikon Inc., SMZ800) (magnification ×10) and, after confirmation of the uniformity of the surface, subjected to the surface observation under a scanning electron microscope (SEM, Hitachi Corporation, S-4800). First, the whole measurement sample was reviewed at magnification ×500 and, after confirmation of the uniformity of the surface, the magnification was changed to ×5,000, and photograph was randomly taken. The obtained photograph was placed such that it was wider than it was tall, and the lateral direction and longitudinal direction were divided into 5 equal parts and 2 equal parts, respectively, to give 10 sections with equal areas. The fibers in focus were selected from those at the center or nearest to the center of each section, and the diameter thereof was measured. The average thereof was determined and taken as the average fiber diameter. The evaluation criteria are as described below.

⊙: average fiber diameter less than 150 nm
◯: average fiber diameter not less than 150 nm and less than 500 nm
Δ: average fiber diameter not less than 500 nm and less than 1 μm
x: average fiber diameter not less than 1 μm

[Evaluation 3] Evaluation Method of Fiber Diameter Content Uniformity

The standard deviation of the average fiber diameter measured in evaluation 2 was determined. The evaluation criteria are as described below.

⊙: standard deviation less than 30 nm
◯: standard deviation not less than 30 nm and less than 90 nm
Δ: standard deviation not less than 90 nm and less than 200 nm
x: standard deviation not less than 200 nm

[Evaluation 4] Evaluation Method of Presence or Absence of Droplet

The number of circular products (marks showing accumulation in a droplet state on the collector) with the maximum diameter of not less than 5 μm in the photographs (magnification ×1,000) of the surface of the obtained fiber structure, which were taken randomly with a scanning electron microscope (SEM, Hitachi Corporation, S-4800), was counted. The evaluation criteria are as described below.

⊙: number of circular products not more than 3
◯: number of circular products not less than 4 and not more than 7
Δ: number of circular products not less than 8 and not more than 15
x: number of circular products not less than 16

[Evaluation 5] Evaluation Method of Cell Adhesion Suppressive Effect (1)

The obtained fiber structure was mounted on a circular cover glass or cover slip with a diameter of 12-13 mm (Thermo Scientific Inc., Nunc Thermanox Plastic Coverslips) and set on a 24-well culture plate (Nippon Becton Dickinson Company, Ltd., Falcon culture plate). As a control, a 24-well culture plate coated with collagen (Nippon Becton Dickinson Company, Ltd., Falcon collagen-coated culture plate) was used. For sterilization, they were immersed in a 70% aqueous ethanol solution, and washed with phosphate buffered saline (Takara Bio, Inc., PBS(−)). Human bone marrow mesenchymal stem cells (Lonza, Human Mesenchymal Stem Cell) were suspended in a mesenchymal stem cell medium (Lonza, MSCGM) or Dulbecco's Modified Eagle Medium (Invitrogen Corporation, GIBCO DMEM) supplemented with inactivated fetal bovine serum (Invitrogen Corporation, GIBCO FBS) and penicillin-streptomycin (Sigma-Aldrich Corporation), plated at 20,000 cells/well, and cultured at 5% $CO_2$/37° C. in an incubator (Thermo Scientific Inc., Form Incubator) for 3 days. After culture, the medium was removed and the cells were lysed in a citric acid (NACALAI TESQUE, INC.)-sodium chloride (NACALAI TESQUE, INC.) buffer containing sodium lauryl sulfate (NACALAI TESQUE, INC.). Thereto was added Bisbenzimide H33258 Fluorochrome Trihydrochloride DMSO solution (NACALAI TESQUE, INC.), and cellular DNA was quantified to obtain the number of cells showing adhesion growth on the fiber structure. The evaluation criteria are as described below.

+++: amount of cellular DNA less than 10% than that of control
++: amount of cellular DNA not less than 10% and less than 30% than that of control
+: amount of cellular DNA not less than 30% and less than 50% than that of control

[Evaluation 6] Evaluation Method of Cell Adhesion Suppressive Effect (2)

In the same manner as in evaluation 5, cells were seeded and cultured. After plating, the cells were cultured for 3 days, and a viable cell count reagent (NACALAI TESQUE, INC., Cell Count Reagent SF) was added to the medium. The cells were placed in an incubator again and, after 4-5 hr, the absorbance was measured (measurement wavelength: 450 nm).

+++: absorbance less than 10% than that of control
++: absorbance not less than 10% and less than 30% than that of control
+: absorbance not less than 30% and less than 50% than that of control The evaluation methods shown in evaluations 5 and 6 are widely-used methods for measuring the cell number in view of the convenience of operation, measurement precision and the like.

The fiber structures obtained in the above-mentioned Production Examples 1-32 were subjected to the evaluation of the above-mentioned evaluations 1-6. The results thereof are shown in Table 2 and Table 3. The items not evaluated are shown with "-".

TABLE 2

| | Polymer constituting fiber structure | evaluation 1 discharge rate | evaluation 2 average fiber diameter | evaluation 3 uniformity of diameter | evaluation 4 no droplet accumulation | evaluation 5 cell adhesion suppressive effect | evaluation 6 cell adhesion suppressive effect |
|---|---|---|---|---|---|---|---|
| Prod. Ex. 1 | poly-L-alanine | ○ | ◎ | ◎ | ◎ | +++ | − |
| Prod. Ex. 2 | poly-L-leucine | ○ | ○ | ○ | ○ | − | +++ |
| Prod. Ex. 3 | poly-L-valine | ○ | ○ | ○ | ○ | +++ | − |
| Prod. Ex. 4 | poly-β-benzyl-L-aspartic acid | ○ | ○ | Δ | Δ | ++ | − |
| Prod. Ex. 5 | poly-N$^\epsilon$-benzyloxycarbonyl-L-lysine | ○ | ○ | Δ | ○ | − | ++ |
| Prod. Ex. 6 | poly-O-acetyl-L-tyrosine | ○ | ○ | ○ | ○ | − | − |
| Prod. Ex. 7 | poly-L-tryptophan | ○ | ○ | Δ | Δ | − | − |
| Prod. Ex. 29 | poly-γ-benzyl-L-glutamic acid (when evaluation 1 is ○) | ○ | X | X | X | − | − |
| | poly-γ-benzyl-L-glutamic acid (when evaluation 1 is X) | X | X | Δ | ○ | | |
| Prod. Ex. 30 | chitosan (when evaluation 1 is ○) | ○ | Δ | X | X | +++ | − |
| | chitosan (when evaluation 1 is X) | X | ○ | X | X | | |
| Prod. Ex. 31 | cellulose (when evaluation 1 is ○) | ○ | ○ | X | X | − | ++ |
| | cellulose (when evaluation 1 is X) | X | ○ | Δ | X | | |
| Prod. Ex. 32 | gelatin (when evaluation 1 is ○) | ○ | Δ | X | X | − | − |
| | gelatin (when evaluation 1 is X) | X | ○ | Δ | X | | |

TABLE 3

| | Polymer constituting fiber structure (number value is molar ratio) | evaluation 1 discharge rate | evaluation 2 average fiber diameter | evaluation 3 uniformity of diameter | evaluation 4 no droplet accumulation | evaluation 5 cell adhesion suppressive effect | evaluation 6 cell adhesion suppressive effect |
|---|---|---|---|---|---|---|---|
| Prod. Ex. 8 | poly-L-alanine/γ-methyl-L-glutamic acid 9/1 | ○ | ○ | Δ | ○ | +++ | − |
| Prod. Ex. 9 | poly-L-alanine/γ-methyl-L-glutamic acid 6/4 | ○ | ○ | Δ | ○ | +++ | − |
| Prod. Ex. 10 | poly-L-leucine/γ-methyl-L-glutamic acid 9/1 | ○ | ○ | Δ | ○ | + | − |
| Prod. Ex. 11 | poly-L-leucine/γ-methyl-L-glutamic acid 6/4 | ○ | ○ | Δ | ○ | + | − |
| Prod. Ex. 12 | poly-L-valine/γ-methyl-L-glutamic acid 6/4 | ○ | ○ | ○ | ◎ | ++ | − |
| Prod. Ex. 13 | poly-L-isoleucine/γ-methyl-L-glutamic acid 6/4 | ○ | ○ | ○ | Δ | +++ | − |
| Prod. Ex. 14 | poly-L-phenylalanine/γ-methyl-L-glutamic acid 9/1 | ○ | ○ | ○ | Δ | + | − |
| Prod. Ex. 15 | poly-L-phenylalanine/γ-methyl-L-glutamic acid 6/4 | ○ | ○ | Δ | ○ | + | − |
| Prod. Ex. 16 | poly-L-alanine/N$^\epsilon$-benzyloxycarbonyl-L-lysine 9/1 | ○ | ○ | ○ | Δ | +++ | − |
| Prod. Ex. 17 | poly-L-alanine/N$^\epsilon$-benzyloxycarbonyl-L-lysine 6/4 | ○ | ○ | Δ | ○ | + | − |
| Prod. Ex. 18 | poly-L-alanine/N$^\epsilon$-benzyloxycarbonyl-L-lysine 3/7 | ○ | ○ | ○ | ○ | + | − |
| Prod. Ex. 19 | poly-L-valine/N$^\epsilon$-benzyloxycarbonyl-L-lysine 6/4 | ○ | ○ | Δ | Δ | +++ | − |
| Prod. Ex. 20 | poly-L-isoleucine/N$^\epsilon$-benzyloxycarbonyl-L-lysine 6/4 | ○ | ○ | ○ | Δ | ++ | − |
| Prod. Ex. 21 | poly-L-leucine/L-phenylalanine 1/1 | ○ | ◎ | ○ | ◎ | − | − |
| Prod. Ex. 22 | poly-L-valine/L-phenylalanine 1/1 | ○ | ◎ | ◎ | ◎ | ++ | − |
| Prod. Ex. 23 | poly-L-glutamine/γ-methyl-L-glutamic acid | ○ | ○ | ○ | Δ | + | − |

TABLE 3-continued

|  | Polymer constituting fiber structure (number value is molar ratio) | evaluation 1 discharge rate | evaluation 2 average fiber diameter | evaluation 3 uniformity of diameter | evaluation 4 no droplet accumulation | evaluation 5 cell adhesion suppressive effect | evaluation 6 cell adhesion suppressive effect |
|---|---|---|---|---|---|---|---|
| Prod. Ex. 24 | poly-γ-(methyl/polyethylene glycol)-L-glutamic acid | ◯ | ◯ | Δ | Δ | ++ | − |
| Prod. Ex. 25 | poly-L-alanine/L-lysine | ◯ | ◯ | Δ | Δ | − | +++ |
| Prod. Ex. 26 | poly-L-alanine-poly-L-lysine | ◯ | ◯ | Δ | ◯ | − | +++ |
| Prod. Ex. 27 | poly-L-alanine-poly-N$^\epsilon$-benzyloxycarbonyl-L-lysine 9/1 | ◯ | ◯ | Δ | Δ | +++ | − |
| Prod. Ex. 28 | poly-L-alanine-poly-N$^\epsilon$-benzyloxycarbonyl-L-lysine 6/4 | ◯ | ◯ | ◯ | ◯ | ++ | − |

In Production Examples 1-28, good fiber structures with sufficiently small average fiber diameter, satisfactory fiber diameter uniformity, and free of droplets could be obtained. Of those, fiber structures made of poly-L-alanine, poly-L-leucine, poly-L-valine, poly-N$^\epsilon$-benzyloxycarbonyl-L-lysine, poly-L-alanine/γ-methyl-L-glutamic acid 9/1, poly-L-alanine/γ-methyl-L-glutamic acid 6/4, poly-L-isoleucine/γ-methyl-L-glutamic acid 6/4, poly-L-alanine/N$^\epsilon$-benzyloxycarbonyl-L-lysine 9/1, poly-L-valine/N$^\epsilon$-benzyloxycarbonyl-L-lysine 6/4, poly-L-alanine/L-lysine, poly-L-alanine-poly-L-lysine, poly-L-alanine-poly-N$^\epsilon$-benzyloxycarbonyl-L-lysine 9/1 are clearly medical materials superior in the cell adhesion suppressive effect (Production Examples 1, 2, 3, 5, 8, 9, 13, 16, 19, 25, 26, 27). Particularly, poly-L-alanine showed preferable results in all of average fiber diameter, content uniformity, droplet problem and suppression of cell adhesion. Production Example 29 was found to have difficulty in producing a good fiber structure. Production Examples 30-32 using chitosan, cellulose and gelatin failed to provide sufficient quality as a fiber structure, since all of them showed remaining droplets, inconsistent uniformity of average fiber diameter and the like.

[Evaluation 7] Influence of Production Conditions (Setting of Applied Voltage and Distance Between Nozzle and Collector)

By a method similar to that in Production Example 22 except that the voltage applied on the poly-L-valine/L-phenylalanine (1/1) solution shown in Production Example 22 was changed to 19-20 kV, production of a fiber structure made of poly-L-valine/L-phenylalanine (1/1) was tried.

By a method similar to that in Production Example 22 except that the voltage applied on the poly-L-valine/L-phenylalanine (1/1) solution shown in Production Example 22 was changed to 15 kV, production of a fiber structure made of poly-L-valine/L-phenylalanine (1/1) was tried.

By a method similar to that in Production Example 22 except that the voltage applied on the poly-L-valine/L-phenylalanine (1/1) solution shown in Production Example 22 was changed to 10 kV, production of a fiber structure made of poly-L-valine/L-phenylalanine (1/1) was tried.

By a method similar to that in Production Example 22 except that the voltage applied on the poly-L-valine/L-phenylalanine (1/1) solution shown in Production Example 22 was changed to 19-20 kV, and the distance between the nozzle containing the solution and the collector was changed to 5 cm, production of a fiber structure made of poly-L-valine/L-phenylalanine (1/1) was tried.

The surface of the obtained fiber structure was evaluated by visual observation. Specifically, the number of visible particulates was counted. The evaluation criteria of the particulates are as follows. The results thereof are shown in Table 4.

⊙: particulate number 0 per 1 cm$^2$

◯: particulate number not less than 1 and not more than 9 per 1 cm$^2$

Δ: particulate number not less than 10 and not more than 49 per 1 cm$^2$ x: particulate number not less than 50 per 1 cm$^2$ xx: measurement not possible

TABLE 4

| Polymer constituting fiber structure (numerical value is molar ratio) | Voltage for spinning | distance between nozzle and collector | evaluation 7 attachment of particulate |
|---|---|---|---|
| poly-L-valine/L-phenylalanine 1/1 | 19-20 kV | 15 cm | ⊙ |
| poly-L-valine/L-phenylalanine 1/1 | 15 kV | 15 cm | Δ |
| poly-L-valine/L-phenylalanine 1/1 | 10 kV | 15 cm | XX |
| poly-L-valine/L-phenylalanine 1/1 | 19-20 kV | 5 cm | X |

In the production of poly-L-valine/L-phenylalanine (1/1) fiber structures, when the voltage to be applied between nozzle and collector was decreased, particularly to 10 kV, the spinning performance became defective and a fiber structure could not be obtained. When the voltage was set to 15 kV, a fiber structure could be produced, but the discharged solution mostly reached in a droplet state on the collector and not less than 10 particulates were visually observed on the surface of the fiber structure. When the distance between the nozzle and the collector was shortened, particularly to 5 cm, the discharged solution mostly reached in a droplet state on the collector.

In this Example, polyamino acid was synthesized as shown in the following Synthetic Examples, a fiber structure, a film and a coating were manufactured and evaluated.

Synthetic Example 1

Synthesis of poly-L-alanine

N-carboxy-L-alanine anhydride was added to benzene (manufactured by KANTO CHEMICAL) to a concentration of 1.8 wt %, and the mixture was stirred at 55° C.-65° C. for 3-4 days to give poly-L-alanine.

Synthetic Examples 2-5

Synthesis of Various Polyamino Acids

In the same manner as in Synthetic Example 1, and using N-carboxy-L-amino acid anhydride shown in Table 5-1, and a polymerization initiator as appropriate, various homopolyamino acids were obtained. They were each prepared using the solvents and concentrations shown in Table 5-1.

Synthetic Example 6

Synthesis of poly-L-alanine/γ-methyl-L-glutamic Acid Copolymer

N-carboxy-L-alanine anhydride and N-carboxy-γ-methyl-L-glutamic acid anhydride were added to benzene at a molar ratio of 9:1 and 1.8 wt % in total, and the mixture was stirred at 55° C.-65° C. for 3-4 days to give a poly-L-alanine/γ-methyl-L-glutamic acid copolymer (molar ratio 9:1).

Synthetic Examples 7-21

Synthesis of Various Polyamino Acid Copolymers

In the same manner as in Synthetic Example 6, and using N-carboxy-L-amino acid anhydride shown in Table 5-1, and a polymerization initiator as appropriate, various polyamino acid copolymers were obtained. They were each prepared using the solvents and concentrations shown in Table 5-1.

Synthetic Examples 22-37

Synthesis of Various Polyamino Acids or Copolymers

In the same manner as in Synthetic Example 1 or 6, and using N-carboxy-L-amino acid anhydride shown in Table 5-2, and a polymerization initiator as appropriate, various polyamino acids or copolymers were obtained. They were each prepared using the solvents and concentrations shown in Table 5-2.

The composition ratio of various polyamino acid copolymers synthesized in Synthetic Examples 6-37 was measured according to the following. In addition, intrinsic viscosity of various polyamino acids synthesized in Synthetic Examples 6-37 was measured and the viscosity average molecular weight Mv was calculated.

[Measurement of Composition Ratio]

Polyamino acid (about 10 mg) was dissolved in deuterated trifluoroacetic acid, $^1$H nuclear magnetic resonance spectrum ($^1$HNMR, 400 MHz, BRUKER) was measured, and the amino acid composition ratio was calculated from the area ratio of each amino acid side chain-derived signal.

[Measurement of Intrinsic Viscosity and Calculation of Viscosity Average Molecular Weight Mv]

Polyamino acid (ca 50 mg) was dissolved in 11 ml of dichloroacetic acid (manufactured by TOKYO CHEMICAL INDUSTRY) to give a solution, 10 ml thereof was placed in a Ubellohde's viscometer (manufactured by SIBATA SCIENTIFIC TECHNOLOGY) and the time when the liquid surface of the solution passed between the gauges was measured in a thermostatic tank at 25° C. After the first measurement, dichloroacetic acid (1 ml) was added, and the mixture was stirred well and subjected to the second measurement. Furthermore, dichloroacetic acid (1 ml) was added, and the mixture was stirred well and subjected to the third measurement. The intrinsic viscosity ([η] unit: dL/g) was determined from the results of the third measurement. The viscosity average molecular weight Mv was calculated by any of the following 4 kinds of conversion formulas (all Mark-Houwink-Sakurada formula: $[\eta]=KM_v^a$).

conversion formula 1. $[\eta]=2.09\times10^{-4}\times Mv^{0.68}$
conversion formula 2. $[\eta]=2.24\times10^{-3}\times Mv^{0.58}$
conversion formula 3. $[\eta]=2.78\times10^{-5}\times Mv^{0.87}$
conversion formula 4. $[\eta]=2.78\times10^{-5}\times Mv^{0.87}$

TABLE 5-1

| Synthe. Ex. | synthesized polymer | N-carboxy-L-amino acid anhydride used | polymerization solvent | polymerization concentration (wt %) | polymerization initiator | composition ratio (mol/(mol) | intrinsic viscosity [η]dL/g | Mv | conversion formula |
|---|---|---|---|---|---|---|---|---|---|
| Synthe. Ex. 1 | poly-L-alanine | N-carboxy-L-alanine anhydride | benzene | 1.8 | — | — | — | — | — |
| Synthe. Ex. 2 | poly-L-valine | N-carboxy-L-valine anhydride | benzene | 5.7 | triethylamine | — | — | — | — |
| Synthe. Ex. 3 | poly-γ-methyl-L-glutamic acid | N-carboxy-γ-methyl-L-glutamic acid anhydride | 1,2-dichloroethane | 12.2 | N,N-dimethyl-propyl-1,3-diamine | — | 1.68 | $9.0 \times 10^4$ | 2 |
| Synthe. Ex. 4 | poly-γ-benzyl-L-glutamic acid | N-carboxy-γ-benzyl-L-glutamic acid anhydride | chloroform | 3.3 | triethylamine | — | 2.21 | $4.3 \times 10^5$ | 3 |
| Synthe. Ex. 5 | poly-N$^\epsilon$-benzyloxycarbonyl-L-lysine | N-carboxy-N$^\epsilon$-benzyloxycarbonyl-L-lysine anhydride | chloroform | 5.5 | triethylamine | — | 1.17 | $3.2 \times 10^5$ | 1 |
| Synthe. Ex. 6 | poly-L-alanine/γ-methyl-L-glutamic acid 9/1 | N-carboxy-L-alanine anhydride and N-carboxy-γ-methyl-L-glutamic acid anhydride, molar ratio 9:1 | benzene | 1.8 | — | 9.0/1.0 | 1.67 | $7.6 \times 10^4$ | 4 |
| Synthe Ex. 7 | poly-L-alanine/γ-methyl-L-glutamic acid 6/4 | N-carboxy-L-alanine anhydride and N-carboxy-γ-methyl-L-glutamic acid anhydride, molar ratio 6:4 | benzene | 2.6 | — | 6.0/4.0 | 0.91 | $3.1 \times 10^4$ | 2 |

TABLE 5-1-continued

| Synthe. Ex. | synthesized polymer | N-carboxy-L-amino acid anhydride used | polymerization solvent | polymerization concentration (wt %) | polymerization initiator | composition ratio (mol/(mol) | intrinsic viscosity [η]dL/g | Mv | conversion formula |
|---|---|---|---|---|---|---|---|---|---|
| Synthe. Ex. 8 | poly-L-alanine/γ-methyl-L-glutamic acid 3/7 | N-carboxy-L-alanine anhydride and N-carboxy-γ-methyl-L-glutamic acid anhydride, molar ratio 3:7 | 1,2-dichloro-ethane | 9.6 | N,N-dimethyl-propyl-1,3-diamine | 2.9/7.1 | 1.66 | $8.7 \times 10^4$ | 2 |
| Synthe. Ex. 9 | poly-L-leucine/γ-methyl-L-glutamic acid 9/1 | N-carboxy-L-leucine anhydride and N-carboxy-γ-methyl-L-glutamic acid anhydride, molar ratio 9:1 | 1,2-dichloro-ethane | 6.7 | N,N-dimethyl-propyl-1,3-diamine | 9.0/1.0 | insoluble in solvent | — | — |
| Synthe. Ex. 10 | poly-L-leucine/γ-methyl-L-glutamic acid 6/4 | N-carboxy-L-leucine anhydride and N-carboxy-γ-methyl-L-glutamic acid anhydride, molar ratio 6:4 | 1,2-dichloro-ethane | 7.1 | N,N-dimethyl-propyl-1,3-diamine | 6.1/3.9 | 1.39 | $6.4 \times 10^4$ | 2 |
| Synthe. Ex. 11 | poly-L-phenylalanine/γ-methyl-L-glutamic acid 6/4 | N-carboxy-L-phenylalanine anhydride and N-carboxy-γ-methyl-L-glutamic acid anhydride, molar ratio 6:4 | dichloro-methane | 6.6 | N,N-dimethyl-propyl-1,3-diamine | 6.0/4.0 | 1.29 | $5.7 \times 10^4$ | 2 |
| Synthe. Ex. 12 | poly-L-alanine/N$^\epsilon$-benzyloxycarbonyl-L-lysine 9/1 | N-carboxy-L-alanine anhydride and N-carboxy-N$^\epsilon$-benzyloxycarbonyl-L-lysine anhydride, molar ratio 9:1 | benzene | 1.7 | — | 9.1/0.9 | 2.99 | $1.7 \times 10^5$ | 4 |
| Synthe. Ex. 13 | poly-L-alanine/N$^\epsilon$-benzyloxycarbonyl-L-lysine 6/4 | N-carboxy-L-alanine anhydride and N-carboxy-N$^\epsilon$-benzyloxycarbonyl-L-lysine anhydride, molar ratio 6:4 | benzene | 2.6 | — | 6.0/4.0 | 0.90 | $2.2 \times 10^5$ | 1 |
| Synthe. Ex. 14 | poly-L-alanine/N$^\epsilon$-benzyloxycarbonyl-L-lysine 3/7 | N-carboxy-L-alanine anhydride and N-carboxy-N$^\epsilon$-benzyloxycarbonyl-L-lysine anhydride, molar ratio 3:7 | benzene | 3.1 | — | 3.7/6.3 | 0.66 | $1.4 \times 10^5$ | 1 |
| Synthe. Ex. 15 | poly-L-valine/N$^\epsilon$-benzyloxycarbonyl-L-lysine 6/4 | N-carboxy-L-valine anhydride and N-carboxy-N$^\epsilon$-benzyloxycarbonyl-L-lysine anhydride, molar ratio 6:4 | chloroform | 1.2 | triethyl-amine | 6.4/3.6 | insoluble in solvent | — | — |
| Synthe. Ex. 16 | poly-L-isoleucine/N$^\epsilon$-benzyloxycarbonyl-L-lysine 6/4 | N-carboxy-L-isoleucine anhydride and N-carboxy-N$^\epsilon$-benzyloxycarbonyl-L-lysine anhydride, molar ratio 6:4 | dichloro-methane | 3.9 | N,N-dimethyl-propyl-1,3-diamine | 6.2/3.8 | insoluble in solvent | — | — |
| Synthe. Ex. 17 | poly-L-phenylalanine/N$^\epsilon$-benzyloxycarbonyl-L-lysine 9/1 | N-carboxy-L-phenylalanine anhydride and N-carboxy-N$^\epsilon$-benzyloxycarbonyl-L-lysine anhydride, molar ratio 9:1 | dichloro-methane | 5.6 | N,N-dimethyl-propyl-1,3-diamine | un-measurable | insoluble in solvent | — | — |
| Synthe. Ex. 18 | poly-L-phenylalanine/N$^\epsilon$-benzyloxycarbonyl-L-lysine 6/4 | N-carboxy-L-phenylalanine anhydride and N-carboxy-N$^\epsilon$-benzyloxycarbonyl-L-lysine anhydride, molar ratio 6:4 | dichloro-methane | 6.4 | N,N-dimethyl-propyl-1,3-diamine | 5.6/6.4 | 1.36 | $4.0 \times 10^5$ | 1 |
| Synthe. Ex. 19 | poly-L-phenylalanine/N$^\epsilon$-benzyloxycarbonyl-L-lysine 3/7 | N-carboxy-L-phenylalanine anhydride and N-carboxy-N$^\epsilon$-benzyloxycarbonyl-L-lysine anhydride, molar ratio 3:7 | dichloro-methane | 7.8 | N,N-dimethyl-propyl-1,3-diamine | 3.5/6.5 | 1.05 | $2.8 \times 10^5$ | 1 |
| Synthe. Ex. 20 | poly-L-valine/L-phenylalanine 5/5 | N-carboxy-L-valine anhydride and N-carboxy-L-phenylalanine anhydride, molar ratio 5:5 | chloroform | 3.4 | triethyl-amine | 6.1/3.9 | insoluble in solvent | — | — |
| Synthe. Ex. 21 | poly-L-leucine/L-phenylalanine 5/5 | N-carboxy-L-leucine anhydride and N-carboxy-L-phenylalanine anhydride, molar ratio 5:5 | dichloro-methane | 4.9 | N,N-dimethyl-propyl-1,3-diamine | 5.1/4.9 | 1.60 | $7.2 \times 10^4$ | 4 |

TABLE 5-2

| | synthesized polymer | N-carboxy-L-amino acid anhydride used | polymerization solvent | polymerization concentration (wt %) | polymerization initiator | composition ratio (mol/mol) | intrinsic viscosity [η]dL/g | Mv | conversion formula | Note |
|---|---|---|---|---|---|---|---|---|---|---|
| Synthe. Ex. 22 | poly-L-phenylalanine/benzyl-L-aspartic acid/γ-methyl-L-glutamic acid 3/2/5 | N-carboxy-L-phenylalanine anhydride, N-carboxy-β-benzyl-L-aspartic acid anhydride, and N-carboxy-γ-methyl-L-glutamic acid anhydride | 1,2-dichloroethane | 7.4 | N,N-dimethyl-1,3-propane-diamine | 3.0/2.0/5.0 | 0.865 | $2.1 \times 10^5$ | 1 | — |
| Synthe. Ex. 23 | poly-L-phenylalanine/benzyl-L-aspartic acid/N$^\varepsilon$-benzyloxycarbonyl-L-lysine 3/2/5 | N-carboxy-L-phenylalanine anhydride, N-carboxy-β-benzyl-L-aspartic acid anhydride, and N-carboxy-N$^\varepsilon$-benzyloxycarbonyl-L-lysine anhydride | 1,2-dichloroethane | 9.4 | N,N-dimethyl-1,3-propane-diamine | 3.5/1.5/5.0 | 0.467 | $8.4 \times 10^4$ | 1 | — |
| Synthe. Ex. 24 | poly-L-leucine/L-glutamic acid 8/2 | N-carboxy-L-leucine anhydride and N-carboxy-γ-benzyl-L-glutamic acid anhydride | 1,2-dichloroethane | 7.3 | N,N-dimethyl-1,3-propane-diamine | 8.0/2.0 | insoluble in solvent | — | — | stirred in hydrogen bromide acetic acid solution and trifluoroacetic acid mixed solution after polymer synthesis |
| Synthe. Ex. 25 | poly-L-leucine/N$^\varepsilon$-benzyloxycarbonyl-L-lysine 9/1 | N-carboxy-L-leucine anhydride and N-carboxy-N$^\varepsilon$-benzyloxycarbonyl-L-lysine anhydride | 1,2-dichloroethane | 7.2 | N,N-dimethyl-1,3-propane-diamine | 9.1/0.9 | 0.552 | $5.9 \times 10^4$ | 1 | — |
| Synthe. Ex. 26 | poly-L-leucine/N$^\varepsilon$-benzyloxycarbonyl-L-lysine 6/4 | N-carboxy-L-leucine anhydride and N-carboxy-N$^\varepsilon$-benzyloxycarbonyl-L-lysine anhydride | 1,2-dichloroethane | 8.9 | N,N-dimethyl-1,3-propane-diamine | 6.2/3.8 | 1.074 | $1.6 \times 10^5$ | 1 | — |
| Synthe. Ex. 27 | poly-L-leucine/L-lysine 8/2 | N-carboxy-L-leucine anhydride and N-carboxy-N$^\varepsilon$-benzyloxycarbonyl-L-lysine anhydride | 1,2-dichloroethane | 7.7 | N,N-dimethyl-1,3-propane-diamine | 8.3/1.7 | 1 | $1.4 \times 10^5$ | 1 | stirred in hydrogen bromide acetic acid solution and trifluoroacetic acid mixed solution after polymer synthesis |
| Synthe. Ex. 28 | poly-L-leucine/L-glutamic acid/L-lysine 8/1/1 | N-carboxy-L-leucine anhydride, N-carboxy-γ-benzyl-L-glutamic acid anhydride, and N-carboxy-N$^\varepsilon$-benzyloxycarbonyl-L-lysine anhydride | 1,2-dichloroethane | 7.5 | N,N-dimethyl-1,3-propane-diamine | 8.2/0.94/0.86 | 0.937 | $1.3 \times 10^5$ | 1 | stirred in hydrogen bromide acetic acid solution and trifluoroacetic acid mixed solution after polymer synthesis |
| Synthe. Ex. 29 | poly-γ-methyl-L-glutamic acid/L-glutamic acid 8/2 | N-carboxy-γ-methyl-L-glutamic acid anhydride | 1,2-dichloroethane | 13.3 | N,N-dimethyl-1,3-propane-diamine | — | insoluble in solvent | — | — | after polymer synthesis, 2N NaOH was added and the mixture was stirred in methanol:isopropyl alcohol:water (2:2:1) |

TABLE 5-2-continued

| Synthe. Ex. | synthesized polymer | N-carboxy-L-amino acid anhydride used | polymerization solvent | polymerization concentration (wt %) | polymerization initiator | composition ratio (mol/mol) | intrinsic viscosity [η]dL/g | Mv | conversion formula | Note |
|---|---|---|---|---|---|---|---|---|---|---|
| Synthe. Ex. 30 | (poly-L-N$^\varepsilon$-benzyloxycarbonyl-L-lysine/N$^\varepsilon$-acetyl-L-lysine 6/4) + (poly-γ-methyl-L-glutamic acid) 1 + 1 | N-carboxy-N$^\varepsilon$-benzyloxycarbonyl-L-lysine anhydride, N-carboxy-γ-methyl-L-glutamic acid anhydride | chloroform, 1,2-dichloro-ethane | 3.2, 13.3 | triethyl-amine, N,N-dimethyl-1,3-propane-diamine | — | insoluble in solvent | — | — | stirred in hydrogen bromide acetic acid solution after polymer synthesis and then stirred in pyridine in the presence of acetic anhydride |
| Synthe. Ex. 31 | poly-L-valine/γ-methyl-L-glutamic acid 6/4 | N-carboxy-L-valine anhydride and N-carboxy-γ-methyl-L-glutamic acid anhydride | chloroform | 1.6 | triethyl-amine | 5.8/4.2 | insoluble in solvent | — | — | — |
| Synthe. Ex. 32 | poly-L-isoleucine/γ-methyl-L-glutamic acid 6/4 | N-carboxy-L-isoleucine anhydride and N-carboxy-γ-methyl-L-glutamic acid anhydride | dichloro-methane | 5.5 | N,N-dimethyl-1,3-propane-diamine | 4.6/5.3 | insoluble in solvent | — | — | — |
| Synthe. Ex. 33 | poly-L-glycine | N-carboxy-glycine anhydride | dimethyl sulfoxide | 3.3 | none | — | insoluble in solvent | — | — | — |
| Synthe. Ex. 34 | poly-L-N$^\varepsilon$-benzyloxycarbonyl-L-lysine/L-lysine 6/4 | N-carboxy-N$^\varepsilon$-benzyloxycarbonyl-L-lysine anhydride | chloroform | 3.2 | triethyl-amine | — | insoluble in solvent | — | — | treated by stirring in hydrogen bromide acetic acid solution after polymer synthesis |
| Synthe. Ex. 35 | poly-N$^\varepsilon$-benzyloxycarbonyl-L-lysine/N$^\varepsilon$-t-butoxycarbonylguanidino-L-lysine 6/4 | N-carboxy-N$^\varepsilon$-benzyloxycarbonyl-L-lysine anhydride | chloroform | 3.2 | triethyl-amine | — | insoluble in solvent | — | — | stirred in hydrogen bromide acetic acid solution after polymer synthesis and stirred in dimethylformamide in the presence of N,N'-di $$ thiourea•isopropyldiethylamine•2-chloro-N-methylpyridinium salt |
| Synthe. Ex. 36 | poly-L-glycine/γ-methyl-L-glutamic acid/L-glutamic acid 5/3/2 | N-carboxy-glycine anhydride and N-carboxy-γ-methyl-L-glutamic acid anhydride | dimethyl-formamide | 7.5 | N,N-dimethyl-1,3-propane-diamine | 5.4/4.6 | insoluble in solvent | — | — | after polymer synthesis, 2N NaOH was added and the mixture was stirred in methanol:isopropyl alcohol:water (2:2:1) |
| Synthe. Ex. 37 | poly-L-leucine/L-glutamic acid/L-lysine 6/1/3 | N-carboxy-L-leucine anhydride, N-carboxy-γ-benzyl-L-glutamic acid anhydride, and N-carboxy-N$^\varepsilon$-benzyloxycarbonyl-L-lysine anhydride | dichloro-methane, 1,4-dioxane | 7.0 | triethyl-amine | 6.0/1.0/3.0 | 1.223 | $1.8 \times 10^5$ | 1 | stirred in hydrogen bromide acetic acid solution and trifluoroacetic acid mixed solution after polymer synthesis |

Production Example 33

Poly-L-Alanine Fiber Structure

Poly-L-alanine synthesized in Synthetic Example 1 was dissolved in a dichloromethane-trifluoroacetic acid mixed solvent (50:50 (v/v)) to give a 4 wt % poly-L-alanine solution. This solution was placed in a syringe (manufactured by TERUMO CORPORATION) equipped with a nozzle (needle, diameter 940 μm) where the distance between the nozzle and the collector was set to 10-15 cm, and the solution was discharged while applying a 15-38 kV voltage to form a fiber structure made of poly-L-alanine on a collector.

Production Examples 34-47

Various Polyamino Acid Fiber Structures

In the same manner as in Production Example 33, solutions of various polyamino acids synthesized in Synthetic Examples 2-7, 9-14 and 17-19 were prepared under the conditions of Table 6-1-1 to give fiber structures.

Production Example 48

Fiber Structure of poly-L-alanine and poly-N$^\epsilon$-benzyloxycarbonyl-L-lysine Blend (Molar Ratio 9:1)

Poly-L-alanine synthesized in Synthetic Example 1 and poly-N$^\epsilon$-benzyloxycarbonyl-L-lysine synthesized in Synthetic Example 5 at a molar ratio of 9:1 were dissolved in a dichloromethane-trifluoroacetic acid mixed solvent (50/50 (v/v)) to give a 5.3 wt % blend solution. This solution was placed in a syringe equipped with a nozzle (diameter 940 μm) where the distance between the nozzle and the collector was set to 10-15 cm, and the solution was discharged while applying a 15-38 kV voltage to give a fiber structure made of a blend (molar ratio 9:1) of poly-L-alanine and poly-N$^\epsilon$-benzyloxycarbonyl-L-lysine on a collector.

Production Example 49

Fiber Structure of Poly-L-Alanine and Poly-N$^\epsilon$-Benzyloxycarbonyl-L-Lysine Blend (Molar Ratio 6:4)

Poly-L-alanine synthesized in Synthetic Example 1 and poly-N$^\epsilon$-benzyloxycarbonyl-L-lysine synthesized in Synthetic Example 5 were dissolved in a dichloromethane-trifluoroacetic acid mixed solvent (50/50 (v/v)) at a molar ratio of 6:4 to give a 5.3 wt % blend solution. A fiber structure was obtained from this solution in the same manner as in Production Example 48.

Production Examples 92-98

Various Polyamino Acid Fiber Structures

In the same manner as in Production Example 33, solutions of various polyamino acids synthesized in Synthetic Examples 22-28 were prepared under the conditions of Table 6-1-2 to give fiber structures.

TABLE 6-1-1

| Prod. Ex. | polymer constituting fiber structure | | solvent for solutionization | solution concentration (wt %) |
|---|---|---|---|---|
| Prod. Ex. 33 | poly-L-alanine | Synthe. Ex. 1 | dichloromethane-trifluoroacetic acid 50/50 (v/v) | 4.0 |
| Prod. Ex. 34 | poly-L-valine | Synthe. Ex. 2 | dichloromethane-trifluoroacetic acid 20/80 (v/v) | 7.0 |
| Prod. Ex. 35 | poly-γ-methyl-L-glutamic acid | Synthe. Ex. 3 | 1,2-dichloroethane-trifluoroacetic acid 95/5 (v/v) | 10.0 |
| Prod. Ex. 36 | poly-γ-benzyl-L-glutamic acid | Synthe. Ex. 4 | trifluoroacetic acid | 10.0 |
| Prod. Ex. 37 | poly-N$^\epsilon$-benzyloxycarbonyl-L-lysine | Synthe. Ex. 5 | 1,1,1,3,3,3-hexafluoro-2-propanol | 10.0 |
| Prod. Ex. 38 | poly-L-alanine/γ-methyl-L-glutamic acid 9/1 | Synthe. Ex. 6 | dichloromethane-trifluoroacetic acid 50/50 (v/v) | 8.0 |
| Prod. Ex. 39 | poly-L-alanine/γ-methyl-L-glutamic acid 6/4 | Synthe. Ex. 7 | dichloromethane-trifluoroacetic acid 50/50 (v/v) | 9.9 |
| Prod. Ex. 40 | poly-L-leucine/γ-methyl-L-glutamic acid 9/1 | Synthe. Ex. 9 | dichloromethane-trifluoroacetic acid 20/80 (v/v) | 6.7 |
| Prod. Ex. 41 | poly-L-leucine/γ-methyl-L-glutamic acid 6/4 | Synthe. Ex. 10 | dichloromethane-trifluoroacetic acid 20/80 (v/v) | 7.7 |
| Prod. Ex. 42 | poly-L-alanine/N$^\epsilon$-benzyloxycarbonyl-L-lysine 9/1 | Synthe. Ex. 12 | dichloromethane-trifluoroacetic acid 50/50 (v/v) | 5.3 |
| Prod. Ex. 43 | poly-L-alanine/N$^\epsilon$-benzyloxycarbonyl-L-lysine 6/4 | Synthe. Ex. 13 | 1,1,1,3,3,3-hexafluoro-2-propanol | 8.0 |
| Prod. Ex. 44 | poly-L-alanine/N$^\epsilon$-benzyloxycarbonyl-L-lysine 3/7 | Synthe. Ex. 14 | 1,1,1,3,3,3-hexafluoro-2-propanol | 10.0 |
| Prod. Ex. 45 | poly-L-phenylalanine/N$^\epsilon$-benzyloxycarbonyl-L-lysine 9/1 | Synthe. Ex. 17 | dichloromethane-trifluoroacetic acid 20/80 (v/v) | 2.0 |
| Prod. Ex. 46 | poly-L-phenylalanine/N$^\epsilon$-benzyloxycarbonyl-L-lysine 6/4 | Synthe. Ex. 18 | 1,1,1,3,3,3-hexafluoro-2-propanol | 7.8 |
| Prod. Ex. 47 | poly-L-phenylalanine/N$^\epsilon$-benzyloxycarbonyl-L-lysine 3/7 | Synthe. Ex. 19 | 1,1,1,3,3,3-hexafluoro-2-propanol | 10.0 |
| Prod. Ex. 48 | poly-L-alanine + poly-N$^\epsilon$-benzyloxycarbonyl-L-lysine 9 + 1 | Synthe. Ex. 1 + Synthe. Ex. 5 | dichloromethane-trifluoroacetic acid 50/50 (v/v) | 5.3 |
| Prod. Ex. 49 | poly-L-alanine + poly-N$^\epsilon$-benzyloxycarbonyl-L-lysine 6 + 4 | Synthe. Ex. 1 + Synthe. Ex. 5 | dichloromethane-trifluoroacetic acid 50/50 (v/v) | 5.3 |

TABLE 6-1-2

| Prod. Ex. | polymer constituting fiber structure | | solvent for solutionization | solution concentration (wt %) |
|---|---|---|---|---|
| Prod. Ex. 92 | poly-L-phenylalanine/benzyl-L-aspartic acid/γ-methyl-L-glutamic acid 3/2/5 | Synthe. Ex. 22 | 1,1,1,3,3,3-hexafluoro-2-propanol | 10.0 |

TABLE 6-1-2-continued

| Prod. Ex. | polymer constituting fiber structure | | solvent for solutionization | solution concentration (wt %) |
|---|---|---|---|---|
| Prod. Ex. 93 | poly-L-phenyl-alanine/benzyl-L-aspartic acid/N$^\varepsilon$-benzyloxycarbonyl-L-lysine 3/2/5 | Synthe. Ex. 23 | dichloromethane-trifluoroacetic acid 30/20 (v/v) | 12.5 |
| Prod. Ex. 94 | poly-L-leucine/L-glutamic acid 8/2 | Synthe. Ex. 24 | dichloromethane-trifluoroacetic acid 50/50 (v/v) | 8.3 |
| Prod. Ex. 95 | poly-L-leucine/N$^\varepsilon$-benzyloxycarbonyl-L-lysine 9/1 | Synthe. Ex. 25 | dichloromethane-trifluoroacetic acid 50/50 (v/v) | 8.3 |
| Prod. Ex. 96 | poly-L-leucine/N$^\varepsilon$-benzyloxycarbonyl-L-lysine 6/4 | Synthe. Ex. 26 | dichloromethane-trifluoroacetic acid 50/50 (v/v) | 13.0 |
| Prod. Ex. 97 | poly-L-leucine/L-lysine 8/2 | Synthe. Ex. 27 | dichloromethane-trifluoroacetic acid 50/50 (v/v) | 10.0 |
| Prod. Ex. 98 | poly-L-leucine/L-glutamic acid/L-lysine 8/1/1 | Synthe. Ex. 28 | dichloromethane-trifluoroacetic acid 50/50 (v/v) | 8.3 |

Production Example 50

Poly-L-Valine Film

Poly-L-valine synthesized in Synthetic Example 2 was dissolved in trifluoroacetic acid to give a 6.7 wt % poly-L-valine solution. This solution was applied to a fluorine polymer film at a thickness of 0.80 mm, and dried at room temperature for 24 hr and then at room temperature under reduced pressure for 24 hr to give a transparent film.

Production Examples 51-60

Various Polyamino Acid Films

In the same manner as in Production Example 50, solutions of various polyamino acids synthesized in Synthetic Examples 3, 6-8, 11-12, 15-16 and 20-21 were prepared under the conditions of Table 6-2-1 to give films.

Production Examples 99-104

Various Polyamino Acid Films

In the same manner as in Production Example 50, solutions of various polyamino acids synthesized in Synthetic Examples 29-32, 22 and 23 were prepared under the conditions of Table 6-2-2 to give films.

TABLE 6-2-1

| Prod. Ex. | polymer constituting film | | solvent for solutionization | solution concentration (wt %) |
|---|---|---|---|---|
| Prod. Ex. 50 | poly-L-valine | Synthe. Ex. 2 | trifluoroacetic acid | 6.7 |
| Prod. Ex. 51 | poly-$\gamma$-methyl-L-glutamic acid | Synthe. Ex. 3 | 1,2-dichloroethane | 12.2 |
| Prod. Ex. 52 | poly-L-alanine/$\gamma$-methyl-L-glutamic acid 9/1 | Synthe. Ex. 6 | 1,1,1,3,3,3-hexafluoro-2-propanol | 6.6 |
| Prod. Ex. 53 | poly-L-alanine/$\gamma$-methyl-L-glutamic acid 6/4 | Synthe. Ex. 7 | 1,1,1,3,3,3-hexafluoro-2-propanol | 8.0 |
| Prod. Ex. 54 | poly-L-alanine/$\gamma$-methyl-L-glutamic acid 3/7 | Synthe. Ex. 8 | 1,2-dichloroethane | 7.2 |
| Prod. Ex. 55 | poly-L-phenyl-alanine/$\gamma$-methyl-L-glutamic acid 6/4 | Synthe. Ex. 11 | 1,1,1,3,3,3-hexafluoro-2-propanol | 10.0 |
| Prod. Ex. 56 | poly-L-alanine/N$^\varepsilon$-benzyloxycarbonyl-L-lysine 9/1 | Synthe. Ex. 12 | trifluoroacetic acid | 6.7 |
| Prod. Ex. 57 | poly-L-valine/N$^\varepsilon$-benzyloxycarbonyl-L-lysine 6/4 | Synthe. Ex. 15 | trifluoroacetic acid | 6.7 |
| Prod. Ex. 58 | poly-L-isoleucine/N$^\varepsilon$-benzyloxycarbonyl-L-lysine 6/4 | Synthe. Ex. 16 | trifluoroacetic acid | 6.7 |
| Prod. Ex. 59 | poly-L-valine/L-phenylalanine 5/5 | Synthe. Ex. 20 | dichloromethane-trifluoroacetic acid 50/50 (v/v) | 6.7 |
| Prod. Ex. 60 | poly-L-leucine/L-phenylalanine 5/5 | Synthe. Ex. 21 | dichloromethane-trifluoroacetic acid 50/50 (v/v) | 6.7 |

TABLE 6-2-2

| Prod. Ex. | polymer constituting film | | solvent for solutionization | solution concentration (wt %) |
|---|---|---|---|---|
| Prod. Ex. 99 | poly-$\gamma$-methyl-L-glutamic acid/L-glutamic acid 8/2 | Synthe. Ex. 29 | trifluoroacetic acid | 6.5 |
| Prod. Ex. 100 | (poly-L-N$^\varepsilon$-benzyloxycarbonyl-L-lysine/N$^\varepsilon$-acetyl-L-lysine 6/4) + (poly-$\gamma$-methyl-L-glutamic acid) 1 + 1 | Synthe. Ex. 30 | trifluoroacetic acid | 2.5 |
| Prod. Ex. 101 | poly-L-valine/$\gamma$-methyl-L-glutamic acid 6/4 | Synthe. Ex. 31 | trifluoroacetic acid | 6.7 |
| Prod. Ex. 102 | poly-L-isoleucine/$\gamma$-methyl-L-glutamic acid 6/4 | Synthe. Ex. 32 | trifluoroacetic acid | 6.7 |
| Prod. Ex. 103 | poly-L-phenylalanine/benzyl-L-aspartic acid/$\gamma$-methyl-L-glutamic acid 3/2/5 | Synthe. Ex. 22 | 1,2-dichloroethane | 7.4 |
| Prod. Ex. 104 | poly-L-phenyl-alanine/benzyl-L-aspartic acid/N$^\varepsilon$-benzyloxycarbonyl-L-lysine 3/2/5 | Synthe. Ex. 23 | 1,2-dichloroethane | 9.4 |

Production Example 61

Poly-N$^\varepsilon$-benzyloxycarbonyl-L-lysine Coating

Poly-N$^\varepsilon$-benzyloxycarbonyl-L-lysine synthesized in Synthetic Example 5 was dissolved in chloroform to give a 10.0 wt % poly-N$^\varepsilon$-benzyloxycarbonyl-L-lysine solution. This solution was applied to a circular cover glass (manufactured by Thermo Fisher Scientific K.K., φ12 mm) at a thickness of 0.80 mm, and heat dried at 80° C. for 15 min to give a coating.

Production Examples 62-64

Various Polyamino Acid Coatings

In the same manner as in Production Example 61, solutions of various polyamino acids synthesized in Synthetic Examples 12, 14 and 18 were prepared under the conditions of Table 6-3-1 to give coatings.

Production Examples 105-109

Various Polyamino Acid Coatings

In the same manner as in Production Example 61, solutions of various polyamino acids synthesized in Synthetic Examples 33-37 were prepared under the conditions of Table 6-3-2 to give coatings.

TABLE 6-3-1

| Prod. Ex. | polymer constituting coating | solvent for solutionization | solution concentration (wt %) |
|---|---|---|---|
| Prod. Ex. 61 | poly-$N^\epsilon$-benzyloxycarbonyl-L-lysine | Synthe. Ex. 5 | 1,1,1,3,3,3-hexafluoro-2-propanol | 10.0 |
| Prod. Ex. 62 | poly-L-alanine/$N^\epsilon$-benzyloxycarbonyl-L-lysine 6/4 | Synthe. Ex. 12 | 1,1,1,3,3,3-hexafluoro-2-propanol | 8.0 |
| Prod. Ex. 63 | poly-L-alanine/$N^\epsilon$-benzyloxycarbonyl-L-lysine 3/7 | Synthe. Ex. 14 | 1,1,1,3,3,3-hexafluoro-2-propanol | 8.0 |
| Prod. Ex. 64 | poly-L-phenylalanine/$N^\epsilon$-benzyloxycarbonyl-L-lysine 6/4 | Synthe. Ex. 18 | 1,1,1,3,3,3-hexafluoro-2-propanol | 10.0 |

TABLE 6-3-2

| Prod. Ex. | polymer constituting coating | solvent for solutionization | solution concentration (wt %) |
|---|---|---|---|
| Prod. Ex. 105 | poly-L-glycine | Synthe. Ex. 33 | trifluoroacetic acid | 3.3 |
| Prod. Ex. 106 | poly-L-$N^\epsilon$-benzyloxycarbonyl-L-lysine/L-lysine 6/4 | Synthe. Ex. 34 | chloroform | 2.0 |
| Prod. Ex. 107 | poly-$N^\epsilon$-benzyloxycarbonyl-L-lysine/$N^\epsilon$-t-butoxycarbonyl-guanidino-L-lysine 6/4 | Synthe. Ex. 35 | chloroform | 1.8 |
| Prod. Ex. 108 | poly-L-glycine/γ-methyl-L-glutamic acid/L-glutamic acid 5/3/2 | Synthe. Ex. 36 | trifluoroacetic acid | 1.5 |
| Prod. Ex. 109 | poly-L-leucine/L-glutamic acid/L-lysine 6/1/3 | Synthe. Ex. 37 | trifluoroacetic acid | 6.7 |

Production Example 65

Surface Saponification-Treated poly-γ-methyl-L-glutamic Acid Fiber Structure

The poly-γ-methyl-L-glutamic acid fiber structure produced in Production Example 35 was mounted on a circular cover glass or cover slip (diameter 12-13 mm) (Thermo Scientific Inc., Nunc Thermanox Plastic Coverslips). The mounted sample was immersed in 0.5N potassium hydroxide ethanol solution (manufactured by KOKUSAN CHEMICAL) for 90 min. After the completion of immersion, the sample was immersed in ethanol, pure water, 0.5N aqueous hydrochloric acid solution (KOKUSAN CHEMICAL) and pure water in this order, and dried at room temperature under reduced pressure to give a surface-treated fiber structure.

Production Example 66

Surface HBr-Treated poly-$N^\epsilon$-benzyloxycarbonyl-L-lysine Fiber Structure The poly-$N^\epsilon$-benzyloxycarbonyl-L-lysine fiber structure produced in Production Example 37 was mounted on a circular cover glass or cover slip (diameter 12-13 mm) (Thermo Scientific Inc., Nunc Thermanox Plastic Coverslips). The mounted sample was immersed in a HBr (manufactured by TOKYO CHEMICAL INDUSTRY, 30% acetic acid solution) solution diluted 400-fold with diethylether (manufactured by KANTO CHEMICAL) for 4.5 min. After the completion of immersion, the sample was immersed in pure water, ethanol, 2.0M aqueous sodium carbonate solution (manufactured by KOKUSAN CHEMICAL) and pure water in this order, and dried at room temperature under reduced pressure to give a surface-treated fiber structure.

Production Examples 67-70

Various Surface Saponification-Treated Polyamino Acid Fiber Structures

In the same manner as in Production Example 65, the fiber structures produced in Production Examples 38-41 were subjected to the surface saponification treatment method.

Production Examples 110-114

Various Surface Saponification-Treated Polyamino Acid Fiber Structures

In the same manner as in Production Example 65, the fiber structures produced in Production Examples 12-15 were subjected to the surface saponification treatment method.

Production Examples 71-78

Various Surface HBr-Treated Polyamino Acid Fiber Structures

In the same manner as in Production Example 66, the fiber structures produced in Production Examples 42-49 were subjected to the surface HBr treatment method.

Production Examples 115-119

Various Surface HBr-Treated Polyamino Acid Fiber Structures

In the same manner as in Production Example 66, the fiber structures produced in Production Examples 19, 10, 93, 95 and 96 were subjected to the surface HBr treatment method.

Production Example 79

Surface Saponification-Treated
poly-γ-methyl-L-glutamic Acid Film

The poly-γ-methyl-L-glutamic acid film produced in Production Example 51 was immersed in a 0.5N potassium hydroxide ethanol solution for 90 min. After the completion of immersion, the sample was immersed in ethanol, pure water, 0.5N aqueous hydrochloric acid solution and pure water in this order, and dried at room temperature under reduced pressure to give a surface-treated film.

Production Examples 80-83

Various Surface Saponification-Treated Polyamino Acid Films

In the same manner as in Production Example 79, the films produced in Production Examples 52-55 were subjected to the surface saponification treatment method.

Production Examples 120-122

Various Surface Saponification-Treated Polyamino Acid Films

In the same manner as in Production Example 79, the films produced in Production Examples 101-103 were subjected to the surface saponification treatment method.

Production Example 84

Surface HBr-Treated poly-L-alanine/N$^\epsilon$-benzyloxycarbonyl-L-lysine Copolymer (Molar Ratio: 9/1) Film The poly-L-alanine/N$^\epsilon$-benzyloxycarbonyl-L-lysine copolymer film (molar ratio: 9/1) produced in Production Example 56 was mounted on a circular cover glass (diameter 12-13 mm). The mounted sample was immersed in a HBr (30% acetic acid solution) solution diluted 400-fold with diethylether (manufactured by KANTO CHEMICAL) for 4.5 min. After the completion of immersion, the sample was immersed in pure water, ethanol, 2.0M aqueous sodium carbonate solution and pure water in this order, and dried at room temperature under reduced pressure to give a surface-treated film.

Production Examples 85, 86

Various Surface HBr-Treated Polyamino Acid Films

In the same manner as in Production Example 84, the films produced in Production Examples 57 and 58 were subjected to the surface HBr treatment method.

Production Example 123

Various Surface HBr-Treated Polyamino Acid Film

In the same manner as in Production Example 84, the film produced in Production Example 104 was subjected to the surface HBr treatment method.

Production Example 87

Surface HBr-Treated
poly-N$^\epsilon$-benzyloxycarbonyl-L-lysine Coating

The poly-N$^\epsilon$-benzyloxycarbonyl-L-lysine coating produced in Production Example 61 was immersed in a HBr (30% acetic acid solution) solution diluted 400-fold with diethylether for 4.5 min. After the completion of immersion, the sample was immersed in pure water, ethanol, 2.0M aqueous sodium carbonate solution and pure water in this order, and dried at room temperature under reduced pressure to give a surface-treated coating.

Production Examples 88-90

Various Surface HBr-Treated Polyamino Acid Coatings

In the same manner as in Production Example 87, the coatings produced in Production Examples 62-64 were subjected to the surface HBr treatment method.

The fiber structures produced in Production Examples 33-49, 65-78 were measured for the average fiber diameter and protecting group content according to the following. The results thereof are shown in Table 7-1-1. In addition, the average fiber diameter and protecting group content of the fiber structures produced Production Examples 2, 4, 12-15, 19-23, 92-98 and 110-119 are shown in Table 7-1-2.

The films produced in Production Examples 50-60, 79-86 were measured for the film thickness and protecting group content according to the following. The results thereof are shown in Table 7-2-1. In addition, the film thickness of the films produced Production Examples 99, 100-104, 120-123 are shown in Table 7-2-2.

The coatings produced in Production Examples 61-64, 87-90 were measured for the film thickness and protecting group content according to the following. The results thereof are shown in Table 7-3-1. In addition, the film thickness of the films produced Production Examples 30, 105-109 are shown in Table 7-3-2.

[Average Fiber Diameter of Fiber Structure]

After confirmation of the uniformity of the surface of the obtained fiber structure by visual observation, a part of the surface was collected and subjected to the surface observation under a scanning electron microscope (SEM, Hitachi Corporation, S-4800). First, the whole measurement sample was reviewed at magnification ×500 and, after confirmation of the uniformity of the surface, the magnification was changed to ×1,000 or ×5,000, and photograph was taken. The obtained photograph was placed such that it was wider than it was tall, and the lateral direction and longitudinal direction were divided into 5 equal parts and 2 equal parts, respectively, to give 10 sections with equal areas. The fibers in focus were selected from those at the center or nearest to the center of each section, and the diameter thereof was measured. The average thereof was determined and taken as the average fiber diameter.

[Film Thickness of Various Formation-Processed Products]

After confirmation of the uniformity of the surface of the obtained various formation-processed products, the measurement was performed at 3-5 positions using a micrometer (Mitsutoyo Corporation, MDC-25MJ), and the average thereof was determined and taken as the film thickness.

[Calculation of Protecting Group Content of Polyamino Acid Formation-Processed Product Containing γ-Methyl-L-Glutamic Acid Residue]

Poly-γ-methyl-L-glutamic acids known to have 4 kinds of methylester contents (53%, 54%, 81%, 100%) were respectively processed to form films, which were subjected to FT-IR Attenuated Total Reflection measurement (FT-IR-ATR). For the measurement, IR Prestige21 manufactured by Shimadzu Corporation and DuraSampl IR II manufactured by Smiths as an ATR measurement device were used. The measurement depth $d_p$ can be obtained by the following calculation formula. The prism refractive index Nc of DuraSampl IR II is 2.4, λ is wavelength, and Ns is refractive index of the sample.

$$d_p = \lambda/(2\pi Nc(\sin^2\theta - (Ns/Nc)))^{1/2})$$

The peak area was measured from the obtained spectrum, and the conversion formula for calculation of the methyl ester group content was obtained from the ratio of the peak area derived from the methylester group to the peak area derived from the main chain (α bond) amide group. Then, a polyamino acid formation-processed product containing a γ-methyl-L-glutamic acid residue and a saponification-treated product thereof were subjected to FT-IR Attenuated Total Reflection method spectrum measurement and the methylester group content was calculated from the above-mentioned conversion formula.

[Calculation of Protecting Group Content of Polyamino Acid Formation-Processed Product Containing N$^\epsilon$-Benzyloxycarbonyl-L-Lysine Residue]

The FT-IR Attenuated Total Reflection measurement method spectrum of poly-N$^\epsilon$-benzyloxycarbonyl-L-lysine known to have 3 kinds of N$^\epsilon$-benzyloxycarbonyl contents (60%, 85%, 100%) was measured. The peak height was measured from the obtained spectrum, and the conversion formula for calculation of the benzyloxycarbonyl group content was obtained from the ratio of the peak height derived from the benzyloxycarbonyl group to the peak height derived from the main chain (α bond) amide group. Then, a polyamino acid formation-processed product containing a N$^\epsilon$-benzyloxycarbonyl-L-lysine residue and a HBr-treated product thereof were subjected to FT-IR Attenuated Total Reflection method spectrum measurement and the benzyloxycarbonyl group content was calculated from the above-mentioned conversion formula.

TABLE 7-1-1

| Prod. Ex. | polymer constituting fiber structure | average fiber diameter (nm) | surface treatment | protecting group content (%) |
|---|---|---|---|---|
| Prod. Ex. 33 | poly-L-alanine | 144 | — | — |
| Prod. Ex. 34 | poly-L-valine | 320 | — | — |
| Prod. Ex. 35 | poly-γ-methyl-L-glutamic acid | 826 | — | — |
| Prod. Ex. 36 | poly-γ-benzyl-L-glutamic acid | 1854 | — | — |
| Prod. Ex. 37 | poly-N$^\epsilon$-benzyloxycarbonyl-L-lysine | 300 | — | — |
| Prod. Ex. 38 | poly-L-alanine/γ-methyl-L-glutamic acid 9/1 | 610 | — | — |
| Prod. Ex. 39 | poly-L-alanine/γ-methyl-L-glutamic acid 6/4 | 332 | — | — |
| Prod. Ex. 40 | poly-L-leucine/γ-methyl-L-glutamic acid 9/1 | 472 | — | — |
| Prod. Ex. 41 | poly-L-leucine/γ-methyl-L-glutamic acid 6/4 | 520 | — | — |
| Prod. Ex. 42 | poly-L-alanine/N$^\epsilon$-benzyloxycarbonyl-L-lysine 9/1 | 326 | — | — |
| Prod. Ex. 43 | poly-L-alanine/N$^\epsilon$-benzyloxycarbonyl-L-lysine 6/4 | 730 | — | — |
| Prod. Ex. 44 | poly-L-alanine/N$^\epsilon$-benzyloxycarbonyl-L-lysine 3/7 | 386 | — | — |
| Prod. Ex. 45 | poly-L-phenylalanine/N$^\epsilon$-benzyloxycarbonyl-L-lysine 9/1 | 326 | — | — |
| Prod. Ex. 46 | poly-L-phenylalanine/N$^\epsilon$-benzyloxycarbonyl-L-lysine 6/4 | 386 | — | — |
| Prod. Ex. 47 | poly-L-phenylalanine/N$^\epsilon$-benzyloxycarbonyl-L-lysine 3/7 | 778 | — | — |
| Prod. Ex. 48 | poly-L-alanine + poly-N$^\epsilon$-benzyloxycarbonyl-L-lysine 9 + 1 | 210 | — | — |
| Prod. Ex. 49 | poly-L-alanine + poly-N$^\epsilon$-benzyloxycarbonyl-L-lysine 6 + 4 | 184 | — | — |
| Prod. Ex. 65 | poly-γ-methyl-L-glutamic acid surface KOH treatment | 1480 | KOH | 99.5< |
| Prod. Ex. 66 | poly-N$^\epsilon$-benzyloxycarbonyl-L-lysine surface HBr treatment | 462 | HBr | 98.0< |
| Prod. Ex. 67 | poly-L-alanine/γ-methyl-L-glutamic acid 9/1 surface KOH treatment | 740 | KOH | 78.0 |
| Prod. Ex. 68 | poly-L-alanine/γ-methyl-L-glutamic acid 6/4 surface KOH treatment | 1464 | KOH | 98.0 |
| Prod. Ex. 69 | poly-L-leucine/γ-methyl-L-glutamic acid 9/1 surface KOH treatment | 488 | KOH | — |
| Prod. Ex. 70 | poly-L-leucine/γ-methyl-L-glutamic acid 6/4 surface KOH treatment | 768 | HBr | 99.5< |
| Prod. Ex. 71 | poly-L-alanine/N$^\epsilon$-benzyloxycarbonyl-L-lysine 9/1 surface HBr treatment | 384 | HBr | 69.0 |
| Prod. Ex. 72 | poly-L-alanine/N$^\epsilon$-benzyloxycarbonyl-L-lysine 6/4 surface HBr treatment | 614 | HBr | 87.0 |
| Prod. Ex. 73 | poly-L-alanine/N$^\epsilon$-benzyloxycarbonyl-L-lysine 3/7 surface HBr treatment | 566 | HBr | 98.0< |
| Prod. Ex. 74 | poly-L-phenylalanine/N$^\epsilon$-benzyloxycarbonyl-L-lysine 9/1 surface HBr treatment | 402 | HBr | 30.0> |
| Prod. Ex. 75 | poly-L-phenylalanine/N$^\epsilon$-benzyloxycarbonyl-L-lysine 6/4 surface HBr treatment | 538 | HBr | 71.0 |
| Prod. Ex. 76 | poly-L-phenylalanine/N$^\epsilon$-benzyloxycarbonyl-L-lysine 3/7 surface HBr treatment | 854 | HBr | 98.0< |
| Prod. Ex. 77 | poly-L-alanine + poly-N$^\epsilon$-benzyloxycarbonyl-L-lysine 9 + 1 surface HBr treatment | 268 | HBr | — |
| Prod. Ex. 78 | poly-L-alanine + poly-N$^\epsilon$-benzyloxycarbonyl-L-lysine 6 + 4 surface HBr treatment | 210 | HBr | 96.0 |

TABLE 7-1-2

| Prod. Ex. | polymer constituting fiber structure | average fiber diameter (nm) | surface treatment | protecting group content (%) |
|---|---|---|---|---|
| Prod. Ex. 2 | poly-L-leucine | 99 | — | — |
| Prod. Ex. 4 | poly-β-benzyl-L-aspartic acid | 1281 | — | — |

TABLE 7-1-2-continued

| Prod. Ex. | polymer constituting fiber structure | average fiber diameter (nm) | surface treatment | protecting group content (%) |
|---|---|---|---|---|
| Prod. Ex. 12 | poly-L-valine/γ-methyl-L-glutamic acid 6/4 | 258 | — | — |
| Prod. Ex. 13 | poly-L-isoleucine/γ-methyl-L-glutamic acid 6/4 | 132 | — | — |
| Prod. Ex. 14 | poly-L-phenylalanine/γ-methyl-L-glutamic acid 9/1 | 326 | — | — |
| Prod. Ex. 15 | poly-L-phenylalanine/γ-methyl-L-glutamic acid 6/4 | 386 | — | — |
| Prod. Ex. 19 | poly-L-valine/N$^\epsilon$-benzyloxycarbonyl-L-lysine 6/4 | 316 | — | — |
| Prod. Ex. 20 | poly-L-isoleucine/N$^\epsilon$-benzyloxycarbonyl-L-lysine 6/4 | 182 | — | — |
| Prod. Ex. 21 | poly-L-leucine/L-phenylalanine 1/1 | 1520 | — | — |
| Prod. Ex. 22 | poly-L-valine/L-phenylalanine 1/1 | 1780 | — | — |
| Prod. Ex. 23 | poly-L-glutamine/γ-methyl-L-glutamic acid | 363 | — | — |
| Prod. Ex. 92 | poly-L-phenylalanine/benzyl-L-aspartic acid/γ-methyl-L-glutamic acid 3/2/5 | 464 | — | — |
| Prod. Ex. 93 | poly-L-phenylalanine/benzyl-L-aspartic acid/N$^\epsilon$-benzyloxycarbonyl-L-lysine 3/2/5 | 474 | — | — |
| Prod. Ex. 94 | poly-L-leucine/L-glutamic acid 8/2 | 474 | — | — |
| Prod. Ex. 95 | poly-L-leucine/N$^\epsilon$-benzyloxycarbonyl-L-lysine 9/1 | 269 | — | — |
| Prod. Ex. 96 | poly-L-leucine/N$^\epsilon$-benzyloxycarbonyl-L-lysine 6/4 | 752 | — | — |
| Prod. Ex. 97 | poly-L-leucine/L-lysine 8/2 | 480 | — | — |
| Prod. Ex. 98 | poly-L-leucine/L-glutamic acid/L-lysine 8/1/1 | 524 | — | — |
| Prod. Ex. 110 | poly-L-valine/γ-methyl-L-glutamic acid 6/4 surface KOH treatment | 419 | KOH | not measured |
| Prod. Ex. 111 | poly-L-isoleucine/γ-methyl-L-glutamic acid 6/4 surface KOH treatment | 270 | KOH | not measured |
| Prod. Ex. 112 | poly-L-phenylalanine/γ-methyl-L-glutamic acid 9/1 surface KOH treatment | 326 | KOH | not measured |
| Prod. Ex. 113 | poly-L-phenylalanine/γ-methyl-L-glutamic acid 6/4 surface KOH treatment | 865 | KOH | not measured |
| Prod. Ex. 114 | poly-L-phenylalanine/benzyl-L-aspartic acid/γ-methyl-L-glutamic acid 3/2/5 surface KOH treatment | 464 | KOH | not measured |
| Prod. Ex. 115 | poly-L-valine/N$^\epsilon$-benzyloxycarbonyl-L-lysine 6/4 surface HBr treatment | 254 | HBr | not measured |
| Prod. Ex. 116 | poly-L-isoleucine/N$^\epsilon$-benzyloxycarbonyl-L-lysine 6/4 surface HBr treatment | 228 | HBr | not measured |
| Prod. Ex. 117 | poly-L-phenylalanine/benzyl-L-aspartic acid/N$^\epsilon$-benzyloxycarbonyl-L-lysine 3/2/5 surface HBr treatment | 474 | HBr | not measured |
| Prod. Ex. 118 | poly-L-leucine/N$^\epsilon$-benzyloxycarbonyl-L-lysine 9/1 surface HBr treatment | 899 | HBr | not measured |
| Prod. Ex. 119 | poly-L-leucine/N$^\epsilon$-benzyloxycarbonyl-L-lysine 6/4 surface HBr treatment | 840 | HBr | not measured |

TABLE 7-2-1

| Prod. Ex. | polymer constituting film | film thickness (μm) | surface treatment | protecting group content (%) |
|---|---|---|---|---|
| Prod. Ex. 50 | poly-L-valine | 104.8 | — | — |
| Prod. Ex. 51 | poly-γ-methyl-L-glutamic acid | 47.2 | — | — |
| Prod. Ex. 52 | poly-L-alanine/γ-methyl-L-glutamic acid 9/1 | 24.2 | — | — |
| Prod. Ex. 53 | poly-L-alanine/γ-methyl-L-glutamic acid 6/4 | 23.7 | — | — |
| Prod. Ex. 54 | poly-L-alanine/γ-methyl-L-glutamic acid 3/7 | 32.7 | — | — |
| Prod. Ex. 55 | poly-L-phenylalanine/γ-methyl-L-glutamic acid 6/4 | 63.3 | — | — |
| Prod. Ex. 56 | poly-L-alanine/N$^\epsilon$-benzyloxycarbonyl-L-lysine 9/1 | 24.2 | — | — |
| Prod. Ex. 57 | poly-L-valine/N$^\epsilon$-benzyloxycarbonyl-L-lysine 6/4 | 27.6 | — | — |
| Prod. Ex. 58 | poly-L-isoleucine/N$^\epsilon$-benzyloxycarbonyl-L-lysine 6/4 | 19.2 | — | — |
| Prod. Ex. 59 | poly-L-valine/L-phenylalanine 5/5 | 61.4 | — | — |
| Prod. Ex. 60 | poly-L-valine/L-phenylalanine 5/5 | 64.4 | — | — |
| Prod. Ex. 79 | poly-γ-methyl-L-glutamic acid surface KOH treatment | 42.2 | KOH | 99.5< |
| Prod. Ex. 80 | poly-L-alanine/γ-methyl-L-glutamic acid 9/1 surface KOH treatment | — | KOH | 78.0 |
| Prod. Ex. 81 | poly-L-alanine/γ-methyl-L-glutamic acid 6/4 surface KOH treatment | — | KOH | 98.0 |
| Prod. Ex. 82 | poly-L-alanine/γ-methyl-L-glutamic acid 3/7 surface KOH treatment | — | KOH | 99.5< |
| Prod. Ex. 83 | poly-L-phenylalanine/γ-methyl-L-glutamic acid 6/4 surface KOH treatment | — | KOH | 94.0 |

TABLE 7-2-1-continued

| Prod. Ex. | polymer constituting film | film thickness (μm) | surface treatment | protecting group content (%) |
|---|---|---|---|---|
| Prod. Ex. 84 | poly-L-alanine/N$^\epsilon$-benzyloxycarbonyl-L-lysine 9/1 surface HBr treatment | — | HBr | 69.0 |
| Prod. Ex. 85 | poly-L-valine/N$^\epsilon$-benzyloxycarbonyl-L-lysine 6/4 surface HBr treatment | — | HBr | 96.0 |
| Prod. Ex. 86 | poly-L-isoleucine/N$^\epsilon$-benzyloxycarbonyl-L-lysine 6/4 surface HBr treatment | — | HBr | 96.0 |

TABLE 7-2-2

| Prod. Ex. | polymer constituting film | film thickness (μm) | surface treatment | protectting group content (%) |
|---|---|---|---|---|
| Prod. Ex. 99 | poly-γ-methyl-L-glutamic acid/L-glutamic acid 8/2 | not measured | — | — |
| Prod. Ex. 100 | (poly-L-N$^\epsilon$-benzyloxycarbonyl-L-lysine/N$^\epsilon$-acetyl-L-lysine 6/4) + (poly-γ-methyl-L-glutamic acid) 1 + 1 | not measured | — | — |
| Prod. Ex. 101 | poly-L-valine/γ-methyl-L-glutamic acid 6/4 | 59.8 | — | — |
| Prod. Ex. 102 | poly-L-isoleucine/γ-methyl-L-glutamic acid 6/4 | 39.6 | — | — |
| Prod. Ex. 103 | poly-L-phenylalanine/benzyl-L-aspartic acid/γ-methyl-L-glutamic acid 3/2/5 | 45.2 | — | — |
| Prod. Ex. 104 | poly-L-phenylalanine/benzyl-L-aspartic acid/N$^\epsilon$-benzyloxycarbonyl-L-lysine 3/2/5 | 36.2 | — | — |
| Prod. Ex. 120 | poly-L-valine/γ-methyl-L-glutamic acid 6/4 surface KOH treatment | 46.4 | KOH | not measured |
| Prod. Ex. 121 | poly-L-isoleucine/γ-methyl-L-glutamic acid 6/4 surface KOH treatment | 43.2 | KOH | not measured |
| Prod. Ex. 122 | poly-L-phenylalanine/benzyl-L-aspartic acid/γ-methyl-L-glutamic acid 3/2/5 surface KOH treatment | 52.4 | KOH | not measured |
| Prod. Ex. 123 | poly-L-phenylalanine/benzyl-L-aspartic acid/N$^\epsilon$-benzyloxycarbonyl-L-lysine 3/2/5 surface HBr treatment | 36.2 | HBr | not measured |

TABLE 7-3-1

| Prod. Ex. | polymer constituting coating | film thickness (μm) | surface treatment | protecting group content (%) |
|---|---|---|---|---|
| Prod. Ex. 61 | poly-N$^\epsilon$-benzyloxycarbonyl-L-lysine | 22.4 | — | — |
| Prod. Ex. 62 | poly-L-alanine/N$^\epsilon$-benzyloxycarbonyl-L-lysine 6/4 | 56.5 | — | — |
| Prod. Ex. 63 | poly-L-alanine/N$^\epsilon$-benzyloxycarbonyl-L-lysine 3/7 | 58.9 | — | — |
| Prod. Ex. 64 | poly-L-phenylalanine/N$^\epsilon$-benzyloxycarbonyl-L-lysine 6/4 | 73.3 | — | — |
| Prod. Ex. 87 | poly-N$^\epsilon$-benzyloxycarbonyl-L-lysine surface HBr treatment | — | HBr | 98.0< |
| Prod. Ex. 88 | poly-L-alanine/N$^\epsilon$-benzyloxycarbonyl-L-lysine 6/4 surface HBr treatment | — | HBr | 89.0 |
| Prod. Ex. 89 | poly-L-alanine/N$^\epsilon$-benzyloxycarbonyl-L-lysine 3/7 surface HBr treatment | — | HBr | 98.0< |
| Prod. Ex. 90 | poly-L-phenylalanine/N$^\epsilon$-benzyloxycarbonyl-L-lysine 6/4 surface HBr treatment | — | HBr | 98.0< |

TABLE 7-3-2

| Prod. Ex. | polymer constituting coating | film thickness (μm) | surface treatment | protecting group content (%) |
|---|---|---|---|---|
| Prod. Ex. 105 | poly-L-glycine | 1.0 | — | — |
| Prod. Ex. 106 | poly-L-N$^\epsilon$-benzyloxycarbonyl-L-lysine/L-lysine 6/4 | not measured | — | — |
| Prod. Ex. 107 | Poly-N$^\epsilon$-benzyloxycarbonyl-L-lysine/N$^\epsilon$-t-butoxycarbonylguanidino-L-lysine 6/4 | 25.8 | — | — |
| Prod. Ex. 108 | poly-L-glycine/γ-methyl-L-glutamic acid/L-glutamic acid 5/3/2 | 13.7 | — | — |
| Prod. Ex. 109 | poly-L-leucine/L-glutamic acid/L-lysine 6/1/3 | 120.8 | — | — |
| Prod. Ex. 30 | chitosan | not measured | — | — |

The cell adhesion effect and cell differentiation promoting effect using the fiber structures, films and coatings obtained as mentioned above were evaluated.

[Evaluation 8] Evaluation of Cell Adhesion Effect

The various polyamino acid formation-processed products shown in Production Examples 33-91 were each mounted on a circular cover glass or cover slip with a diameter of 12-13 mm (Thermo Scientific Inc., Nunc Thermanox Plastic Coverslips), as necessary, and set on a 24-well culture plate (Nippon Becton Dickinson Company, Ltd., Falcon culture plate). As a control, a 24-well culture plate coated with collagen (Nippon Becton Dickinson Company, Ltd., Falcon collagen-coated culture plate) was used. For sterilization, they were immersed in a 70% aqueous ethanol solution, and washed with phosphate buffered saline (Takara Bio, Inc., PBS(−)). Human bone marrow mesenchymal stem cells (Lonza, Human Mesenchymal Stem Cell) were suspended in a mesenchymal stem cell medium (Lonza, MSCGM) or Dulbecco's Modified Eagle Medium (Invitrogen Corporation, GIBCO DMEM) supplemented with inactivated fetal bovine serum (Invitrogen Corporation, GIBCO FBS) and penicillin-streptomycin (Sigma-Aldrich Corporation), plated at 20,000 cells/well, and cultured at 5% CO$_2$/37° C. in an incubator (Thermo Scientific Inc., Forma Incubator) for 3 days. After culture, the medium was removed and the cells were lysed in a citric acid (NACALAI TESQUE, INC.)-sodium chloride (NACALAI TESQUE, INC.) buffer containing sodium lauryl sulfate (NACALAI TESQUE, INC.). Thereto was added Bisbenzimide H33258 Fluorochrome Trihydrochloride DMSO solution (NACALAI TESQUE, INC.), and cellular DNA was quantified to obtain the number of cells showing adhesion growth on the polyamino acid formation-processed product. The evaluation criteria are as described below.

+++: amount of cellular DNA not less than 90% than that of control

++: amount of cellular DNA not less than 70% and less than 90% than that of control +: amount of cellular DNA not less than 50% and less than 70% than that of control These results are shown in Table 8.

TABLE 8

| Prod. Ex. | constituting polymer | form | evaluation 8 adhesion effect |
|---|---|---|---|
| Prod. Ex. 35 | poly-γ-methyl-L-glutamic acid | fiber structure | + |
| Prod. Ex. 45 | poly-L-phenylalanine/$N^\epsilon$-benzyloxycarbonyl-L-lysine 9/1 | fiber structure | + |
| Prod. Ex. 46 | poly-L-phenylalanine/$N^\epsilon$-benzyloxycarbonyl-L-lysine 6/4 | fiber structure | + |
| Prod. Ex. 47 | poly-L-phenylalanine/$N^\epsilon$-benzyloxycarbonyl-L-lysine 3/7 | fiber structure | + |
| Prod. Ex. 65 | poly-γ-methyl-L-glutamic acid KOH treatment | fiber structure | ++ |
| Prod. Ex. 66 | poly-$N^\epsilon$-benzyloxycarbonyl-L-lysine HBr treatment | fiber structure | + |
| Prod. Ex. 72 | poly-L-alanine/$N^\epsilon$-benzyloxycarbonyl-L-lysine 6/4 HBr treatment | fiber structure | + |
| Prod. Ex. 73 | poly-L-alanine/$N^\epsilon$-benzyloxycarbonyl-L-lysine 3/7 HBr treatment | fiber structure | ++ |
| Prod. Ex. 74 | poly-L-phenylalanine/$N^\epsilon$-benzyloxycarbonyl-L-lysine 9/1 HBr treatment | fiber structure | + |
| Prod. Ex. 76 | poly-L-phenylalanine/$N^\epsilon$-benzyloxycarbonyl-L-lysine 3/7 HBr treatment | fiber structure | + |
| Prod. Ex. 50 | poly-L-valine | film | + |
| Prod. Ex. 51 | poly-γ-methyl-L-glutamic acid | film | +++ |
| Prod. Ex. 54 | poly-L-alanine/γ-methyl-L-glutamic acid 3/7 | film | + |
| Prod. Ex. 57 | poly-L-valine/$N^\epsilon$-benzyloxycarbonyl-L-lysine 6/4 | film | + |
| Prod. Ex. 58 | poly-L-isoleucine/$N^\epsilon$-benzyloxycarbonyl-L-lysine 6/4 | film | ++ |
| Prod. Ex. 59 | poly-L-valine/L-phenylalanine 5/5 | film | +++ |
| Prod. Ex. 60 | poly-L-leucine/L-phenylalanine 5/5 | film | + |
| Prod. Ex. 79 | poly-γ-methyl-L-glutamic acid KOH treatment | film | +++ |
| Prod. Ex. 82 | poly-L-alanine/γ-methyl-L-glutamic acid 3/7 KOH treatment | film | ++ |
| Prod. Ex. 83 | poly-L-phenylalanine/γ-methyl-L-glutamic acid 6/4 KOH treatment | film | ++ |
| Prod. Ex. 85 | poly-L-valine/$N^\epsilon$-benzyloxycarbonyl-L-lysine 6/4 HBr-treated product | film | + |
| Prod. Ex. 86 | poly-L-isoleucine/$N^\epsilon$-benzyloxycarbonyl-L-lysine 6/4 HBr treatment | film | ++ |
| Prod. Ex. 61 | poly-$N^\epsilon$-benzyloxycarbonyl-L-lysine | coating | ++ |
| Prod. Ex. 62 | poly-L-alanine/$N^\epsilon$-benzyloxycarbonyl-L-lysine 6/4 | coating | +++ |
| Prod. Ex. 63 | poly-L-alanine/$N^\epsilon$-benzyloxycarbonyl-L-lysine 3/7 | coating | + |
| Prod. Ex. 87 | poly-$N^\epsilon$-benzyloxycarbonyl-L-lysine HBr treatment | coating | + |
| Prod. Ex. 88 | poly-L-alanine/$N^\epsilon$-benzyloxycarbonyl-L-lysine 6/4 HBr treatment | coating | +++ |
| Prod. Ex. 89 | poly-L-alanine/$N^\epsilon$-benzyloxycarbonyl-L-lysine 3/7 HBr treatment | coating | + |

Production Examples 35, 45, 46, 47, 65, 66, 72, 73, 74, 76, 50, 51, 54, 57, 58, 59, 60, 79, 82, 83, 85, 86, 61, 62, 63, 87, 88 and 89 could provide medical materials superior in the cell adhesion effect. Of those, poly-γ-methyl-L-glutamic acid (film), poly-L-valine/L-phenylalanine 5/5 (film), poly-γ-methyl-L-glutamic acid KOH treatment (film), poly-$N^\epsilon$-benzyloxycarbonyl-L-lysine (coating), poly-L-alanine/$N^\epsilon$-benzyloxycarbonyl-L-lysine 6/4 (coating), poly-L-alanine/$N^\epsilon$-benzyloxycarbonyl-L-lysine 6/4 HBr treatment (coating) are clearly medical materials particularly superior in the cell adhesion effect.

[Evaluation 9] Evaluation of Cell Differentiation Promoting Effect

In the same manner as in the above-mentioned evaluation method for the cell adhesion effect, cells were seeded and cultured. The number of the plated cells was 40,000 cells/well. After plating and culture for 3 days, the medium was exchanged with Dulbecco's Modified Eagle Medium containing inactivated fetal bovine serum (Invitrogen Corporation, GIBCO FBS), penicillin-streptomycin (Sigma-Aldrich Corporation), dexamethasone (NACALAI TESQUE, INC.), isobutylmethylxanthine (NACALAI TESQUE, INC.), indomethacin (NACALAI TESQUE, INC.) and insulin (Sigma-Aldrich Corporation) (Invitrogen Corporation, GIBCO DMEM) (adipocyte differentiation induction medium) and the cells were cultured for 4 days, after which the medium was exchanged with Dulbecco's Modified Eagle Medium containing inactivated fetal bovine serum (Invitrogen Corporation, GIBCO FBS), penicillin-streptomycin (Sigma-Aldrich Corporation) and insulin (Sigma-Aldrich Corporation) (Invitrogen Corporation, GIBCO DMEM) (adipocyte differentiation maintenance medium) and the cells were cultured for 3 days. After culture in the adipocyte differentiation induction medium and the adipocyte differentiation maintenance medium for 2 weeks or 3 weeks, the amount of cellular DNA and glycerol-3-phosphate dehydrogenase (GPDH) activity level were quantified. The quantification of the cellular DNA was performed in the same manner as in the evaluation method of the above-mentioned cell adhesion growth effect and GPDH activity level was quantified using a GPDH activity measurement kit (primary Cell Co., Ltd.). The GPDH activity was divided by the amount of the cellular DNA to determine the percentage relative to the control.

These results are shown in Table 9-1, Table 9-2, Table 9-3 and Table 9-4.

TABLE 9-1

| Prod. Ex. | constituting polymer | form | evaluation 9 differentiation efficiency |
|---|---|---|---|
| Prod. Ex. 33 | poly-L-alanine | fiber structure | 484 |
| Prod. Ex. 34 | poly-L-valine | fiber structure | 191 |
| Prod. Ex. 35 | poly-γ-methyl-L-glutamic acid | fiber structure | 224 |
| Prod. Ex. 65 | poly-γ-methyl-L-glutamic acid KOH treatment | fiber structure | 259 |
| Prod. Ex. 66 | poly-N$^\epsilon$-benzyloxycarbonyl-L-lysine HBr treatment | fiber structure | 157 |
| Prod. Ex. 67 | poly-L-alanine/γ-methyl-glutamic acid 9/1 KOH treatment | fiber structure | 141 |
| Prod. Ex. 68 | poly-L-alanine/γ-methyl-L-glutamic acid 6/4 KOH treatment | fiber structure | 115 |
| Prod. Ex. 69 | poly-L-leucine/γ-methyl-L-glutamic acid 9/1 KOH treatment | fiber structure | 176 |
| Prod. Ex. 70 | poly-L-leucine/γ-methyl-L-glutamic acid 6/4 KOH treatment | fiber structure | 172 |
| Prod. Ex. 71 | poly-L-alanine/N$^\epsilon$-benzyloxycarbonyl-L-lysine 9/1 HBr treatment | fiber structure | 140 |
| Prod. Ex. 72 | poly-L-alanine/N$^\epsilon$-benzyloxycarbonyl-L-lysine 6/4 HBr treatment | fiber structure | 137 |
| Prod. Ex. 73 | poly-L-alanine/N$^\epsilon$-benzyloxycarbonyl-L-lysine 3/7 HBr treatment | fiber structure | 246 |
| Prod. Ex. 74 | poly-L-phenylalanine/N$^\epsilon$-benzyloxycarbonyl-L-lysine 9/1 HBr treatment | fiber structure | 257 |
| Prod. Ex. 75 | poly-L-phenylalanine/N$^\epsilon$-benzyloxycarbonyl-L-lysine 6/4 HBr treatment | fiber structure | 252 |
| Prod. Ex. 76 | poly-L-phenylalanine/N$^\epsilon$-benzyloxycarbonyl-L-lysine 3/7 HBr treatment | fiber structure | 338 |
| Prod. Ex. 77 | poly-L-alanine + poly-N$^\epsilon$-benzyloxycarbonyl-L-lysine 9 + 1 HBr treatment | fiber structure | 179 |
| Prod. Ex. 78 | poly-L-alanine + poly-N$^\epsilon$-benzyloxycarbonyl-L-lysine 6 + 4 HBr treatment | fiber structure | 368 |
| Prod. Ex. 50 | poly-L-valine | film | 134 |
| Prod. Ex. 51 | poly-γ-methyl-L-glutamic acid | film | 148 |
| Prod. Ex. 56 | poly-L-alanine/N$^\epsilon$-benzyloxycarbonyl-L-lysine 9/1 | film | 213 |
| Prod. Ex. 58 | poly-L-isoleucine/N$^\epsilon$-benzyloxycarbonyl-L-lysine 6/4 | film | 145 |
| Prod. Ex. 79 | poly-γ-methyl-L-glutamic acid KOH treatment | film | 140 |
| Prod. Ex. 61 | poly-N$^\epsilon$-benzyloxycarbonyl-L-lysine | coating | 197 |
| Prod. Ex. 62 | poly-L-alanine/N$^\epsilon$-benzyloxycarbonyl-L-lysine 6/4 | coating | 129 |
| Prod. Ex. 63 | poly-L-alanine/N$^\epsilon$-benzyloxycarbonyl-L-lysine 3/7 | coating | 110 |
| Prod. Ex. 64 | poly-L-phenylalanine/N$^\epsilon$-benzyloxycarbonyl-L-lysine 6/4 | coating | 111 |
| Prod. Ex. 87 | poly-N$^\epsilon$-benzyloxycarbonyl-L-lysine HBr treatment | coating | 150 |
| Prod. Ex. 88 | poly-L-alanine/N$^\epsilon$-benzyloxycarbonyl-L-lysine 6/4 HBr treatment | coating | 136 |
| Prod. Ex. 89 | poly-L-alanine/N$^\epsilon$-benzyloxycarbonyl-L-lysine 3/7 HBr treatment | coating | 156 |

TABLE 9-2

| Prod. Ex. | constituting polymer | form | evaluation 9 differentiation efficiency |
|---|---|---|---|
| Prod. Ex. 37 | poly-N$^\epsilon$-benzyloxycarbonyl-L-lysine | fiber structure | 277 |
| Prod. Ex. 38 | poly-L-alanine/γ-methyl-L-glutamic acid 9/1 | fiber structure | 140 |
| Prod. Ex. 39 | poly-L-alanine/γ-methyl-L-glutamic acid 6/4 | fiber structure | 142 |
| Prod. Ex. 40 | poly-L-leucine/γ-methyl-L-glutamic acid 9/1 | fiber structure | 142 |
| Prod. Ex. 41 | poly-L-leucine/γ-methyl-L-glutamic acid 6/4 | fiber structure | 163 |
| Prod. Ex. 42 | poly-L-alanine/N$^\epsilon$-benzyloxycarbonyl-L-lysine 9/1 | fiber structure | 276 |
| Prod. Ex. 43 | poly-L-alanine/N$^\epsilon$-benzyloxycarbonyl-L-lysine 6/4 | fiber structure | 281 |
| Prod. Ex. 44 | poly-L-alanine/N$^\epsilon$-benzyloxycarbonyl-L-lysine 3/7 | fiber structure | 215 |
| Prod. Ex. 45 | poly-L-phenylalanine/N$^\epsilon$-benzyloxycarbonyl-L-lysine 9/1 | fiber structure | 251 |
| Prod. Ex. 46 | poly-L-phenylalanine/N$^\epsilon$-benzyloxycarbonyl-L-lysine 6/4 | fiber structure | 279 |
| Prod. Ex. 47 | poly-L-phenylalanine/N$^\epsilon$-benzyloxycarbonyl-L-lysine 3/7 | fiber structure | 275 |
| Prod. Ex. 57 | poly-L-valine/N$^\epsilon$-benzyloxycarbonyl-L-lysine 6/4 | film | 162 |
| Prod. Ex. 59 | poly-L-valine/L-phenylalanine 5/5 | film | 168 |
| Prod. Ex. 85 | poly-L-valine/N$^\epsilon$-benzyloxycarbonyl-L-lysine 6/4 surface HBr treatment | film | 146 |
| Prod. Ex. 86 | poly-L-isoleucine/N$^\epsilon$-benzyloxycarbonyl-L-lysine 6/4 surface HBr treatment | film | 144 |

TABLE 9-3

| Prod. Ex. | constituting polymer | form | evaluation 9 differentiation efficiency |
|---|---|---|---|
| Prod. Ex. 2 | poly-L-leucine | fiber structure | 250 |
| Prod. Ex. 4 | poly-β-benzyl-L-aspartic acid | fiber structure | 101 |
| Prod. Ex. 12 | poly-L-valine/γ-methyl-L-glutamic acid 6/4 | fiber structure | 246 |
| Prod. Ex. 13 | poly-L-isoleucine/γ-methyl-L-glutamic acid 6/4 | fiber structure | 435 |
| Prod. Ex. 14 | poly-L-phenylalanine/γ-methyl-L-glutamic acid 9/1 | fiber structure | 241 |
| Prod. Ex. 15 | poly-L-phenylalanine/γ-methyl-L-glutamic acid 6/4 | fiber structure | 195 |
| Prod. Ex. 19 | poly-L-valine/N$^\epsilon$-benzyloxycarbonyl-L-lysine 6/4 | fiber structure | 207 |

TABLE 9-3-continued

| Prod. Ex. | constituting polymer | form | evaluation 9 differentiation efficiency |
|---|---|---|---|
| Prod. Ex. 20 | poly-L-isoleucine/N$^\epsilon$-benzyloxycarbonyl-L-lysine 6/4 | fiber structure | 280 |
| Prod. Ex. 21 | poly-L-leucine/L-phenylalanine 1/1 | fiber structure | 240 |
| Prod. Ex. 22 | poly-L-valine/L-phenylalanine 1/1 | fiber structure | 207 |
| Prod. Ex. 92 | poly-L-phenylalanine/benzyl-L-aspartic acid/γ-methyl-L-glutamic acid 3/2/5 | fiber structure | 166 |
| Prod. Ex. 93 | poly-L-phenylalanine/benzyl-L-aspartic acid/N$^\epsilon$-benzyloxycarbonyl-L-lysine 3/2/5 | fiber structure | 212 |
| Prod. Ex. 94 | poly-L-leucine/L-glutamic acid 8/2 | fiber structure | 142 |
| Prod. Ex. 95 | poly-L-leucine/N$^\epsilon$-benzyloxycarbonyl-L-lysine 9/1 | fiber structure | 326 |
| Prod. Ex. 96 | poly-L-leucine/N$^\epsilon$-benzyloxycarbonyl-L-lysine 6/4 | fiber structure | 222 |
| Prod. Ex. 97 | poly-L-leucine/L-lysine 8/2 | fiber structure | 355 |
| Prod. Ex. 98 | poly-L-leucine/L-glutamic acid/L-lysine 8/1/1 | fiber structure | 119 |
| Prod. Ex. 110 | poly-L-valine/γ-methyl-L-glutamic acid 6/4 surface KOH treatment | fiber structure | 113 |
| Prod. Ex. 111 | poly-L-isoleucine/γ-methyl-L-glutamic acid 6/4 surface KOH treatment | fiber structure | 170 |
| Prod. Ex. 112 | poly-L-phenylalanine/γ-methyl-L-glutamic acid 9/1 surface KOH treatment | fiber structure | 161 |
| Prod. Ex. 113 | poly-L-phenylalanine/γ-methyl-L-glutamic acid 6/4 surface KOH treatment | fiber structure | 270 |
| Prod. Ex. 114 | poly-L-phenylalanine/benzyl-L-aspartic acid/γ-methyl-L-glutamic acid 3/2/5 surface KOH treatment | fiber structure | 116 |

TABLE 9-4

| Prod. Ex. | constituting polymer | form | evaluation 9 differentiation efficiency |
|---|---|---|---|
| Prod. Ex. 115 | poly-L-valine/N$^\epsilon$-benzyloxycarbonyl-L-lysine 6/4 surface HBr treatment | fiber structure | 194 |
| Prod. Ex. 116 | poly-L-isoleucine/N$^\epsilon$-benzyloxycarbonyl-L-lysine 6/4 surface HBr treatment | fiber structure | 211 |
| Prod. Ex. 117 | poly-L-phenylalanine/benzyl-L-aspartic acid/N$^\epsilon$-benzyloxycarbonyl-L-lysine 3/2/5 surface HBr treatment | fiber structure | 187 |
| Prod. Ex. 118 | poly-L-leucine/N$^\epsilon$-benzyloxycarbonyl-L-lysine 9/1 surface HBr treatment | fiber structure | 335 |
| Prod. Ex. 119 | poly-L-leucine/N$^\epsilon$-benzyloxycarbonyl-L-lysine 6/4 surface HBr treatment | fiber structure | 265 |
| Prod. Ex. 99 | poly-γ-methyl-L-glutamic acid/L-glutamic acid 8/2 | film | 207 |
| Prod. Ex. 100 | (poly-L-N$^\epsilon$-benzyloxycarbonyl-L-lysine/N$^\epsilon$-acetyl-L-lysine 6/4) + (poly-γ-methyl-L-glutamic acid) 1 + 1 | film | 164 |
| Prod. Ex. 101 | poly-L-valine/γ-methyl-L-glutamic acid 6/4 | film | 234 |
| Prod. Ex. 102 | poly-L-isoleucine/γ-methyl-L-glutamic acid 6/4 | film | 199 |
| Prod. Ex. 103 | poly-L-phenylalanine/benzyl-L-aspartic acid/γ-methyl-L-glutamic acid 3/2/5 | film | 130 |
| Prod. Ex. 104 | poly-L-phenylalanine/benzyl-L-aspartic acid/N$^\epsilon$-benzyloxycarbonyl-L-lysine 3/2/5 | film | 159 |
| Prod. Ex. 120 | poly-L-valine/γ-methyl-L-glutamic acid 6/4 surface KOH treatment | film | 172 |
| Prod. Ex. 121 | poly-L-isoleucine/γ-methyl-L-glutamic acid 6/4 surface KOH treatment | film | 169 |
| Prod. Ex. 122 | poly-L-phenylalanine/benzyl-L-aspartic acid/γ-methyl-L-glutamic acid 3/2/5 surface KOH treatment | film | 143 |
| Prod. Ex. 123 | poly-L-phenylalanine/benzyl-L-aspartic acid/N$^\epsilon$-benzyloxycarbonyl-L-lysine 3/2/5 surface HBr treatment | film | 146 |
| Prod. Ex. 105 | poly-L-glycine | coating | 128 |
| Prod. Ex. 106 | poly-L-N$^\epsilon$-benzyloxycarbonyl-L-lysine/L-lysine 6/4 | coating | 171 |
| Prod. Ex. 107 | Poly-N$^\epsilon$-benzyloxycarbonyl-L-lysine/N$^\epsilon$-t-butoxycarbonylguanidino-L-lysine 6/4 | coating | 187 |
| Prod. Ex. 30 | chitosan | fiber structure | 0 |

As shown in Table 8 and 9-1, the poly-γ-methyl-L-glutamic acid fiber structures showed high differentiation efficiency in addition to the cell adhesion effect (Production Example 35). It was shown that a KOH treatment of the poly-γ-methyl-L-glutamic acid fiber structure not only improved the cell adhesion effect but showed high differentiation efficiency (Production Example 65). They are preferable as a scaffold requested to show a cell differentiation promoting effect, as well as a scaffold requested to show a cell adhesion effect. In addition, since all of them are fiber structures with a controlled fiber diameter, they are preferably used in vivo. The poly-N$^\epsilon$-benzyloxycarbonyl-L-lysine coating and a HBr-treated product thereof also showed a cell adhesion effect, as well as high differentiation efficiency (Production Examples 61, 87). They are also preferable as a scaffold requested to provide a cell differentiation promoting effect, and also useful as a scaffold requested to provide a cell adhesion effect. Moreover, since all of them are coatings with a controlled film thickness, they are preferably used as a medical material or cell supporting substrate requesting a cell scaffold function, by coating a surface of various medical substrates or supporting substrates. While a higher numerical value of the above-mentioned differentiation efficiency shows higher effectiveness for cell differentiation, the numerical value is preferably not less than 120, more preferably not less than 200.

INDUSTRIAL APPLICABILITY

According to the present invention, a medical material for promoting cell differentiation, which is safe for the live body, has high biocompatibility, and is useful as a scaffold for biological tissues and cells. Moreover, since the medical material for promoting cell differentiation of the present invention can provide a cell adhesion suppressive effect or cell adhesion effect by appropriately adjusting the constituent components, it can be utilized as a scaffold for a wide range of applications.

This application is based on a patent application No. 2010-272043 filed in Japan (filing date: Dec. 6, 2010), the contents of which are incorporated in full herein.

The invention claimed is:

1. A method for promoting mesenchymal stem cell differentiation, which comprises:
   (a) cultivating a mesenchymal stem cell in the presence of a medical material comprising a polyamino acid, or
   (b) transplanting a medical material comprising a polyamino acid to a subject in need thereof,
   wherein the medical material has a cell adhesion suppressive effect, and
   wherein the polyamino acid consists of:
   (i) one kind of amino acid residue selected from the group consisting of an alanine residue, a valine residue, a leucine residue, a phenylalanine residue, a glycine residue, a glutamine residue, an aspartic acid residue containing a protecting group in the side chain, a tyrosine residue optionally containing a protecting group in the side chain, a tryptophan residue optionally containing a protecting group in the side chain, a lysine residue containing a protecting group in the side chain, and a glutamic acid residue containing a protecting group in the side chain; or
   (ii) two kinds of amino acid residues selected from the group consisting of an alanine residue, a valine residue, a leucine residue, an isoleucine residue, a phenylalanine residue, a lysine residue optionally containing a protecting group in the side chain, and a glutamic acid residue optionally containing a protecting group in the side chain,
   excluding polyamino acids consisting of two kinds of amino acid residues of (1) glutamic acid and alanine and (2) lysine and phenylalanine;
   wherein the medical material is a fiber structure,
   wherein the polyamino acid is:
   poly-L-alanine;
   poly-L-valine;
   poly-$N^\epsilon$-benzyloxycarbonyl-L-lysine;
   poly-L-alanine/$\gamma$-methyl-L-glutamic acid;
   poly-L-leucine/$\gamma$-methyl-L-glutamic acid;
   poly-L-alanine/$N^\epsilon$-benzyloxycarbonyl-L-lysine;
   poly-L-leucine;
   poly-L-valine/$\gamma$-methyl-L-glutamic acid;
   poly-L-isoleucine/$\gamma$-methyl-L-glutamic acid;
   poly-L-phenylalanine/$\gamma$-methyl-L-glutamic acid;
   poly-L-valine/$N^\epsilon$-benzyloxycarbonyl-L-lysine;
   poly-L-isoleucine/$N^\epsilon$-benzyloxycarbonyl-L-lysine; or
   poly-L-valine/L-phenylalanine.

2. The method according to claim 1, wherein the fiber has an average fiber diameter of not less than 50 nm and less than 500 nm.

3. The method according to claim 1, wherein said method comprises cultivating a mesenchymal stem cell in the presence of a medical material comprising a polyamino acid.

4. The method according to claim 1, wherein said method comprises transplanting a medical material comprising a polyamino acid to a subject in need thereof.

5. The method according to claim 1, wherein the medical material causes a differentiation efficiency of the mesenchymal stem cell to be 1.36 times greater than a differentiation efficiency of the mesenchymal stem cell not cultivated in the presence of the medical material.

6. The method according to claim 1, wherein the polyamino acid is poly-L-alanine.

7. The method according to claim 1, wherein the polyamino acid is poly-L-valine.

8. The method according to claim 1, wherein the polyamino acid is poly-$N^\epsilon$-benzyloxycarbonyl-L-lysine.

9. The method according to claim 1, wherein the polyamino acid is poly-L-alanine/$\gamma$-methyl-L-glutamic acid.

10. The method according to claim 1, wherein the polyamino acid is poly-L-leucine/$\gamma$-methyl-L-glutamic acid.

11. The method according to claim 1, wherein the polyamino acid is poly-L-alanine/$N^\epsilon$-benzyloxycarbonyl-L-lysine.

12. The method according to claim 1, wherein the polyamino acid is poly-L-leucine.

13. The method according to claim 1, wherein the polyamino acid is poly-L-valine/$\gamma$-methyl-L-glutamic acid.

14. The method according to claim 1, wherein the polyamino acid is poly-L-isoleucine/$\gamma$-methyl-L-glutamic acid.

15. The method according to claim 1, wherein the polyamino acid is poly-L-phenylalanine/$\gamma$-methyl-L-glutamic acid.

16. The method according to claim 1, wherein the polyamino acid is poly-L-valine/$N^\epsilon$-benzyloxycarbonyl-L-lysine.

17. The method according to claim 1, wherein the polyamino acid is poly-L-isoleucine/$N^\epsilon$-benzyloxycarbonyl-L-lysine.

18. The method according to claim 1, wherein the polyamino acid is poly-L-valine/L-phenylalanine.

19. A method for promoting mesenchymal stem cell differentiation, which comprises:
   (a) cultivating a mesenchymal stem cell in the presence of a medical material comprising a polyamino acid, or
   (b) transplanting a medical material comprising a polyamino acid to a subject in need thereof,
   wherein the medical material has a cell adhesion suppressive effect,
   wherein the medical material is a fiber structure, and
   wherein the polyamino acid is:
   poly-L-alanine;
   poly-L-leucine;
   poly-L-valine;
   poly-$\beta$-benzyl-L-aspartic acid;
   poly-$N^\epsilon$-benzyloxycarbonyl-L-lysine;
   poly-O-acetyl-L-tyrosine;
   poly-L-tryptophan;
   poly-$\gamma$-benzyl-L-glutamic acid;
   poly-L-alanine/$\gamma$-methyl-L-glutamic acid;
   poly-L-leucine/$\gamma$-methyl-L-glutamic acid;
   poly-L-valine/$\gamma$-methyl-L-glutamic acid;
   poly-L-isoleucine/$\gamma$-methyl-L-glutamic acid;
   poly-L-phenylalanine/$\gamma$-methyl-L-glutamic acid;
   poly-L-alanine/$N^\epsilon$-benzyloxycarbonyl-L-lysine;
   poly-L-valine/$N^\epsilon$-benzyloxycarbonyl-L-lysine;
   poly-L-isoleucine/$N^\epsilon$-benzyloxycarbonyl-L-lysine;
   poly-L-leucine/L-phenylalanine;
   poly-L-valine/L-phenylalanine;

poly-L-glutamine/γ-methyl-L-glutamic acid;
poly-γ-(methyl/polyethylene glycol)-L-glutamic acid;
poly-L-alanine/L-lysine;
poly-L-alanine-poly-L-lysine; or
poly-L-alanine-poly-N$^\epsilon$-benzyloxycarbonyl-L-lysine.

20. The method according to claim 19, wherein the polyamino acid is:
poly-L-alanine;
poly-L-leucine;
poly-L-valine;
poly-β-benzyl-L-aspartic acid;
poly-N$^\epsilon$-benzyloxycarbonyl-L-lysine;
poly-L-alanine/γ-methyl-L-glutamic acid;
poly-L-valine/γ-methyl-L-glutamic acid;
poly-L-isoleucine/γ-methyl-L-glutamic acid;
poly-L-alanine/N$^\epsilon$-benzyloxycarbonyl-L-lysine;
poly-L-valine/N$^\epsilon$-benzyloxycarbonyl-L-lysine;
poly-L-isoleucine/N$^\epsilon$-benzyloxycarbonyl-L-lysine;
poly-L-valine/L-phenylalanine;
poly-γ-(methyl/polyethylene glycol)-L-glutamic acid;
poly-L-alanine/L-lysine;
poly-L-alanine-poly-L-lysine; or
poly-L-alanine-poly-Nϵ-benzyloxycarbonyl-L-lysine.

21. The method according to claim 19, wherein the polyamino acid is:
poly-L-alanine;
poly-L-leucine;
poly-L-valine;
poly-L-alanine/γ-methyl-L-glutamic acid;
poly-L-isoleucine/γ-methyl-L-glutamic acid;
poly-L-alanine/N$^\epsilon$-benzyloxycarbonyl-L-lysine;
poly-L-valine/N$^\epsilon$-benzyloxycarbonyl-L-lysine;
poly-L-alanine/L-lysine;
poly-L-alanine-poly-L-lysine; or
poly-L-alanine-poly-N$^\epsilon$-benzyloxycarbonyl-L-lysine.

* * * * *